United States Patent
Goix et al.

(10) Patent No.: US 9,040,305 B2
(45) Date of Patent: May 26, 2015

(54) METHOD OF ANALYSIS FOR DETERMINING A SPECIFIC PROTEIN IN BLOOD SAMPLES USING FLUORESCENCE SPECTROMETRY

(75) Inventors: Philippe J. Goix, Oakland, CA (US);
Robert Puskas, Manchester, MO (US);
John Todd, Lafayette, CA (US);
Richard A. Livingston, Webster Groves, MO (US); Douglas Held, Ballwin, MO (US)

(73) Assignee: Singulex, Inc., Alameda, CA (US)

( * ) Notice: Subject to any disclaimer, the term of this patent is extended or adjusted under 35 U.S.C. 154(b) by 1717 days.

(21) Appl. No.: 11/767,196

(22) Filed: Jun. 22, 2007

(65) Prior Publication Data

US 2008/0003685 A1    Jan. 3, 2008

Related U.S. Application Data

(63) Continuation-in-part of application No. 11/048,660, filed on Jan. 28, 2005, now abandoned.

(60) Provisional application No. 60/613,881, filed on Sep. 28, 2004, provisional application No. 60/624,785,
(Continued)

(51) Int. Cl.
*G01N 33/00* (2006.01)
*G01N 33/58* (2006.01)

(52) U.S. Cl.
CPC .................................. *G01N 33/582* (2013.01)

(58) Field of Classification Search
CPC .............. G01N 33/533; G01N 33/582; G01N 27/44743; G01N 27/44791; G01N 33/68; G01N 21/645; G01N 15/1434; G01N 15/1463; G01N 2015/0038; G01N 2015/1447; G01N 2015/1452; G01N 33/53; G01N 33/587
See application file for complete search history.

(56) References Cited

U.S. PATENT DOCUMENTS

| | | | |
|---|---|---|---|
| 3,872,312 A | 3/1975 | Hirschfeld |
| 4,071,298 A | 1/1978 | Falconer |
| 4,168,146 A | 9/1979 | Grubb et al. |
| 4,172,227 A | 10/1979 | Tyrer et al. |

(Continued)

FOREIGN PATENT DOCUMENTS

| DE | 3720844 A1 | 1/1989 |
|---|---|---|
| EP | 0245206 | 11/1987 |

(Continued)

OTHER PUBLICATIONS

Petra Schwille and Elke Haustein "Fluorescence Correlation Spectroscopy: An Introduction to its Concepts and Applications", Experimental Biophysics Group Max-Planck-Institute for Biophysical Chemistry Germany, May 17, 2004, pp. 1-33.*

(Continued)

*Primary Examiner* — Yelena G Gakh
(74) *Attorney, Agent, or Firm* — McDonnell Boehnen Hulbert & Berghoff LLP

(57) ABSTRACT

The invention encompasses analyzers and analyzer systems that include a single particle analyzer, methods of using the analyzers and analyzers systems to analyze samples, either for single particles, e.g., protein molecules, or for multiple particles (multiplexing), methods of doing business based on the use of the analyzers or analyzer systems of the system, and electronic media for storing parameters useful in the analyzers and analyzer systems of the invention.

16 Claims, 24 Drawing Sheets

Related U.S. Application Data filed on Oct. 29, 2004, provisional application No. 60/636,158, filed on Dec. 16, 2004, provisional application No. 60/861,498, filed on Nov. 28, 2006, provisional application No. 60/872,986, filed on Dec. 4, 2006.

(56) References Cited

U.S. PATENT DOCUMENTS

| | | |
|---|---|---|
| 4,235,601 A | 11/1980 | Deutsch et al. |
| 4,243,318 A | 1/1981 | Stohr |
| 4,251,733 A | 2/1981 | Hirleman, Jr. |
| 4,366,241 A | 12/1982 | Tom et al. |
| 4,442,204 A | 4/1984 | Greenquist et al. |
| 4,452,773 A | 6/1984 | Molday |
| 4,750,837 A | 6/1988 | Gifford et al. |
| 4,768,879 A | 9/1988 | McLachlan et al. |
| 4,770,183 A | 9/1988 | Groaman et al. |
| 4,793,705 A | 12/1988 | Shera |
| 4,927,265 A | 5/1990 | Brownlee |
| 4,979,824 A | 12/1990 | Mathies et al. |
| 5,002,389 A | 3/1991 | Benser |
| 5,041,733 A | 8/1991 | Noguchi et al. |
| 5,094,594 A | 3/1992 | Brennan |
| 5,108,179 A | 4/1992 | Myers |
| 5,138,170 A | 8/1992 | Noguchi et al. |
| 5,208,535 A | 5/1993 | Nakayama et al. |
| 5,208,651 A | 5/1993 | Buican |
| 5,209,834 A | 5/1993 | Shera |
| 5,230,997 A * | 7/1993 | Frenkel ............... 435/5 |
| 5,269,937 A | 12/1993 | Dollinger et al. |
| 5,274,240 A | 12/1993 | Mathies et al. |
| 5,385,707 A | 1/1995 | Miltenyi et al. |
| 5,480,614 A | 1/1996 | Kamahori |
| 5,540,494 A | 7/1996 | Purvis, Jr. et al. |
| 5,543,838 A | 8/1996 | Hosier et al. |
| 5,547,849 A | 8/1996 | Bear et al. |
| 5,571,410 A | 11/1996 | Swedberg et al. |
| 5,603,351 A | 2/1997 | Cherukuri et al. |
| 5,605,662 A | 2/1997 | Heller et al. |
| 5,608,519 A | 3/1997 | Gourley et al. |
| 5,633,503 A | 5/1997 | Kosaka |
| 5,645,702 A | 7/1997 | Witt et al. |
| 5,653,859 A | 8/1997 | Parton et al. |
| 5,653,939 A | 8/1997 | Hollis et al. |
| 5,658,413 A | 8/1997 | Kaltenbach et al. |
| 5,681,751 A | 10/1997 | Begg et al. |
| 5,682,038 A | 10/1997 | Hoffman |
| 5,716,825 A | 2/1998 | Hancock et al. |
| 5,730,187 A | 3/1998 | Howitz et al. |
| 5,746,901 A | 5/1998 | Balch et al. |
| 5,755,942 A | 5/1998 | Zanzucchi et al. |
| 5,770,029 A | 6/1998 | Nelson et al. |
| 5,793,485 A | 8/1998 | Gourley |
| 5,795,158 A | 8/1998 | Warinner |
| 5,798,222 A | 8/1998 | Goix |
| 5,807,677 A | 9/1998 | Eigen et al. |
| 5,808,300 A | 9/1998 | Caprioli |
| 5,858,195 A | 1/1999 | Ramsey |
| 5,863,801 A | 1/1999 | Southgate et al. |
| 5,949,532 A | 9/1999 | Schrof et al. |
| 5,955,028 A | 9/1999 | Chow |
| 5,989,402 A | 11/1999 | Chow et al. |
| 5,999,250 A | 12/1999 | Hairston et al. |
| 6,033,628 A | 3/2000 | Kaltenbach et al. |
| 6,041,515 A | 3/2000 | Ally et al. |
| 6,049,380 A | 4/2000 | Goodwin et al. |
| 6,071,478 A | 6/2000 | Chow |
| 6,114,180 A | 9/2000 | Doth et al. |
| 6,130,101 A | 10/2000 | Mao et al. |
| 6,131,101 A | 10/2000 | Maitino et al. |
| 6,132,580 A | 10/2000 | Mathies et al. |
| 6,140,048 A | 10/2000 | Muller et al. |
| 6,143,152 A | 11/2000 | Simpson et al. |
| 6,177,277 B1 | 1/2001 | Soini |
| 6,200,818 B1 | 3/2001 | Eigen et al. |
| 6,208,815 B1 | 3/2001 | Seidel et al. |
| 6,211,955 B1 | 4/2001 | Basiji et al. |
| 6,242,266 B1 * | 6/2001 | Schleifer et al. ............... 436/518 |
| 6,249,341 B1 | 6/2001 | Basiji et al. |
| 6,280,960 B1 | 8/2001 | Carr |
| 6,309,886 B1 | 10/2001 | Ambrose et al. |
| 6,355,420 B1 | 3/2002 | Chan |
| 6,361,671 B1 | 3/2002 | Mathies et al. |
| 6,372,185 B1 | 4/2002 | Shumate et al. |
| 6,386,219 B1 | 5/2002 | Barth et al. |
| 6,388,746 B1 | 5/2002 | Eriksson et al. |
| 6,394,305 B1 | 5/2002 | Sydlosky et al. |
| 6,403,338 B1 | 6/2002 | Knapp et al. |
| 6,403,947 B1 | 6/2002 | Hoyt et al. |
| 6,473,176 B2 | 10/2002 | Basiji et al. |
| 6,495,104 B1 | 12/2002 | Unno et al. |
| 6,506,609 B1 | 1/2003 | Wada et al. |
| 6,528,802 B1 | 3/2003 | Koenig et al. |
| 6,532,067 B1 | 3/2003 | Chang et al. |
| 6,533,553 B2 | 3/2003 | Caren |
| 6,537,437 B1 | 3/2003 | Galambos et al. |
| 6,554,744 B2 | 4/2003 | Schmidt |
| 6,556,296 B1 | 4/2003 | Palo |
| 6,582,903 B1 | 6/2003 | Rigler et al. |
| 6,599,436 B1 | 7/2003 | Matzke et al. |
| 6,608,680 B2 | 8/2003 | Basiji et al. |
| 6,623,613 B1 | 9/2003 | Mathies et al. |
| 6,689,323 B2 | 2/2004 | Fisher et al. |
| 6,710,871 B1 | 3/2004 | Goix |
| 6,741,344 B1 | 5/2004 | Stern et al. |
| 6,749,734 B1 | 6/2004 | Simpson et al. |
| 6,766,817 B2 | 7/2004 | Da Silva |
| 6,783,649 B2 | 8/2004 | Hedberg et al. |
| 6,783,992 B2 | 8/2004 | Robotti et al. |
| 6,802,342 B2 | 10/2004 | Fernandes et al. |
| 6,811,668 B1 | 11/2004 | Berndt et al. |
| 6,816,257 B2 | 11/2004 | Goix |
| 6,856,712 B2 | 2/2005 | Fauver et al. |
| 6,918,404 B2 | 7/2005 | Dias Da Silva |
| 6,974,305 B2 | 12/2005 | Garrett, III |
| 6,974,874 B2 | 12/2005 | Venham et al. |
| 6,977,305 B2 | 12/2005 | Leung et al. |
| 7,056,427 B2 | 6/2006 | Yamamoto et al. |
| 7,066,586 B2 | 6/2006 | Da Silva |
| 7,355,701 B2 | 4/2008 | Ishibashi et al. |
| 7,390,677 B2 | 6/2008 | Nakashima et al. |
| 7,476,545 B2 | 1/2009 | Kinjo et al. |
| 7,507,582 B2 | 3/2009 | Heinze et al. |
| 7,534,576 B2 | 5/2009 | Rigler et al. |
| 7,572,640 B2 | 8/2009 | Goix et al. |
| 7,626,400 B2 | 12/2009 | Holbrook et al. |
| 7,914,734 B2 | 3/2011 | Livingston |
| 8,252,604 B2 | 8/2012 | Rigler |
| 8,264,684 B2 | 9/2012 | Livingston |
| 8,450,069 B2 | 5/2013 | Goix et al. |
| 8,462,339 B2 | 6/2013 | Livingston |
| 8,634,075 B2 | 1/2014 | Livingston |
| 8,651,013 B2 | 2/2014 | De' Longhi |
| 2001/0040096 A1 | 11/2001 | Yamamoto et al. |
| 2002/0030812 A1 | 3/2002 | Ortyn et al. |
| 2002/0167665 A1 | 11/2002 | Yeung et al. |
| 2003/0029995 A1 | 2/2003 | Mullins et al. |
| 2003/0078737 A1 | 4/2003 | Keys et al. |
| 2003/0124592 A1 | 7/2003 | Puskas |
| 2003/0222007 A1 | 12/2003 | Gu et al. |
| 2004/0022684 A1 | 2/2004 | Heinze et al. |
| 2004/0023229 A1 | 2/2004 | Rigler |
| 2004/0142386 A1 | 7/2004 | Rigler et al. |
| 2004/0166514 A1 | 8/2004 | Puskas |
| 2004/0214211 A1 | 10/2004 | Gilmanshin et al. |
| 2005/0164205 A1 | 7/2005 | Puskas |
| 2005/0191687 A1 | 9/2005 | Wang et al. |
| 2005/0221408 A1 | 10/2005 | Nalefski et al. |
| 2006/0003333 A1 | 1/2006 | Puskas |
| 2006/0004188 A1 | 1/2006 | Leung et al. |
| 2006/0078915 A1 | 4/2006 | Fuchs et al. |
| 2006/0078998 A1 | 4/2006 | Puskas et al. |
| 2006/0099638 A1 | 5/2006 | Leung et al. |

(56) References Cited

U.S. PATENT DOCUMENTS

| | | |
|---|---|---|
| 2006/0129327 A1 | 6/2006 | Kim et al. |
| 2006/0160209 A1 | 7/2006 | Larson et al. |
| 2006/0228747 A1 | 10/2006 | Fuchs et al. |
| 2008/0003685 A1 | 1/2008 | Goix et al. |
| 2008/0064113 A1 | 3/2008 | Goix et al. |
| 2008/0117421 A1 | 5/2008 | Yamaguchi et al. |
| 2008/0158543 A1 | 7/2008 | Puskas et al. |
| 2008/0171352 A1 | 7/2008 | Goix et al. |
| 2009/0171590 A1 | 7/2009 | Puskas et al. |
| 2010/0112727 A1 | 5/2010 | Todd et al. |
| 2010/0329929 A1 | 12/2010 | Goix et al. |
| 2011/0297847 A1 | 12/2011 | Courtney et al. |
| 2012/0181450 A1 | 7/2012 | Kim et al. |
| 2014/0065722 A1 | 3/2014 | Puskas et al. |

FOREIGN PATENT DOCUMENTS

| | | |
|---|---|---|
| EP | 0488152 | 6/1992 |
| JP | 2001-021565 | 1/2001 |
| JP | 2003254891 | 9/2003 |
| JP | 2005-345311 | 12/2005 |
| WO | WO 90/10876 A1 | 9/1990 |
| WO | 99/40416 | 8/1999 |
| WO | 9954497 | 10/1999 |
| WO | WO 99/55461 A1 | 11/1999 |
| WO | WO 9958955 | 11/1999 |
| WO | WO 0222883 | 3/2002 |
| WO | WO2005/019419 | 3/2005 |
| WO | WO 2005033283 | 4/2005 |
| WO | WO 2005051967 | 6/2005 |
| WO | WO 2005/089524 A2 | 9/2005 |
| WO | 2005119265 | 12/2005 |
| WO | WO2006/014680 | 2/2006 |
| WO | 2006036182 | 4/2006 |
| WO | WO 2005/089524 A3 | 4/2006 |
| WO | 2006084283 | 8/2006 |
| WO | 2007114947 | 10/2007 |
| WO | 2007124384 | 11/2007 |
| WO | 2008/048371 | 4/2008 |

OTHER PUBLICATIONS

Nalefski, et al. Single-molecule counting of macromolecular complexes in real time: a novel approach to quantify transcription factor-DNA and antibody-antigen interactiosn. Faseb Journal. 2004; 18(8): C176.
Rigler. Fluorescence correlations, single molecule detection and large number screening. Applications in biotechnology. J Biotechnol. 1995; 41(2-3):177-86.
Panchuk-Voloshina, et al. Alexa dyes, a series of new fluorescent dyes that yield exceptionally bright, photostable conjugates. J Histochem Cytochem. Sep. 1999;47(9): 1179-88.
Alex Fluor Dyes Handbook. Simply the Best and Brightest: Fluorescent Dyes and Conjugates. Invitrongen. Copyright 2005. Molecular Probes. 1-33.
Alexa Flour Dyes. Succinimidyl Esters. Revised Jan. 4, 2006; 1-5.
Ambrose, et al. Single molecule fluorescence spectroscopy at ambient temperature. Chemical Reviews. 1999; 99(10): 2929-56.
Anazawa, et al. Electrophoretic quantitation of nucleic acids without amplification by single molecule imaging. Anal. Chem. 2002; 74(19): 5033-38.
Becker, et al. Three-dimensional photogrammetric particle-tracking velocimetry. Preparing for the Future. 1995; 5(3). Available at http://esapub.esrin.esa.it/pff/pffv5n3/beckv5n3.htm (7 pages).
Bieschke, et al., Ultrasensitive detection of pathological prion protein aggregates by dual-color scanning for intensely fluorescent targets. Proc Natl Acad Sci USA. 2000; 97(10): 5468-5473.
Bouchon, et al. Cutting edge: inflammatory responses can be triggered by TREM-1, a novel receptor expressed on neutrophils and monocytes. *The Journal of Immunology*. 2000; 164(10): 4991-1995.
Brinkmeier, et al. Two-beam cross-correlation: a method to characterize transport phenomena in micrometer-sized structures. *Anal. Chem*. 1999; 71(3): 609-616.

Castro, et al. Fluorescence detection and size measurement of single DNA molecules. *Anal. Chem*. 1993; 65(7): 849-852.
Castro, et al. Single molecule detection: applications to ultrasensitive biochemical analysis. *Applied Optics*. 1995; 34(18): 3218-3222.
Castro, et al. Single-molecule detection of specific nucleic acid sequences in unamplified genomic DNA. *Anal. Chem*. 1997; 69(19): 3915-3920.
Castro, et al. Single-molecule electrophoresis. *Anal. Chem*. 1995; 67(18):3181-3186.
Castro, et al. Ultrasensitive, direct detection of a specific DNA sequence of *Bacillus antracis* in solution. *The Analyst*. 2000; 125: 9-11.
Chan, et al. DNA mapping using microfluidic stretching and single-molecule detection of fluorescent site-specific tags. Genome Res. 2004; 14(6):1137-46.
Chen, et al. Single-molecule detection in capillary electrophoresis: molecular shot noise as a fundamental limit to chemical analysis. *Anal. Chem*. 1996; 68(4): 690-696.
Cohen, et al. Rapid separation and purification of oligonucleotides by high-performance capillary gel electrophoresis. *Proc Natl Acad Sci USA*. 1988; 85(24): 9660-9663.
Colonna, M. Trems in the immune system and beyond. *Nature Reviews: Immunology*. 2003; 3(6): 445-453.
Csiro Australia. Image motion, tracking and registration. Availabel at http://www.cmis.csiro.au/IAP/Motion/.
D'Antoni, et al. Rapid quantitative analysis using a single molecule counting approach. Anal Biochem. 2006; 352(1):97-109.
Dovichi, et al. Laser-induced fluorescence of flowing samples as an approach to single-molecule detection in liquids. *Anal. Chem*. 1984; 56(3): 348-354.
Dunbar, et al. Quantitative, multiplexed detection of bacterial pathogens: DNA and protein applictions of Luminex LabMap system. J Microbiol Methods. 2003; 53(2): 245-252.
Effenhauser, et al. Integrated capillary electrophoresis on flexible silicone microdevices: analysis of DNA restriction fragments and detection of single DNA molecules on microchips. *Anal. Chem*. 1997; 69(17): 3451-3457.
Etzioni, et al. The case for early detection. *Nature Reviews: Cancer*. 2003; 3(4): 243-252.
Fister, et al. Counting single chromphore molecules for ultrasensitive analysis and separations on microchip devices. *Anal. Chem*. 1998; 70(3): 431-437;.
Gibot, et al. Plasma level of a triggering receptor expressed on myeloid cells-1: its diagnostic accuracy in patients with suspected sepsis. *Annals of Internal Medicine*. 2004; 141(1): 9-15.
Gibot, et al. Soluble triggering receptor expressed on myeloid cells and the diagnosis of pneumonia. *The New England Journal of Medicine*. 2004; 350(5): 451-458.
Glenn Research Center, NASA. Particle Imaging Velocimetry. Availabe at http://www.grc.nasa.gOv/WWW/Optlinstr/piv/background.htm and associated web pages.
Goix, P. Fulfilling the Promise of Biomakers in Drug Discovery and Development. Drug Discovery + International. Apr./May 2007; 6-7.
Goix. Slides from presentation at Clinical Biomarkers Summit. Mar. 29-31, 2006. Coronado, CA.
Golde, T. Alzheimer disease therapy: can the amyloid cascade be halted? *The Journal of Clinical Investigation*. 2003; 11(1): 11-18.
Guenard, et al. Two-channel sequential single-molecule measurement. *Anal. Chem*. 1997; 69(13): 2426-2433.
Guide to Amine-Reactive Probes. Reviesed Oct. 13, 2005; 1-9.
Guide to Labeling Antibodies wiht Alexa Fluor Dyes. 2004; 24-28.
Haab, et al. Single molecule florescence burst detection of DNA fragments separated by capillary electrophoresis. *Anal Chem*. 1995; 67(18): 3253-3260.
Haab, et al. Single-molecule detection of DNA separations in microfabricated capillary electrophoresis chips employing focused molecular streams. *Anal Chem*. 1999; 71(22): 5137-5145.
Haugland, R. P., *Molecular Probes Handbook of Fluorescent Probes and Research Product, Ninth Edition*, 2002, Molecular Probes, Inc.
Keller, et al. Analytical applications of single-molecule detection. *Analytical Chemistry*. 2002; 74(11): 317A-324A.
Klee. Human anti-mouse antibodies. Arch Pathol Lab Med. 2000; 124(6):921-3.

(56) References Cited

OTHER PUBLICATIONS

Koerbin, et al. The Comparative analytical performance of four troponin I assays at low concentration. Ann Clin Biochem. 2005; 42(pt1): 19-23.

Lecaptain, et al. Two-beam fluorescence cross-correlation spectroscopy in an electrophoretic mobility shift assay. *Anal Chem.* 2002; 74(5): 1171-1176.

Li, et al. Ultrasensitive coincidence fluorescence detection of single DNA molecules. *Anal Chem.* 2003; 75(7): 1664-1670.

Loscher, et al. Counting of single protein molecules at interfaces and application of this technique in early-stage diagnosis. Anal Chem. 1998; 70(15): 3202-5.

Lucey, et al. Type 1 and type 2 cytokine dysregulation in human infectious, neoplastic, and inflammatory diseases. *Clinical Biology Reviews.* 1996; 9(4): 532-562.

Ma, et al. Single-molecule immunoassay and DNA diagnosis. *Electrophoresis.* 2001; 22(3): 421-426.

Nguyen, et al. Detection of single molecules of phycoerythrin in hydrodynamically focused flows by laser-induced fluorescence. *Anal Chem.* 1987; 59(17): 2158-2161.

Park. Addressing Unmet Needs in Assay Development. Medical Device Link. Mar. 2007; 1-4.

Peck, et al. Single-molecule fluorescence detection: autocorrelation criterion and experimental realization with phycoerythrim. *Proc Natl Acad Sci USA*: 1989; 86(11): 4087-4091.

Phillips, et al. Application of single molecule technology to rapidly map long DNA and study the conformation of stretched DNA. Nucleic Acids Res. 2005; 33(18):5829-37.

Puskas, R. U.S. Appl. No. 10/718,194, entitled "Preparation of defined highly labeled probes", filed Nov. 19, 2003.

Puskas, R. U.S. Appl. No. 10/720,047, entitled "Charge and mass tags for detection and analysis", filed Nov. 19, 2003.

Sauer, et al. Detection and identification of individual antigen molecules in human serum with pulsed semiconductor lasers. Appl. Phys. B. 1997; 65: 427-431.

Shera, et al. Detection of single fluorescent molecules. *Chemical Physics Letters.* 1990; 174(6): 553-557.

Shortreed, et al. High-throughput single-molecule DNA screening based on electrophoresis. *Anal Chem.* 2000; 72(13): 2879-2885.

Sidransky, D. Emerging molecular markers of cancer. *Nature Reviews: Cancer.* 2002; 2(3): 210-219.

Soper, et al. Photon burst detection of single near-infrared fluorescent molecules. *Anal Chem.* 1993; 65(6): 740-747.

Soper, et al. Single-molecule detection in the near-IR using continuous wave diode laser excitation with an avalanche photon detector. Applied Spectroscopy. 1998; 52(1): 1-6.

Tanaka, et al. Protein and polymer analyses up to m/z 100 000 by laser ionization time-of-flight mass spectrometry . Rapid Commun. Mass. Spect. 1988; 2:151-153.

Upatnieks, et al. A kilohertz frame rate cinemagraphic PIV system for laboratory-scale turbulent and unsteady flows. *Experiments in Fluids.* 2002; 32: 87-98.

Van Orden, et al. Single-molecule identification in flowing sample streams by fluorescence burst size and intraburst fluorescence decay rate. *Anal Chem.* 1998; 70(7): 1444-1451.

Wabuyele, et al. Single molecule detection of double-stranded DNA in poly(methylmethacrylate) and polycarbonate microfluidic devices. *Electrophoresis*, Oct. 2001; 22(18): 3939-3948.

Willneff, J. A spatio-temporal matching algorithm for 3D particle tracking velocimetry: a dissertation submitted to the Swiss Federal Institute of Technology Zurich for the degree of Doctoral of Technical Sciences (abstract). Sep. 2003, Diss. ETH No. 15276. Available at http://e-collection.ethbib.ethz.ch/ecol-pool/diss/abstracts/p15276.pdf.

Wu, et al. Development and preliminary clinical validation of a high sensitivity assay for cardiac troponin using a capillary flow (single molecule) fluorescence detector. Poster presented at Oak Ridge Conference. Apr. 21-22, 2006. San Jose, CA.

Wu, et al. Development and Preliminary Clinical Validation of a High Sensitivity Assay for Cardiac Troponin Using a Capillary Flow (Single Molecule) Fluorescence Detector. Clinical Chemistry. 2006; 52:2157-2159.

Young. Singules Developing Troponin Test for earlier detecton of AMI. Medical Device Daily. Dec. 13, 2006.

Zhu, et al. Fluorescence multiplexing with time-resolved and spectral discrimination using a near-IR detector. *Anal Chem.* 2003; 75(10): 2280-2291.

Goix, et al. U.S. Appl. No. 11/782,211, entitled "methods and compositions for highly sensitive detection of molecules," filed Apr. 4, 2007.

Cohen et al.: "The renal TGF-beta system in the db/db mouse model of diabetic nephropathy," Exp. Nephrol. (1998) vol. 6, pp. 226-233.

Eder et al.: "Transforming growth factor-beta1 and beta2 in serum and urine from patients with bladder carcinoma," The J. of Urology (1996) vol. 156, pp. 953-957.

Eskelinen et al.: "A new tumor marker MCA in breast cancer diagnosis," Anticancer Res. (1988), vol. 8, pp. 665-668.

Kaiser et al.: "Capillary electrophoresis coupled to mass spectrometer for automated and robust polypeptide determination in body fluids for clinical use," Electrophoresis (2004) V. 25, pp. 2044-2055.

Lecaptain et al.: "Characterization of DNA-protein complex by capillary electrophoresis-single molecule fluorescence correlation spectroscopy," Analyst (2001) vol. 126, pp. 1279-1284.

Panchuk-Voloshina et al.: "Alexa dyes, a series of new fluorescent dyes that yield exceptionally bright, phostotable conjugates," J. Histochem Cytochem (Sep. 1999) vol. 47, No. 9, pp. 1179-1188.

Schiffer et al.: "High resolution proteome/peptidome analysis of body fluids by capillary electrophoresis coupled with MS," Proteomics (2006) V. 6, pp. 5615-5627.

Von Zur Muhlen et al.: "Evaluation of Urine Proteome Pattern Analysis for Its Potential to Reflect Coronary Artery Atherosclerosis in Symptomatic Patients," J. Proteom. Res. (2009) V. 8, pp. 335-345.

Zimmerli et al.: in "Urinary Proteomic Biomakers in Coronary Artery Disease," Mol. Cell Proteomics (Feb. 2008), V. 7, No. 2, pp. 290-298. First Published on Oct. 19, 2007.

U.S. Appl. No. 60/613,881, entitled "Continuous wave single particle detector," filed Sep. 28, 2004, Puskas.

U.S. Appl. No. 60/624,785, entitled "Sandwich assay for detection of individual molecules," filed Oct. 29, 2004, Puskas.

U.S. Appl. No. 11/784,186, entitled "Methods and Compositions for Highly Sensitive Analysis of Markers," filed Apr. 4, 2007, Goix, Philippe J.

U.S. Appl. No. 12/060,997, entitled: "Methods and Compositions for Highly Sensitive Analysis of Markers," filed on Apr. 2, 2008, Goix, Philippe J. et al.

DeJong, et al., "Receptor-ligand binding assays: Technologies and Applications", Journal of Chromatography B: Biomedical Sciences & Applications, 829:1-25 (2005).

Piston, D., "Choosing Objective Lenses: The Importance of Numerical Aperture and Magnification in Digital Optical Microscopy", Bio9logical bulletin, 195:1-4 (1998).

Microscope Technical Info, Numerical Aperture (N.A..), Condenser lenses and immersion Oil; Microbus (2007).

Pupil Diameter and Beam Spot Diameter of Objective Lens; Olympus Corporation; Knowledge (2013).

Wang, et al., "Single-Molecule Tracing on a Fluidic microchip for Quantitative Detection of Low-Abundance Nucleic Acids", Journal of the American Chemical Society, 127:5354-5359 (2005).

Berlier, et al., "Quantitative Comparison of long-wavelength Alexa Fluor Dyes to Cy Dyes: Fluorescence of the Dyes and their Bioconjugates", The Journal of Histochemistry and Cytochemistry, 51:1699-1712 (2003).

Wilson, et al., "Validation of mitochondrial DNA sequencing for forensic casework analysis", Int. J. Legal Med., 108:68-74 (1995).

Laser output data sheet: 4 pages (2000).

Notice of Allowance mailed on Nov. 12, 2013 in U.S. Appl. No. 12/731,500, filed Mar. 25, 2010.

Borrebaeck, C., Antibody Engineering. Second Edition, Oxford University Press, Oxford, 1995, 11 pages.

(56) References Cited

OTHER PUBLICATIONS

Huse et al., Application of a filamentous phag pVIII fusion protein system suitable for efficient production, screening and mutageneis of F (ab)antibody fragments, J. Immunology, Dec. 15, 1992, vol. 149, No. 12, pp. 3914-3920.

Koerbin et al., the Comparative analytical performance of four troponin I assays at low concentration, Ann Clin. Biochem., 42:19-23 (2005).

Goix, Philippe J., U.S. Appl. No. 11/784,186, filed Apr. 4, 2007, 124 pages.

Goix, Philippe J., U.S. Appl. No. 12/060,997, filed Apr. 2, 2008, 167 pages.

Goodwin, et al., "Rapid sizing of individual fluorescently stained DNA fragments by flow cytometry", Nucleic Acids Research, 21:803-806 (1993).

Tahari, "Fluorescence Correlation Spectroscopy: Ultrasensitive Detection in Clear and Turbid Media", Dissertation, College of the University of Illinois at Urbana-Champaign, 2006.

Whatman 2004 Laboratory Products General Catalog.

Iwaki News, 2002.

Handbook of Optics, vol. 1, Second Edition, 1995, 3 pages.

Hori et al., "High Fidelity SNP Genotyping Using Sequence-Specific Primer Elongation and Fluorescence Correlation Spectroscopy"; Current Pharmaceutial Biotechnology, 2004, pp. 477-484, vol. 4.

Kawata et al,. "Three-dimensional optical-transfer-function analysis for a laser-scan fluorescence microscope with an extended detector"; J. Opt. Soc. Am. A., 1991, pp. 171-175, vol. 8.

Kobayashi et al., "Detection of protein-DNA interactions in crude cellular extracts by fluorescence correlation spectroscopy"; Analytical Biochemistry, 2004, pp. 58-66, vol. 332.

Whatman 2004 Laboratory Products General Catalog, 1 page.

\* cited by examiner

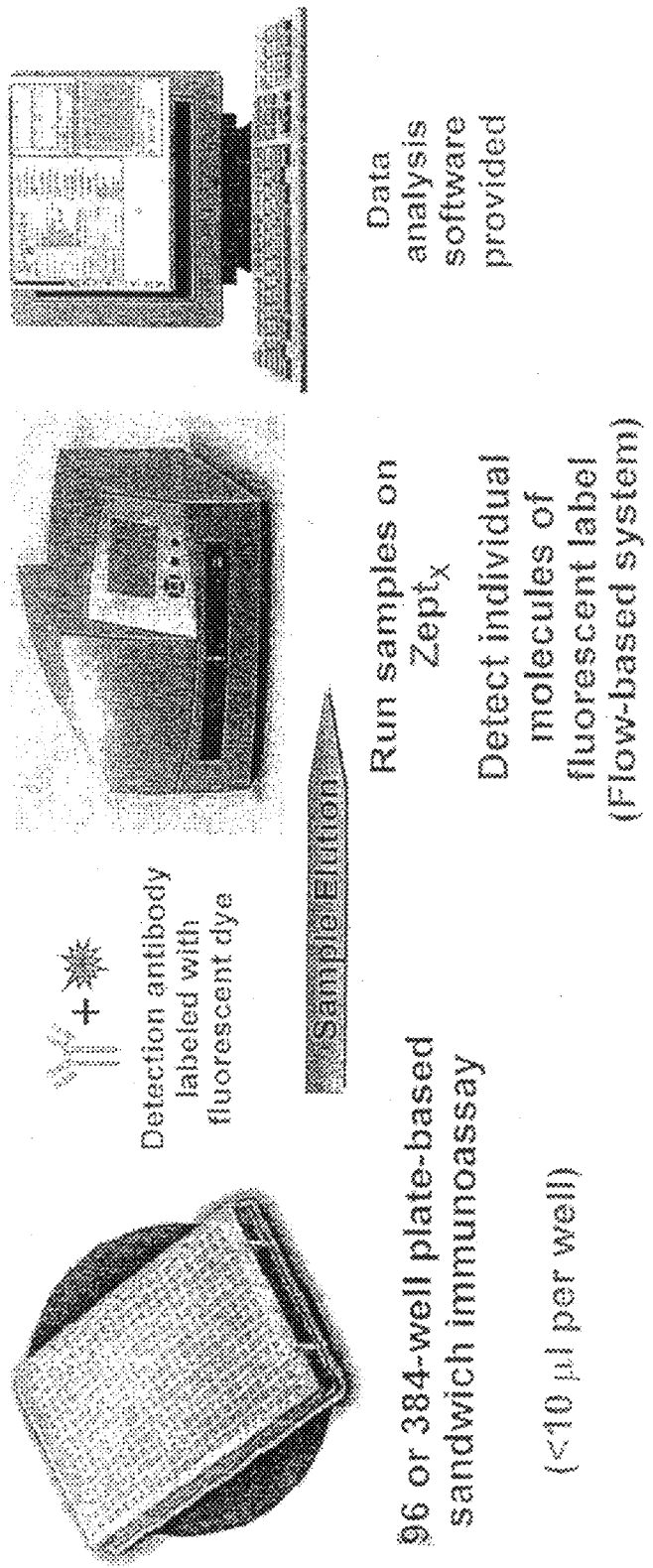

High sensitivity assays

| Cytokines | Molar Conc. | Molecules |
|---|---|---|
| IL-12 p70 | 2.02E-14 | 6.09E+05 |
| IL-10 | 5.36E-14 | 1.61E+06 |
| IL-1 alpha | 5.56E-14 | 1.67E+06 |
| IL-3 | 5.85E-14 | 1.76E+06 |
| IL-12 p40 | 6.07E-14 | 1.83E+06 |
| IL-1ra | 6.12E-14 | 1.84E+06 |
| IL-12 | 8.09E-14 | 2.44E+06 |
| IL-6 | 9.53E-14 | 2.87E+06 |
| IL-4 | 1.15E-13 | 3.47E+06 |
| IL-18 | 1.80E-13 | 5.43E+06 |
| IP-10 | 1.88E-13 | 1.13E+07 |
| IL-5 | 1.99E-13 | 5.98E+06 |
| Eotaxin | 2.06E-13 | 1.24E+07 |
| IL-16 | 3.77E-13 | 1.14E+07 |
| MIG | 3.83E-13 | 1.15E+07 |
| IL-8 | 4.56E-13 | 1.37E+07 |
| IL-17 | 5.18E-13 | 1.56E+07 |
| IL-7 | 5.97E-13 | 1.80E+07 |
| IL-15 | 6.13E-13 | 1.84E+07 |
| IL-13 | 8.46E-13 | 2.55E+07 |

| Cytokines | Molar Conc. | Molecules |
|---|---|---|
| IL-2R (soluble) | 8.89E-13 | 2.68E+07 |
| IL-2 | 8.94E-13 | 2.69E+07 |
| LIF/HILDA | 9.09E-13 | 5.47E+07 |
| IL-1 beta | 1.17E-12 | 3.51E+07 |
| Fas/CD95/Apo-1 | 1.53E-12 | 9.24E+07 |
| MCP-1 | 2.30E-12 | 6.92E+07 |

| Oncology | Molar Conc. | Molecules |
|---|---|---|
| EGF | 4.75E-14 | 2.86E+06 |
| TNF-alpha | 6.64E-14 | 8.00E+06 |
| PSA (3rd generation) | 1.15E-13 | 6.92E+06 |
| VEGF | 2.31E-13 | 6.97E+06 |
| TGF-beta1 | 2.42E-13 | 3.65E+07 |
| FGFb | 2.81E-13 | 1.69E+07 |
| TRAIL | 5.93E-13 | 3.57E+07 |
| TNF-RI (p55) | 2.17E-12 | 2.62E+08 |

Figure 14A

High sensitivity assays

| Inflammation | Molar Conc. | Molecules |
|---|---|---|
| ICAM-1 (soluble) | 8.67E-15 | 5.22E+04 |
| RANTES | 6.16E-14 | 3.71E+06 |
| MIP-2 | 9.92E-14 | 2.99E+06 |
| MIP-1 beta | 1.98E-13 | 5.97E+06 |
| MIP-1 alpha | 2.01E-13 | 6.05E+06 |
| MMP-3 | 1.75E-12 | 5.28E+07 |

| Endocrinology | Molar Conc. | Molecules |
|---|---|---|
| 17 beta-Estradiol (E2) | 4.69E-14 | 2.82E+06 |
| DHEA | 4.44E-13 | 2.67E+07 |
| ACTH | 1.32E-12 | 7.96E+07 |
| Gastrin | 2.19E-12 | 1.32E+08 |
| Growth Hormone (hGH) | 2.74E-12 | 1.65E+08 |

| Autoimmune | Molar Conc. | Molecules |
|---|---|---|
| GM-CSF | 1.35E-13 | 8.15E+06 |
| C-Reactive Protein (CRP) | 3.98E-13 | 2.40E+07 |
| G-CSF | 1.76E-12 | 1.06E+08 |

| Thyroid | Molar Conc. | Molecules |
|---|---|---|
| Cyclic AMP | 9.02E-15 | 5.43E+05 |
| Calcitonin | 3.25E-14 | 1.95E+06 |
| Parathyroid Hormone (PTH) | 1.56E-13 | 9.37E+06 |

| Cardiac | Molar Conc. | Molecules |
|---|---|---|
| B-Natriuretic Peptide | 2.86E-13 | 1.72E+07 |
| NT-proBNP | 2.86E-12 | 8.60E+07 |

| | Molar Conc. | Molecules |
|---|---|---|
| C-Reactive Protein, HS | 3.98E-13 | 2.40E+07 |
| Beta-Thromboglobulin (BTG) | 5.59E-13 | 3.36E+07 |

| Diabetes | Molar Conc. | Molecules |
|---|---|---|
| C-Peptide | 2.41E-15 | 1.45E+05 |
| Leptin | 1.89E-13 | 1.14E+07 |

| Infectious Dis. | Molar Conc. | Molecules |
|---|---|---|
| IFN-gamma | 2.08E-13 | 1.25E+07 |
| IFN-alpha | 4.55E-13 | 2.74E+07 |

| Metabolism | Molar Conc. | Molecules |
|---|---|---|
| Bio-Intact PTH (1-84) | 1.59E-12 | 1.44E+08 |
| PTH | 1.05E-13 | 9.51E+06 |

Figure 14B

Zero standard; replicates of 60; all other standards replicates of 10

US 9,040,305 B2

METHOD OF ANALYSIS FOR DETERMINING A SPECIFIC PROTEIN IN BLOOD SAMPLES USING FLUORESCENCE SPECTROMETRY

CROSS-REFERENCE

This application is a continuation-in-part application of Ser. No. 11/048,660, filed Jan. 28, 2005, which is incorporated herein by reference in its entirety and to which application we claim priority under 35 USC §120. Application Ser. No. 11/048,660 claims the benefit of U.S. Provisional Application No. 60/613,881, filed Sep. 28, 2004, U.S. Provisional Application No. 60/624,785, filed Oct. 29, 2004, and U.S. Provisional Application No. 60/636,158, filed Dec. 16, 2004.

This application also claims priority under 35 USC §119 to U.S. Provisional Application No. 60/861,498, filed Nov. 28, 2006, and U.S. Provisional Application No. 60/872,986, filed Dec. 4, 2006, all of which are incorporated herein by reference in their entirety.

BACKGROUND OF THE INVENTION

Advances in biomedical research, medical diagnosis, prognosis, monitoring and treatment selection, bioterrorism detection, and other fields involving the analysis of multiple samples of low volume and concentration of analytes have led to development of sample analysis systems capable of sensitively detecting particles in a sample at ever-decreasing concentrations. U.S. Pat. Nos. 4,793,705 and 5,209,834 describe previous systems in which extremely sensitive detection has been achieved. The present invention provides further development in this field.

SUMMARY OF THE INVENTION

The present invention provides a method of analysis for determining the presence or absence of a specific protein molecule in a blood sample obtained from an animal, comprising the steps of:

a) providing a processed sample, where the processed sample has been prepared by (i) extracting serum or plasma from the blood sample; (ii) contacting the serum or plasma with a selective capture agent specific for the protein molecule; (iii) adding a plurality of fluorescent labels specific for the protein molecule, where one of the fluorescent labels and the protein molecule associate to form a protein-label complex; (iv) removing fluorescent labels that have not associated with the protein molecule; (v) releasing the protein-label complex into solution or dissociating the fluorescent label from the protein-label complex so that the dissociated fluorescent label moves into solution;

b) sampling a portion of the processed sample, where the sampling is performed by a sampling system that (i) is capable of automatically and sequentially sampling a plurality of processed samples from a multiwell container; and (ii) comprises a source of negative pressure to draw the portion of the processed sample into a sampling port that is inserted into the processed sample, and a flow channel that provides a fluid communication between the sampling port and a detection channel of a single molecule analyzer, where the detection channel is substantially transparent to at least some wavelengths of light and provides a channel through which the portion of the processed sample may flow, and the analyzer comprises a laser for providing excitation light, where the light is within the wavelengths to which the detection channel is substantially transparent;

(c) passing the portion of the processed sample through the detection channel of the analyzer using positive or negative pressure;

(d) focusing the excitation light with a laser focuser on a portion of the detection channel, so that the light excites the fluorescent label if present in the portion of the detection channel so that the label produces emitted light;

(e) passing the emitted light through an aperture, so that the focusing of excitation light and passing of emitted light through the aperture define a molecule detection volume within the portion of the detection channel of between about 0.1 pL and about 25 pL;

(f) detecting the emitted light that has passed through the aperture with a detector, which transforms the light into an electronic signal; and (g) analyzing the electronic signal with a data analysis system operably connected to the detector that compares the signal to a threshold value to determine whether or not the fluorescent label is present in the molecule detection volume.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings:

FIG. 1A shows an analyzer that includes one electromagnetic source and one electromagnetic detector; FIG. 1B shows an analyzer that includes two electromagnetic sources and one electromagnetic detector.

FIG. 2A shows the flow cell of an analyzer that includes one electromagnetic source; and FIG. 2B shows the flow cell of an analyzer that includes two electromagnetic sources.

FIG. 3A shows the arrangement for an analyzer that has one electromagnetic source and one electromagnetic detector; FIG. 3B shows the arrangement for an analyzer that has two electromagnetic sources and two electromagnetic detectors.

FIG. 4: A schematic diagram of one embodiment of the method of the invention.

FIGS. 14A) and B): Markers of use in various conditions, and their limits of detection.

DETAILED DESCRIPTION OF THE INVENTION

Figure 1A:
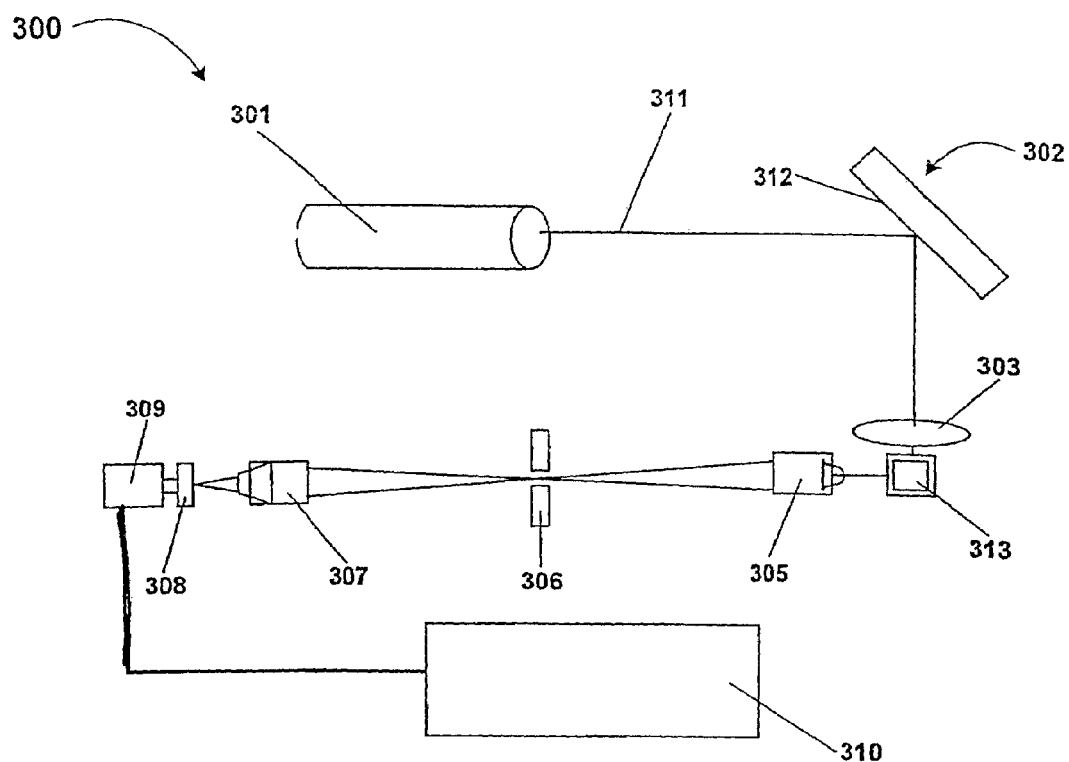
FIGS. 1A and 1B. Schematic diagram of the arrangement of the components of a single particle analyzer.

The present invention provides analyzers and analyzer systems, and methods of using the analyzers and analyzer system, for ultra-sensitive detection, quantitation and discrimination of particles at very low concentrations.

In particular, the present invention provides a method of analysis for determining the presence or absence of a specific protein molecule in a blood sample obtained from an animal, comprising the steps of:

a) providing a processed sample, where the processed sample has been prepared by (i) extracting serum or plasma from the blood sample; (ii) contacting the serum or plasma with a selective capture agent specific for the protein molecule; (iii) adding a plurality of fluorescent labels specific for the protein molecule, where one of the fluorescent labels and the protein molecule associate to form a protein-label complex; (iv) removing fluorescent labels that have not associated with the protein molecule; (v) releasing the protein-label complex into solution or dissociating the fluorescent label from the protein-label complex so that the dissociated fluorescent label moves into solution;

b) sampling a portion of the processed sample, where the sampling is performed by a sampling system that (i) is capable of automatically and sequentially sampling a plurality of processed samples from a multiwell container; and (ii) comprises a source of negative pressure to draw the portion of the processed sample into a sampling port that is inserted into the processed sample, and a flow channel that provides a fluid communication between the sampling port and a detection channel of a single molecule analyzer, where the detection channel is substantially transparent to at least some wavelengths of light and provides a channel through which the portion of the processed sample may flow, and the analyzer comprises a laser for providing excitation light, where the light is within the wavelengths to which the detection channel is substantially transparent;

(c) passing the portion of the processed sample through the detection channel of the analyzer using positive or negative pressure;

(d) focusing the excitation light with a laser focuser on a portion of the detection channel, so that the light excites the fluorescent label if present in the portion of the detection channel so that the label produces emitted light;

(e) passing the emitted light through an aperture, so that the focusing of excitation light and passing of emitted light through the aperture define a molecule detection volume within the portion of the detection channel of between about 0.1 pL and about 25 pL;

(f) detecting the emitted light that has passed through the aperture with a detector, which transforms the light into an electronic signal; and (g) analyzing the electronic signal with a data analysis system operably connected to the detector that compares the signal to a threshold value to determine whether or not the fluorescent label is present in the molecule detection volume.

The above embodiment is described in detail below. Further description and embodiments are also provided herein.

The sample to be analyzed may be obtained from any suitable animal, e.g., mammal. In some embodiments the animal is a human. Although a variety of sample types may be analyzed, as described elsewhere herein, in this embodiment the sample type is a blood sample. The protein molecule to be detected may be any protein molecule whose presence or absence is desired to be determined, as described elsewhere herein. In particular embodiments, the protein molecule may be any one of, e.g., IL-1 beta, TNF-alpha, IL-6, cardiac Troponin I, IL-8, Abeta 40, FGF-basic, IL-1 alpha, IL-7, MCP-1, Abeta 42, GM-CSF, IL-2, IL-12, MIP-1a, IFN-alpha, IL-4, IL-13, RANTES, Fas ligand, IFN-gamma, IL-5, IL-17, or VEGF. Other protein molecules are as described herein (see, e.g., "Markers," below).

The blood sample is further processed to provide a processed sample, which is run through the analyzer. The sample is first treated to provide serum or plasma, e.g., by clotting (serum) and/or centrifugation, as well-known in the art. The serum or plasma is then subjected to a sandwich assay in which the serum or plasma is contacted with a capture agent, e.g., an antibody such as a polyclonal or monoclonal antibody, which is specific for the protein molecule suspected to be present in the sample. Such capture agents are well-known and are described elsewhere herein. The capture agent is typically attached to a solid support, such as a microtiter plate or beads (e.g., paramagnetic beads), also described further herein. Optionally, a wash step is performed to remove non-attached materials.

A plurality of fluorescent labels specific for the protein molecule is then added, where one of the labels and the protein molecule associate to form a protein-label complex. The fluorescent label may be any suitable label that both is able to specifically bind to the protein molecule of interest and that provides sufficient intensity of fluorescence in the analyzer system of the invention to be detected. One such label is an antibody-fluorescent moiety complex, e.g., a detection antibody such as a monoclonal antibody specific for the protein molecule to which is attached one or more dye molecules or other fluorescent moieties of sufficient fluorescence to be detected by the system above background noise. See, e.g., FIG. 4. Any suitable method of attachment may be used, e.g., covalent or noncovalent attachment (such as avidin/streptavidin-biotin interaction); methods for attachment of fluorescent moieties to binding molecules, e.g., antibodies, are known in the art. It will be appreciated that labeling may also be indirect, e.g., a first detection antibody specific for the protein molecule may be added and allowed to bind, excess first antibody removed, then a secondary antibody specific for the first antibody may be added, where the secondary antibody is the labeled antibody.

Suitable dye molecules and other fluorescent moieties for use in the fluorescent label are as described herein. Especially useful are the AlexaFluor molecules, e.g., AlexaFluor 647, as described in the Examples. These dye molecules include at least one substituted indolium ring system in which the substituent on the 3-carbon of the indolium ring contains a chemically reactive group or a conjugated substance. Other suitable AlexaFluor molecules include AlexaFluor 488, AlexaFluor 532, AlexaFluor 680 or AlexaFluor 700. Thus, some embodiments utilize a fluorescent label that includes an antibody to the protein molecule of interest to which is attached one or more, e.g., an average of 2-4 or 2-5 or 2-6, AlexaFluor molecules, such as AlexaFluor 488, AlexaFluor 532, AlexaFluor 647, AlexaFluor 680 or AlexaFluor 700. Other suitable fluorescent moieties include quantum dots. However, any fluorescent moiety may be used that is capable of being specifically bound to the protein molecule of interest (e.g., as attached to an antibody specific for the protein molecule of interest), that fluoresces sufficiently to be detected, and that does not cause undue aggregation.

Unbound fluorescent label is removed, e.g., by washing. It will be appreciated that the binding of the protein molecule to capture agent and binding of fluorescent label to protein molecule may be done sequentially or simultaneously. Thus, in some embodiments capture of the protein molecule is followed by addition of label, whereas in other embodiments, the two steps are simultaneous, or nearly simultaneous. In either embodiment, removal of unbound label, e.g., by washing, is then performed.

The fluorescent label is then released into solution. See, e.g., FIG. 4. Either the protein-label complex may be released from the capture agent, or the fluorescent label may be released from the protein-label complex so that dissociated label moves into solution. Any suitable method of releasing label may be used, e.g., the use of an elution buffer. Useful properties of elution buffers include ability to dissociate protein-protein complexes (e.g., chaotropic agents such as urea), proper pH (such as a borate buffer), low fluorescence so as not to substantially interfere with fluorescence of the fluorescent label, and agents that mitigate against binding of proteins to components of the analyzer system and aggregation of proteins (e.g., detergents). One such elution buffer that surprisingly has been found to have low fluorescence despite its high urea content includes 1-40 mM borate at pH 8.1-8.5, 50-250 mM NaCl, 1-4 M urea, 0.01-0.04% Triton X-100, and 0.0005-0.002% BSA, e.g., 10 mM borate (pH 8.3), 150 mM NaCl, 4 M urea, 0.02% Triton X-100, and 0.001% BSA.

The processed sample is then sampled into the analyzer with a sampling system. The sampling system includes a mechanism for obtaining processed sample from a multiwell container, such as a microtiter plate (FIG. 4), and source of negative pressure (e.g., a pump) to draw a portion of the processed sample into the sampling port of the sampler, and to pass the portion of the processed sample through a flow channel that connects the port with a detection channel of a single molecule analyzer. The sampling port and flow channel may be, e.g., tubing such as capillary tubing. Suitable tubing, pumps, multiwell containers, and the like are described elsewhere herein. The portion of the processed sample pulled up by the sampling system may be any suitable volume, depending on desired duration of analysis (e.g., larger samples will require longer analysis time as they take longer to flow through the detection volume), likely concentration of the protein molecule of interest, and the like. Volumes may be 0.1-1000 ul, or 1-100 ul, or 1-50 ul, or 1-10 ul, or 1, 2, 3, 4, 5, 6, 7 8, 9, or 10 ul. In some embodiments, the volume sampled is 5 ul.

The portion of the processed sample that has been sampled by the automatic sampler is then passed through a single molecule analyzer capable of detecting the fluorescent label (FIG. 4). The sample is moved by positive or negative pressure, supplied by, e.g., a pump as described herein. The single molecule analyzer includes a detection channel that is fluidly connected to the sampling system, where the detection channel is substantially transparent to at least some wavelengths of light; a laser for providing excitation light to excite the fluorescent label, where the light is within the wavelengths to which the detection channel is substantially transparent; a laser focuser for focusing the laser on a portion of the detection channel, where it excites the fluorescent label, if present, to emit light; an aperture through which the emitted light passes, where the focuser and the aperture serve to define a molecule detection space within the portion of the detection channel; and a detector for detecting the emitted light that passes through the aperture and transforming it into an electronic signal.

The detection channel may be any suitable material that allows light of the desired wavelengths to pass and that allows the portion of the processed sample to flow through, e.g., a capillary tube of glass, quartz, or other suitable substance. In some embodiments the invention utilizes a fused silica capillary of about 100 micron square ID and about 300 micron square OD as a detection channel. The laser is situated so as to provide light to the detection channel at the desired location. Any suitable laser may be used that provides light at the excitation wavelength of the fluorescent label at sufficient intensity and for sufficient duration to excite the fluorescent label to emit sufficient photons to be detected and distinguished from background fluorescence, e.g., a continuous wave laser. One such laser that provides light at wavelengths suitable for use with, e.g., AlexaFluor 647 is a gallium arsenite diode laser of wavelength 639 nm (Blue Sky Research, Milpitas, Calif.). Other lasers may be used as appropriate and as described herein. A laser focuser, e.g., a lens, is used to focus the beam of the laser onto the detection channel, where it excites the fluorescent label, if present. Light emitted from the fluorescent label is passed through an aperture; together, the focuser and the aperture serve to define a molecule detection volume (also referred to herein as an "interrogation space") for detecting the fluorescent label. The detection volume is small enough that only one fluorescent label is likely to be in the volume during one detection period, but large enough that even in highly dilute samples a sufficient number of labels will flow through the detection volume within successive detection periods to allow quantitation of concentration. It will be appreciated that the detection volume can depend on the concentration of the protein molecule in the original sample, among other factors. The detection volume is between about 0.1 pL and about 25 pL. In other embodiments, the detection volumes that may be used in include volumes between about 0.004 pL and about 100 pL, or about 004 pL and about 50 pL, or about 0.004 pL and about 25 pL, or about 0.004 pL and about 10 pL or about 0.01 pL and about 25 pL. Further detection volumes are as described herein.

Further components of the single molecule analyzer typically include a microscope objective lens that collects light emitted from the fluorescent label and forms an image of the beam onto the aperture, a detection lens that focuses light that passes through the aperture onto an active area of the detector, and detector filters that minimize aberrant noise signals due to light scatter or ambient light while maximizing the signal emitted by the excited fluorescent label. The microscope objective lens may be a high numerical aperture lens, e.g., a lens of numerical aperture of at least about 0.8.

An example of a single molecule analyzer for use in the present embodiment is shown in FIG. 1A. The analyzer system 300 includes an electromagnetic radiation source 301, a mirror 302, a lens (laser focuser) 303, a capillary flow cell (detection channel) 313, a microscopic objective lens 305, an aperture 306, a detector lens 307, a detector filter 308, a single photon detector 309, and a processor 310 operatively connected to the detector.

In operation the electromagnetic radiation source 301 is aligned so that its output 311 is reflected off of a front surface 312 of mirror 302. The lens 303 focuses the beam 311 onto a portion of the capillary flow cell 313. The microscope objective lens 305 collects light from fluorescent label and forms an image of the beam onto the aperture 306. The aperture 306 affects the fraction of light emitted by the specimen in the capillary flow cell 313 that can be collected. The detector lens 307 collects the light passing through the aperture 306 and focuses the light onto an active area of the detector 309 after it passes through the detector filters 308. The detector filters 308 minimize aberrant noise signals due to light scatter or ambient light while maximizing the signal emitted by the excited fluorescent label. The processor 310 processes the light signal from the particle according to the methods described herein.

Figure 1B:
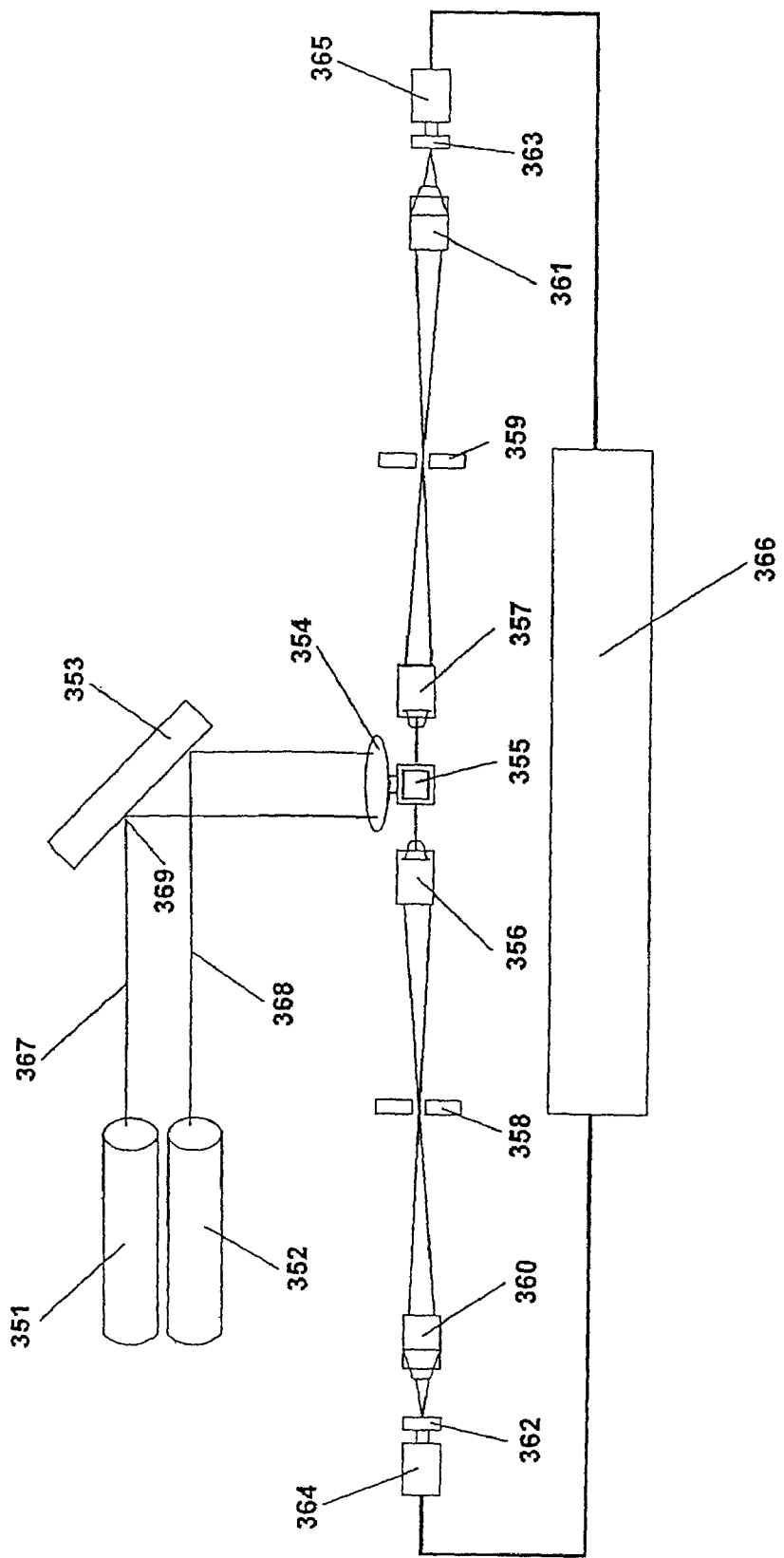

In some embodiments, the optics of the electromagnetic radiation source 301 and the optics of the detector 309 are arranged in a conventional optical arrangement. In such an arrangement, the electromagnetic radiation source and the detector are aligned on different focal planes. The arrangement of the laser and the detector optics of the analyzer system as shown in FIGS. 1A and 1B is that of a conventional optical arrangement.

Figure 2A:
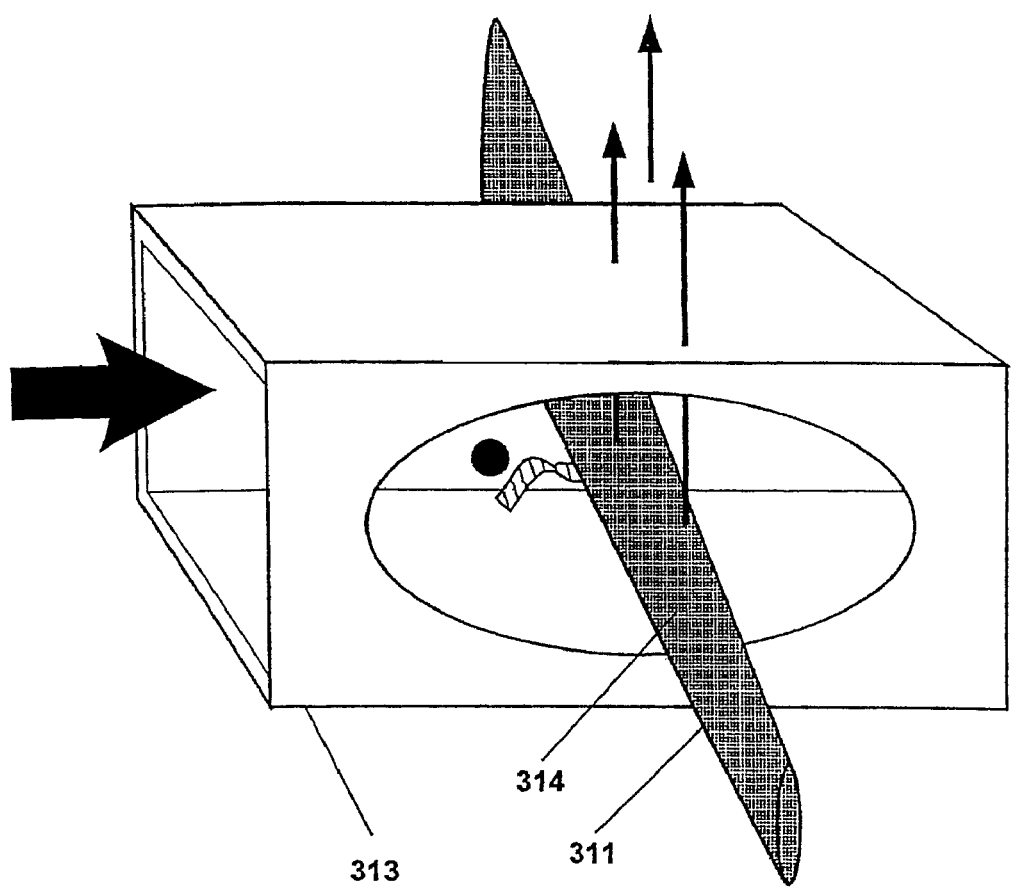
FIGS. 2A and 2B. Schematic diagrams of a capillary flow cell for a single particle analyzer.
Figure 2B:
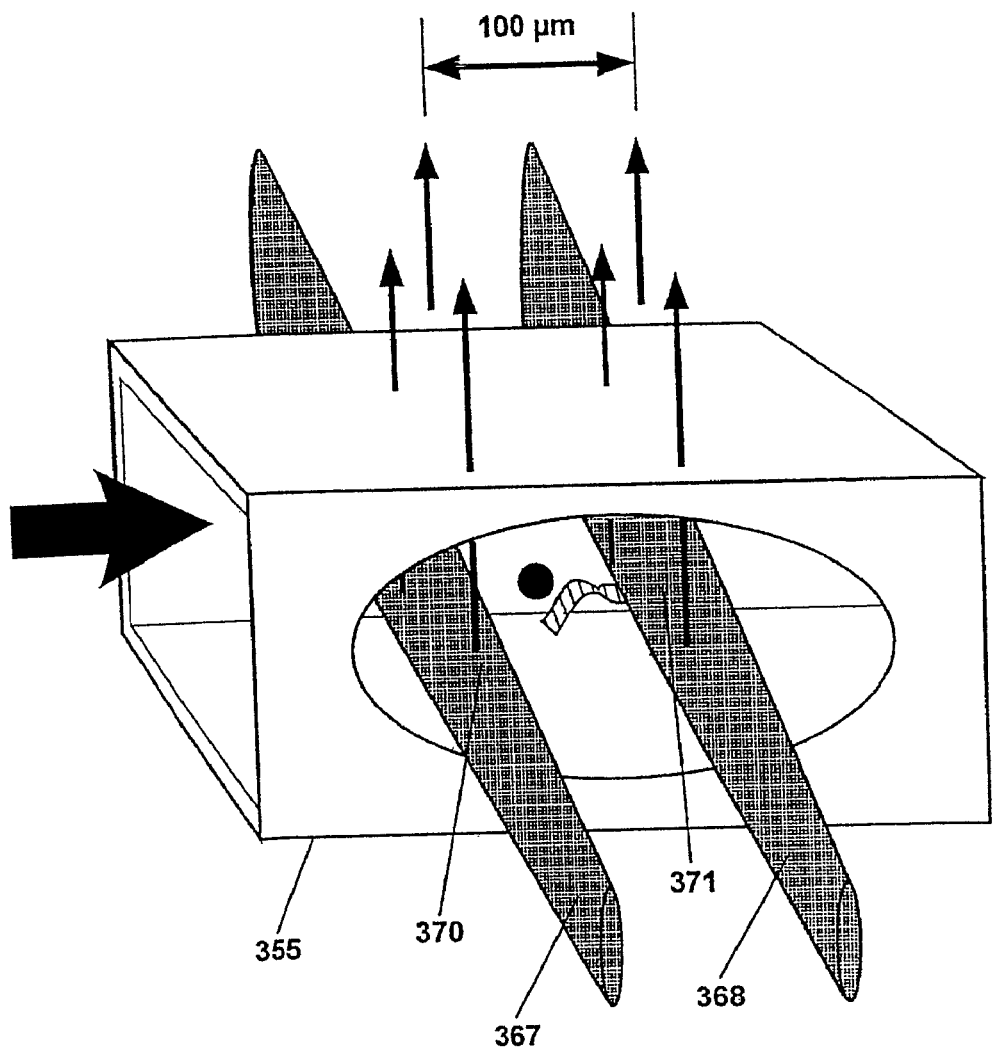
Figure 3A:
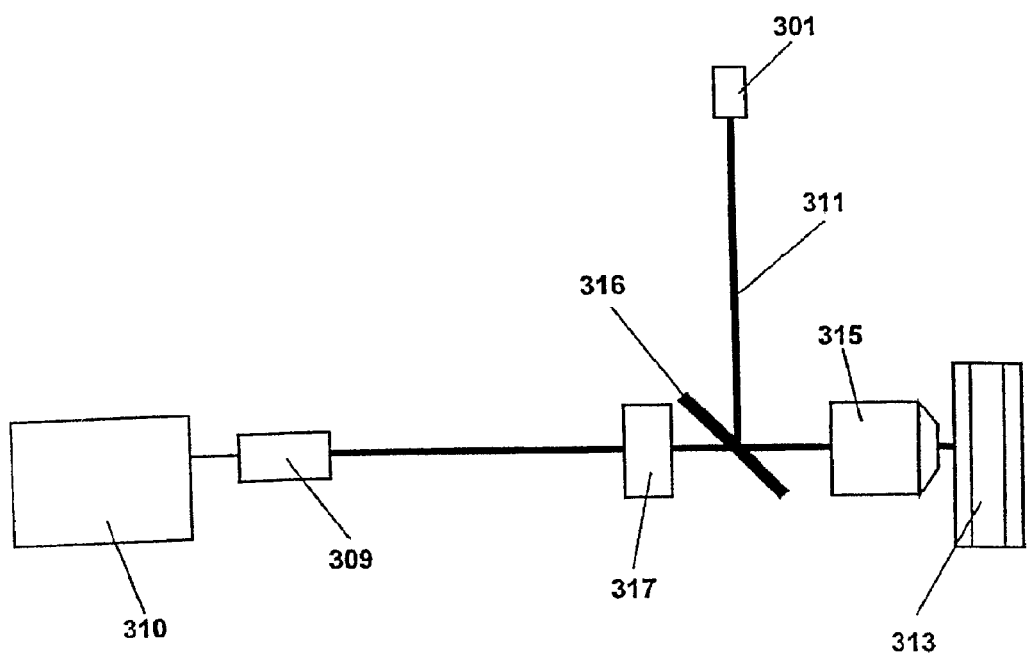
FIGS. 3A and 3B. Schematic diagrams showing the confocal positioning of laser and detector optics of a single particle analyzer.
Figure 3B:
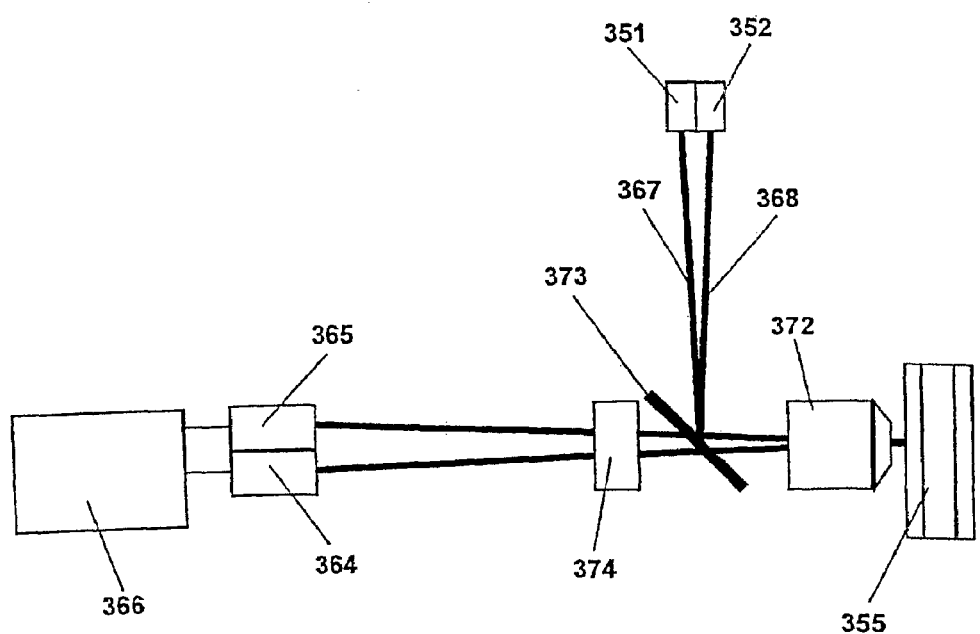

In some embodiments, the optics of the electromagnetic radiation source and the optics of the detector are arranged in a confocal optical arrangement. In such an arrangement, the electromagnetic radiation source 301 and the detector 309 are aligned on the same focal plane. The confocal arrangement renders the analyzer more robust because the electromagnetic radiation source 301 and the detector optics 309 do not need to be realigned if the analyzer system is moved. This arrangement also makes the use of the analyzer more simplified because it eliminates the need to realign the components of the analyzer system. The confocal arrangement for the analyzer 300 (FIG. 1A) and the analyzer 355 (FIG. 1B) are shown in FIGS. 3A and 3B respectively. FIG. 3A shows that the beam 311 from an electromagnetic radiation source 301 is focused by the microscope objective 315 to form one focused spot 314 (FIG. 2A) within the capillary flow cell 313. A dichroic mirror 316, which reflects laser light but passes fluorescent light, is used to separate the fluorescent light from the laser light. Filter 317 that is positioned in front of the detector eliminates any non-fluorescent light at the detector. In some embodiments, an analyzer system configured in a nonconfocal or confocal arrangement can comprise two or more interrogations spaces. Such analyzers and methods have been previously disclosed and are incorporated by reference from previous U.S. patent application Ser. No. 11/048,660.

The detector converts light energy emitted within the molecule to detection volume, e.g., light energy emitted by the fluorescent label, into an electronic signal. Any suitable detector may be used, e.g., an avalanche photodiode detector. Other detectors are described herein.

The electronic signal is then analyzed with a data analysis system operably connected to the detector. See, e.g., FIG. 4. The data analysis system compares the signal from the molecule detection volume with a threshold value. If the signal is above the threshold value, then the data analysis system registers that a fluorescent label is present in the molecule detection system. If the signal is not above the threshold value, the data analysis system does not register that a label is present. The data analysis system is typically a computer.

In general, the processed sample flowing through the detection volume is effectively divided into a series of detection events, by subjecting a given molecule detection volume of the detection channel to light from a laser that emits light at an appropriate excitation wavelength for the fluorescent label used for a predetermined period of time, and detecting photons emitted during that time. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. Typically, processed sample concentration is dilute enough that, for a large percentage of detection events, the detection event represents only one label passing through the detection volume, that is, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant. See, e.g., FIG. 5B.

Although other bin times may be used without departing from the scope of the present invention, in some embodiments the bin times are selected in the range of about 1 microsecond to about 5 ms. In some embodiments, the bin time is about 1 to 1000 microseconds. In some embodiments, the bin time is about 1 to 100 microseconds. In some embodiments, the bin time is about 10, 20, 30, 40, 50, 60, 70, 80, 90, 100, 150, 200, 250, 300, 400, 500, 750, or 1000 microsecond. Further bin times are as described herein.

The background noise level may be determined from the mean noise level, or the root-mean-square noise. In other cases, a typical noise value or a statistical value is chosen. In most cases, the noise is expected to follow a Poisson distribution.

Thus, as a label flows through the capillary flow cell, it is irradiated by the laser beam to generate a burst of photons.

The photons emitted by the label are discriminated from background light or background noise emission by considering only the bursts of photons that have energy above a predetermined threshold energy level which accounts for the amount of background noise that is present in the sample. Background noise typically comprises low frequency emission produced, for example, by the intrinsic fluorescence of non-labeled particles that are present in the sample, the buffer or diluent used in preparing the sample for analysis, Raman scattering and electronic noise. In some embodiments, the value assigned to the background noise is calculated as the average background signal noise detected in a plurality of bins, which are measurements of photon signals that are detected in an detection volume during a predetermined length of time. Thus in some embodiments, background noise is calculated for each sample as a number specific to that sample.

Given the value for the background noise, the threshold energy level can be assigned. As discussed above, the threshold value is determined to discriminate true signals (due to fluorescence of a label) from the background noise. Care must be taken in choosing a threshold value such that the number of false positive signals from random noise is minimized while the number of true signals which are rejected is also minimized. Methods for choosing a threshold value include determining a fixed value above the noise level and calculating a threshold value based on the distribution of the noise signal. In one embodiment, the threshold is set at a fixed number of standard deviations above the background level. Assuming a Poisson distribution of the noise, using this method one can estimate the number of false positive signals over the time course of the experiment. In some embodiments, the threshold level is calculated as a value of 4 sigma above the background noise. For example, given an average background noise level of 200 photons, the analyzer system establishes a threshold level of $4\sqrt{200}$ above the average background/noise level of 200 photons to be 256 photons Many bin measurements are taken to determine the concentration of a sample, and the absence or presence of a label is ascertained for each bin measurement. Typically, 60,000 measurements or more can made in one minute (e.g., in embodiments in which the bin size is 1 ms—for smaller bin sizes the number of measurements is correspondingly larger, e.g., 6,000,000 measurements per minute for a bin size of 10 microseconds). Thus, no single measurement is crucial and the method provides for a high margin of error. The bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements.

Figure 5A:
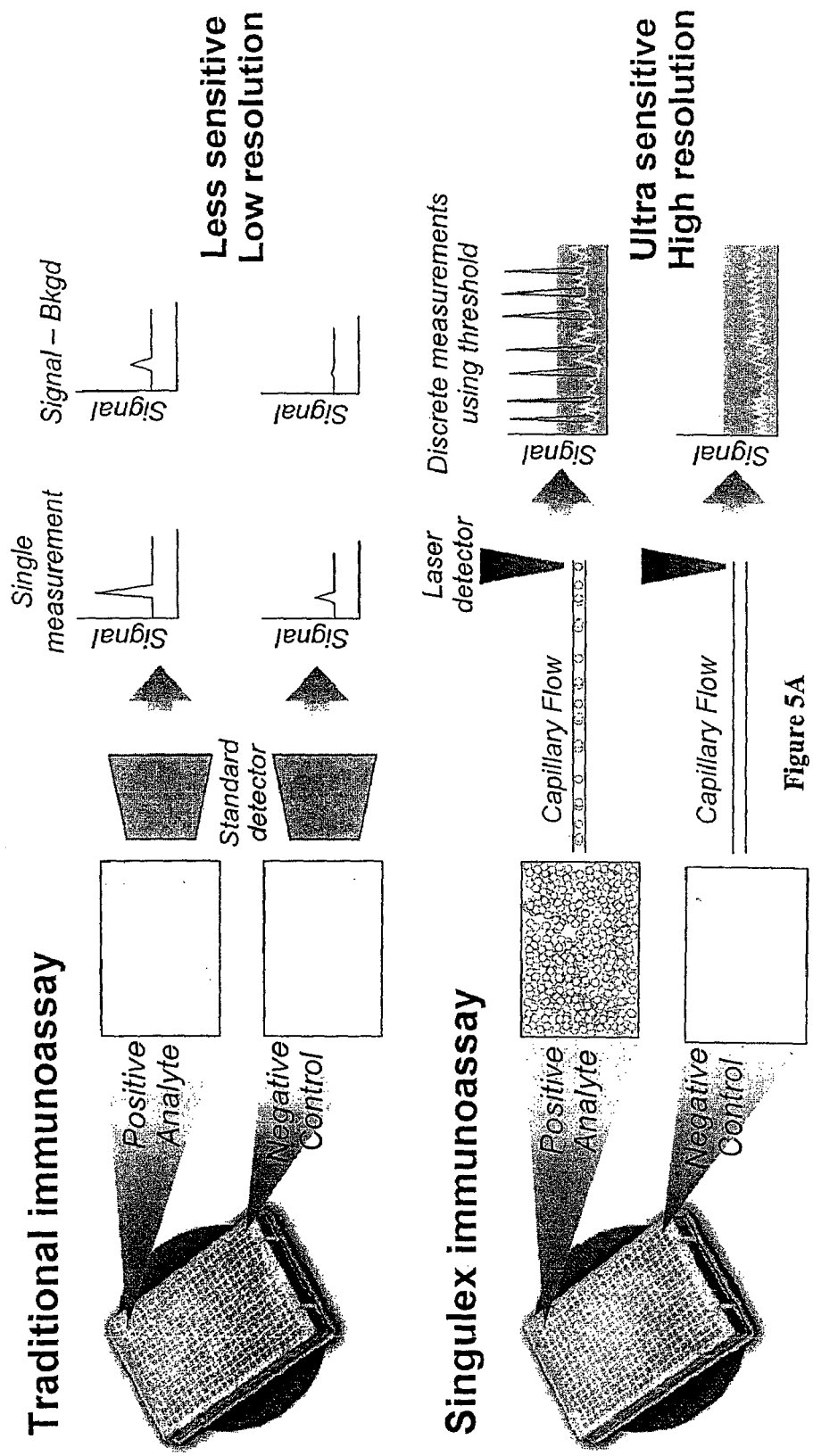
FIGS. 5A and 5B. A) An illustration illustrating the differences between a traditional immunoassay and the method of the invention. B) Enhancement of dynamic range by including an analog signal.
Figure 5B:
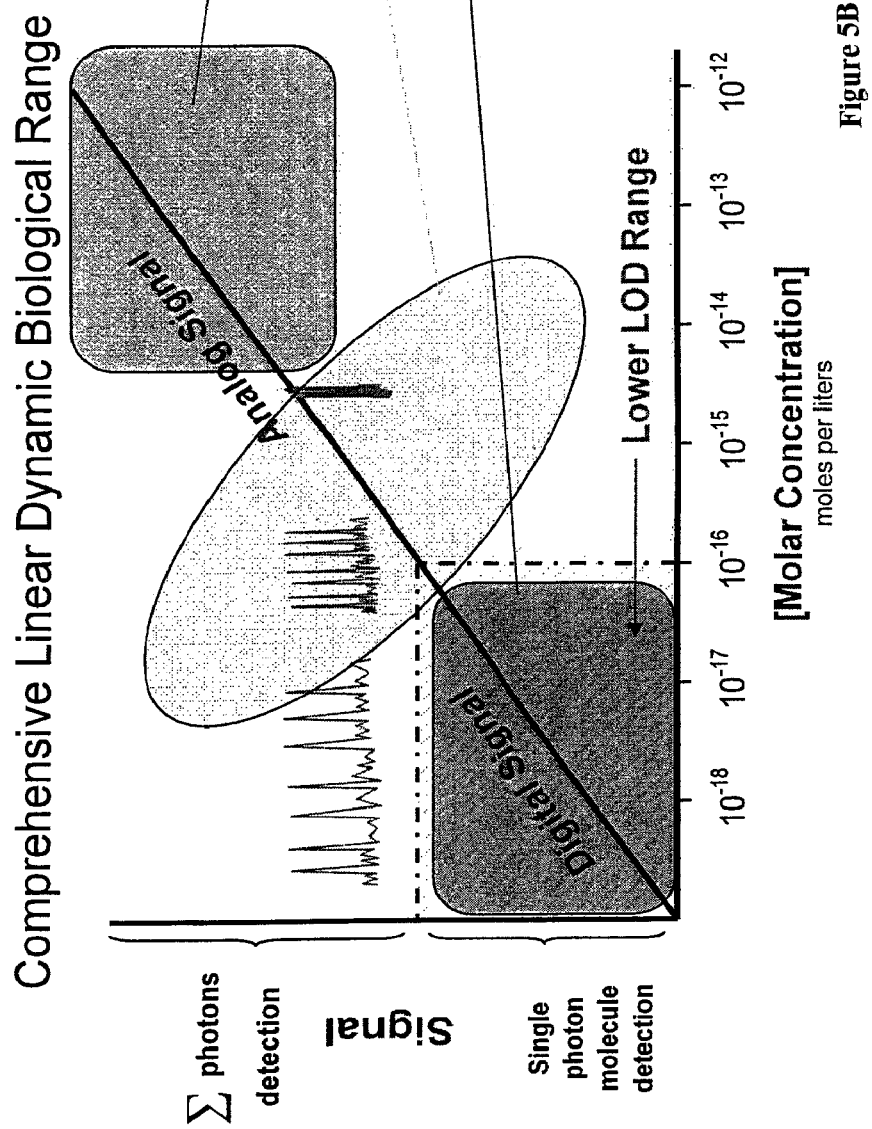

The difference between this approach and the traditional immunoassay approach is illustrated in FIG. 5. Rather than reading total fluorescence from a single sample, e.g., a well of a microtiter plate as in the traditional immunoassay (an "analog signal," top panel, FIG. 5A), the present embodiment splits the sample into hundreds, thousands, or millions of bins, each one of which is queried for the presence of label (a plurality of "digital signals," bottom panel, FIG. 5A). Since label typically is selected to fluoresce well above background fluorescence, each label will cause a "yes" answer in its window, greatly amplifying the signal-to-noise ratio and, thus, the level of sensitivity of the assay. Thus, in some embodiments, determining the concentration of a label in a sample comprises detecting the bin measurements that reflect the presence of a label.

It is also possible in some embodiments to combine digital signal at low concentrations with analog signal at higher concentrations to improve the dynamic range of the system. See, e.g., FIG. 5B.

The signal to noise ratio or the sensitivity of the analyzer system can be increased by minimizing the time that background noise is detected during a bin measurement in which a particle-label complex is detected. For example, in a bin measurement lasting 1 millisecond during which one particle-label complex is detected when passing across an interrogation space within 250 microseconds, 750 microseconds of the 1 millisecond are spent detecting background noise emission. The signal to noise ratio can be improved by decreasing the bin time. In some embodiments, the bin time is 1 millisecond. In other embodiments, the bin time is 750, 500, 250 microseconds, 100 microseconds, 50 microseconds, 25 microseconds or 10 microseconds. Other bin times are as described herein.

Other factors that affect measurements are the brightness or dimness of the fluorescent moiety, the flow rate, and the power of the laser. Various combinations of the relevant factors that allow for detection of label will be apparent to those of skill in the art. In some embodiments, the bin time is adjusted without changing the flow rate. It will be appreciated by those of skill in the art that as bin time decreases, laser power output directed at the interrogation space must increase to maintain a constant total energy applied to the interrogation space during the bin time. For example, if bin time is decreased from 1000 microseconds to 250 microseconds, as a first approximation, laser power output must be increased approximately four-fold. These settings allow for the detection of the same number of photons in a 250 μs as the number of photons counted during the 1000 μs given the previous settings, and allow for faster analysis of sample with lower backgrounds and thus greater sensitivity. In addition, flow rates may be adjusted in order to speed processing of sample. These numbers are merely exemplary, and the skilled practitioner can adjust the parameters as necessary to achieve the desired result.

Illustrations of the method of the invention are given in the Examples.

Further Embodiments and Description of the Invention

Figure 6:
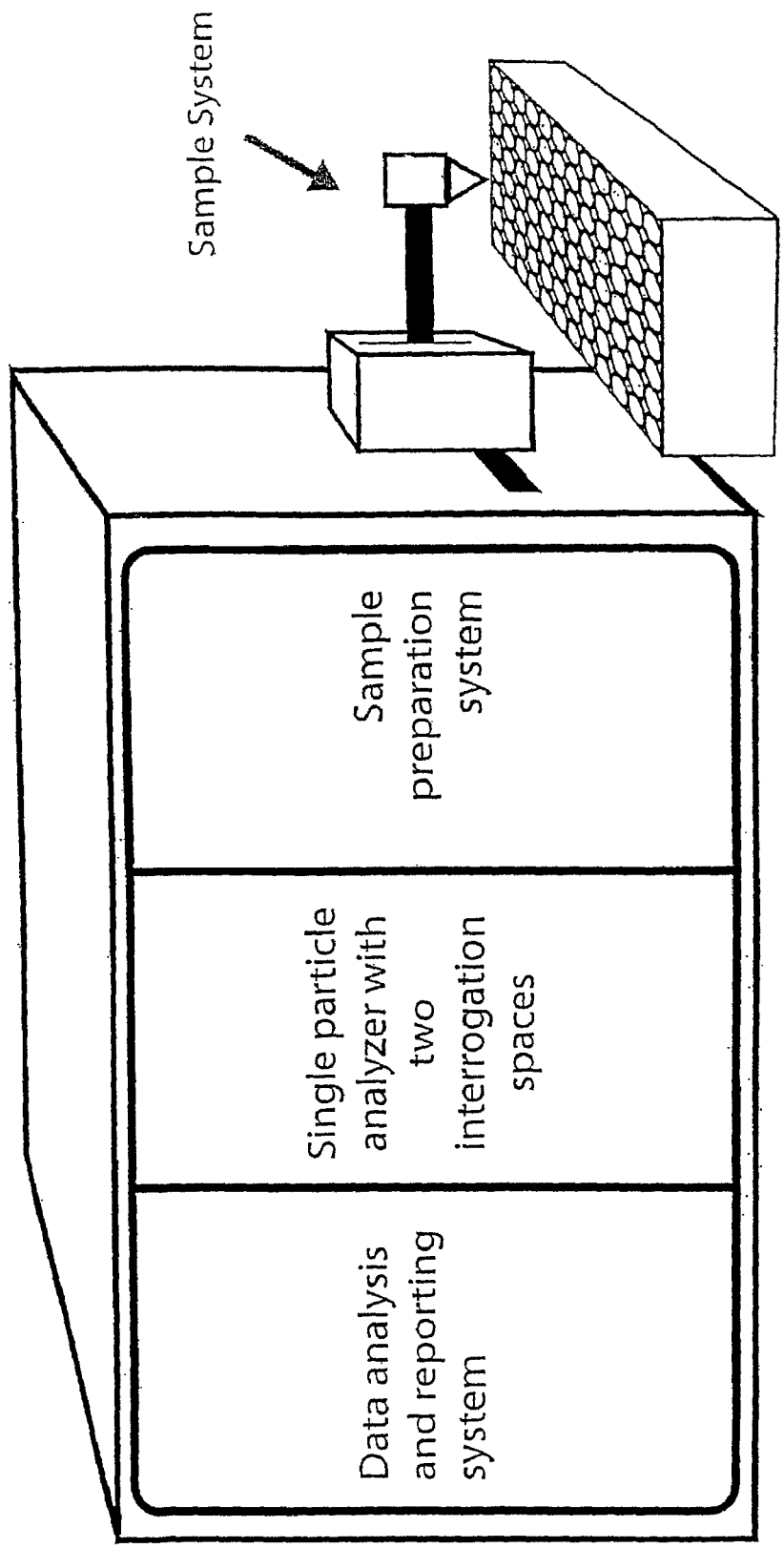
FIG. 6. Schematic diagram of one embodiment of a sample analysis system of the invention. The diagram indicates two interrogation spaces; however, one interrogation space is included in the invention.

A further embodiment of an analyzer system of the present invention is illustrated in FIG. 6. The illustrated system includes a sampling system capable of automatically sampling a plurality of samples and providing a fluid communication between a sample container and a first interrogation space; optionally, a sample preparation system; an analyzer capable of detecting a single particle, where the analyzer contains the first interrogation space and a second interrogation space through which the sample passes, and which are positioned to receive electromagnetic (EM) radiation from an EM radiation source, and which are operably connected to separate electromagnetic radiation detectors; and a data analysis and reporting system.

The analyzers of the invention are small, durable and accurate for the detection of single particles (e.g., protein molecules), interactions between individual particles and events involving single particles or particle complexes. The analyzer, analyzer system, and related methods provide the capability to distinguish at least one particle in a sample comprising multiple particles. In addition, the analyzer, analyzer system, and related methods provide for the improved detection of multiple target particles or multiple identifiable characteristics of one or more target particles in a single sample.

The embodiments described herein, by way of example, electromagnetic radiation as a means of particle detection. Within the field of single particle detection, optical-based detection systems (i.e., laser-induced fluorescence) are generally available and well-known to those of skill in the art. However, it is understood that other methods of particle detection, e.g., the use of chemiluminescent or radioactive tags and the like, where electromagnetic radiation is not required to be provided to the sample, but only detected, are also within the scope of the invention.

Apparatus/System

In one aspect, the invention provides an analyzer capable of detecting individual particles in a sample, where the particles are moved through the analyzer by a motive force. One embodiment of the analyzer is described above, utilizing a single detection window (interrogation space). In additional embodiments the analyzer comprises a single particle detection instrument that uses continuous wavelength (CW) lasers as a source of EM radiation, and that contains two fluidly-connected interrogation spaces, where pressure is used to move the sample through the interrogation spaces.

In another aspect, the invention provides an analyzer system. In some embodiments, the system includes an analyzer capable of detecting a single particle (e.g., a single molecule), where the detection instrument contains one interrogation space fluidly connected to a sampling system for introducing samples into the analyzer, an electromagnetic radiation source for emitting electromagnetic radiation, where the interrogation space is positioned to receive EM radiation emitted from the radiation source, and a first radiation detector operably connected to the first interrogation space to measure a first electromagnetic characteristic of the particle (e.g., molecule). In some embodiments the system includes an analyzer capable of detecting a single particle (e.g., a single molecule), where the detection instrument contains two fluidly connected interrogation spaces and a sampling system for introducing samples into the analyzer. In preferred embodiments the sampling system is an automated sampling system capable of sampling a plurality of samples without intervention from a human operator. In some embodiments the system further includes a sample recovery mechanism whereby a portion, or substantially all, of the sample may be recovered after analysis. In some embodiments the system further provides a sample preparation mechanism where a sample may be partially or completely prepared for analysis by the single particle analyzer. In some embodiments, the system further provides a computer for controlling the analysis and/or analyzing raw data and, in further embodiments, a reporting device for reporting the results of this analysis.

Samples and Particles

The invention provides analyzers and analyzer systems for highly sensitive, robust, and reproducible analysis of a wide variety of samples and the particles that may be contained within the samples. The invention provides methods of the detection of the presence, absence, and/or concentration of the particles.

Samples

Any sample that is capable of being moved through the interrogation spaces of the system, with or without processing, and that contains or may contain particles capable of detection by the detectors of the system, may be analyzed by the single particle analyzer or analyzer system of the invention. These include but are not limited to samples from industrial applications, environmental samples, agricultural samples, bioterrorism samples, samples for medical screening, diagnosis, prognosis or treatment, and samples from biomedical or other research, such as clinical or preclinical trials. Samples may be from in vitro or in vivo sources, or a combination thereof. The system is especially useful for the analysis of clinical samples for biomedical research, diagnosis or treatment.

Assays, for example as described in the Examples below, may be carried out using methods of the invention in a biological sample, e.g., a biological fluid. Such fluids include, without limitation, bronchoalveolar lavage fluid (BAL), blood, serum, plasma, urine, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest.

In some embodiments, the sample is a blood sample. In some embodiments the sample is a serum or plasma sample. In some embodiments, the sample is a bronchoalveolar lavage (BAL) sample. In some embodiments, the sample, e.g., a blood, serum or plasma sample is used in the methods of the invention without further treatment. In other embodiments, the sample is treated, e.g. to label one or more particles of interest, as described herein. The treatment may occur before introduction of the sample into the analyzer system of the invention, or it may occur after the sample is introduced into the system.

Particles for Analysis

Methods for detecting at least one single particle using the analyzers and analysis systems of the invention are also provided. A particular feature of this single particle analyzer is the ability to detect a wide range of particles. Particles which can be detected by the analyzer include, but are not limited to, molecules, supramolecular complexes, organelles, beads, associations of molecules, associations of supramolecular complexes, and organisms. Examples of molecular particles which can be detected using the analyzer and related methods of the present invention include: biopolymers such as proteins, nucleic acids, carbohydrates, and small particle chemical entities, both organic and inorganic. Examples of the latter include, but are not limited to anti-autoimmune deficiency syndrome substances, antibodies, anti-cancer substances, antibiotics, anti-viral substances, enzymes, enzyme inhibitors, neurotoxins, opioids, hypnotics, antihistamines, tranquilizers, anti-convulsants, muscle relaxants and anti-Parkinson substances, anti-spasmodic and muscle contractants, miotics and anti-cholinergics, immunosuppressants (e.g., cyclosporine) anti-glaucoma solutes, anti-parasite and/or anti-protozoal solutes, anti-hypertensives, analgesics, anti-pyretics and anti-inflammatory agents (such as Non-Steroidal Antiinflammatory Drugs), local anesthetics, ophthalmics, prostaglandins, anti-depressants, anti-psychotic substances, anti-emetics, imaging agents, specific targeting agents, neurotransmitters, proteins and cell response modifiers.

Similarly, detectable chemical entities encompass small particles such as amino acids, nucleotides, lipids, sugars, drugs, toxins, venoms, substrates, pharmacophores, and any combination thereof.

Proteins are also of interest in a wide variety of therapeutics and diagnostics, such as detecting cell populations, blood type, pathogens, immune responses to pathogens, immune complexes, saccharides, lectins, naturally occurring receptors, and the like.

Other examples of detectable particles include nanospheres, microspheres, dendrimers, chromosomes, organelles, micelles and carrier particles. Examples of organelles include subcellular particles such as nuclei, mitochondria, ribosomes, and endosomes. Examples of organisms include viruses, bacteria, fungal cells, animal cells, plant cells, eukaryotic cells, prokaryotic cells, archeobacter cells, and any combination thereof.

Those of skill in the art will recognize how to adapt the analyzer and related methods of the present invention, in light of the numerous Examples provided herein, to detect these and other particles.

In one embodiment, chemical entities that may be detected by the analyzer and related methods include synthetic or naturally occurring hormones, naturally occurring drugs, synthetic drugs, pollutants, allergens, affecter particles, growth factors, chemokines, cytokines, lymphokines, amino acids, oligopeptides, chemical intermediates, nucleotides, and oligonucleotides.

The methods described herein enable at least one particle to be distinguished singly in a sample comprising multiple particles. Amplification of the particle is not required. Multiple particles includes small particles, nucleic acids (e.g., single-stranded, double-stranded, DNA, RNA, and hybrids thereof), proteins (e.g., peptides, polypeptides and proteins), organic and inorganic molecules (e.g., metabolites, cytokines, hormones, neurotransmitters, and the like), and organisms (e.g., viruses and cells). In this regard, a sample comprising multiple particles can comprise multiple small particles, multiple particles of nucleic acids, multiple particles of proteins, multiple organic and/or inorganic molecules, and multiple cells and/or viruses or various combinations of the foregoing. Thus, any particle in a sample comprising (i) nucleic acids, small particles, organic/inorganic molecules, or proteins, (ii) nucleic acids and small particles, (iii) nucleic acids and proteins, (iv) proteins and small particles, (v) proteins and organic/inorganic molecules, (vi) nucleic acids and organic/inorganic molecules, or (vi) nucleic acids, small particles and proteins and combinations of the above with cells/viruses can be distinguished.

In addition to the particles described above, are particles comprising complexes such as nucleic acids hybridized to labels, antibody-antigen complexes, ligand-receptor complexes, enzyme-substrate complexes, and protein-nucleic acid complexes which can be discriminated using these methods.

Motive Force

The particles (e.g., labels to be detected) are moved by a motive force. In some embodiments, the motive force for moving particles is pressure. In some embodiments, the pressure is supplied by a pump.

Pressure

In some embodiments, pressure is supplied to move the sample by means of a pump. Suitable pumps are known in the art, e.g., those made by manufacturers such as Scivex, Inc., for applications such as HPLC. For pumping smaller volumes (e.g., when sample concentration is not limiting), microfluidics pumps may be useful, such as those described in U.S. Pat. Nos. 5,094,594, 5,730,187; 6,033,628; and 6,533,553, which disclose devices which can pump fluid volumes in the nanoliter or picoliter range. Preferably all materials within the pump that come into contact with sample are made of highly inert materials, e.g., polyetheretherketone (PEEK), fused silica, or sapphire.

Standard pumps come in a variety of sizes, and the proper size may be chosen to suit the anticipated sample size and flow requirements. In some embodiments, separate pumps are used for sample analysis and for flushing of the system. The analysis pump may have a capacity of, e.g. about 0.000001 mL to about 10 mL, or about 0.001 mL to about 1 mL, or about 0.01 mL to about 0.2 mL, or about 0.005, 0.01, 0.05, 0.1, or 0.5 mL. Flush pumps may be of larger capacity than analysis pumps, e.g. about 0.01 mL to about 20 mL, or about 0.1 mL to about 10 mL, or about 0.1 mL to about 2 mL, or about or about 0.05, 0.1, 0.5, 1, 5, or 10 mL. These pump sizes are illustrative on and those of skill in the art will appreciate that the pump size may be chosen according to the application, sample size, viscosity of fluid to be pumped, tubing dimensions, rate of flow, temperature, and other factors well known in the art. In some embodiments, pumps of the system are driven by stepper motors, which are easy to control very accurately with a microprocessor.

In preferred embodiments, the flush and analysis pumps are used in series, with special check valves to control the direction of flow. The plumbing is designed so that when the analysis pump draws up the maximum sample, the sample does not reach the pump itself. This is accomplished by choosing the ID and length of the tubing between the analysis pump and the analysis capillary such that the tubing volume is greater than the stroke volume of the analysis pump.

EM Radiation Source

EM radiation sources for excitation of fluorescent labels, e.g., a laser, are preferred.

Figure 8:
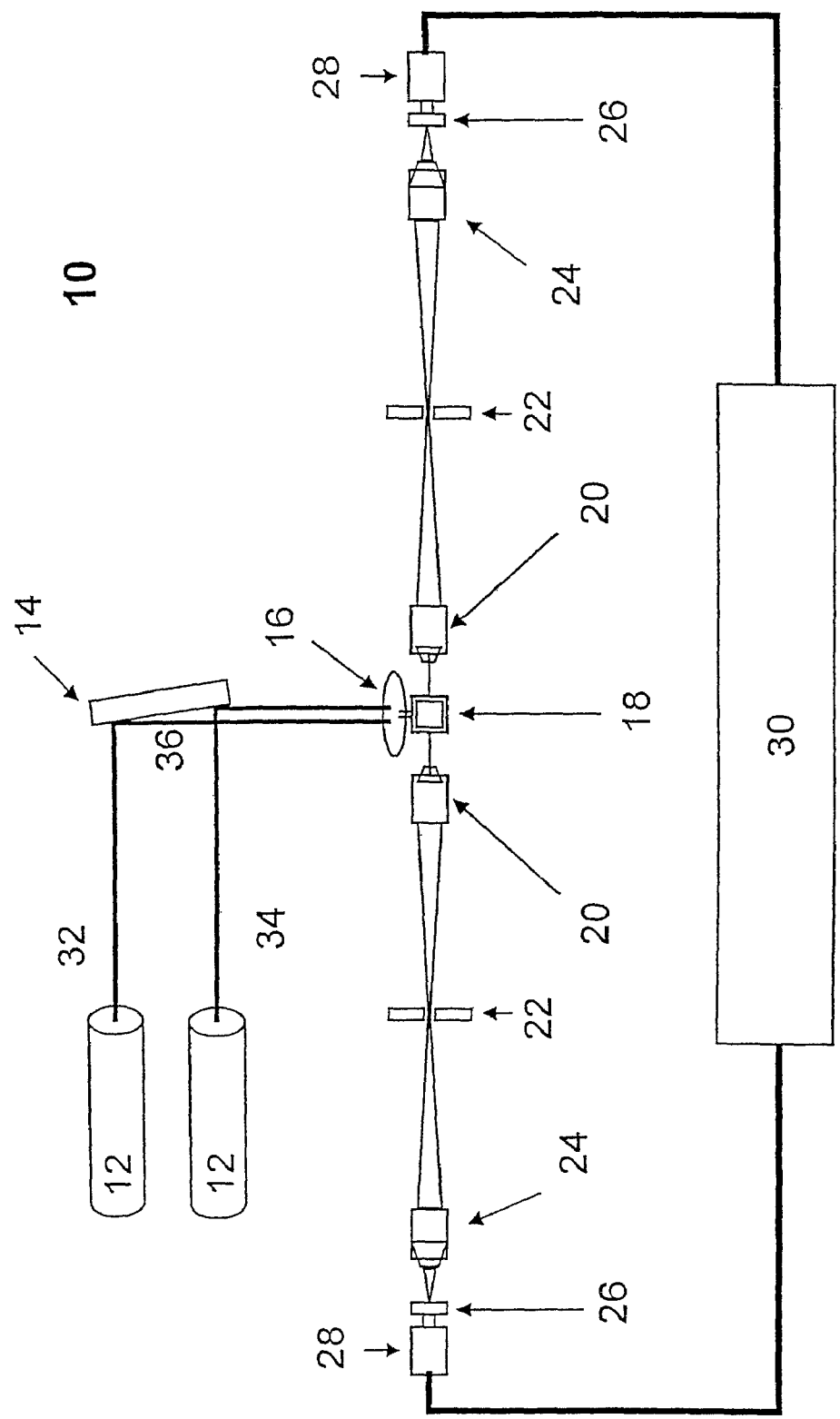
FIG. 8. Schematic diagram of a single particle analyzer of one embodiment of the present invention.

In the embodiment shown in FIG. 8, each of the interrogation spaces 38, 40 has a separate continuous wave electromagnetic radiation source 12. A similar radiation source is used in embodiments with only one interrogation space, and it will be understood that the following description applies equally to a single interrogation space.

Although other sources may be used without departing from the scope of the present invention, in one embodiment the sources 12 are continuous wave lasers producing wavelengths of between about 200 and about 1,000 nm. Such sources 12 have the advantage of being small, durable and relatively inexpensive. In addition, they generally have the capacity to generate larger fluorescent signals than other light sources. Specific examples of suitable continuous wave electromagnetic radiation sources include, but are not limited to: lasers of the argon, krypton, helium-neon, helium-cadmium types, as well as, tunable diode lasers (red to infrared regions), each with the possibility of frequency doubling. The lasers provide continuous illumination with no accessory electronic or mechanical devices such as shutters, to interrupt their illumination. LEDs are another low-cost, high reliability illumination source. Recent advances in ultra-bright LEDs and dyes with high absorption cross-section and quantum yield, support the applicability of LEDs to single particle detection. Such lasers could be used alone or in combination with other light sources such as mercury arc lamps, elemental arc lamps, halogen lamps, arc discharges, plasma discharges, light-emitting diodes, or combination of these.

The optimal laser intensity depends on the photo bleaching characteristics of the single dyes and the length of time required to traverse the interrogation space. To obtain a maximal signal, it is desirable to illuminate the sample at the highest intensity which will not result in photo bleaching a high percentage of the dyes. The preferred intensity is one such that no more that 5% of the dyes are bleached by the time the particle has traversed the final interrogation space.

In one embodiment, the interrogation space(s) 38, 40 are determined by the cross sectional area of the corresponding beams 32, 34 and by a segment of the beam within the field of view of the detector. It should be understood by one skilled in the art that the interrogation space(s) 38, 40 can be selected for maximum performance of the analyzer. Although very small interrogation spaces have been shown to minimize the background noise, large interrogation spaces have the advantage that low concentration samples can be analyzed in a reasonable amount of time. In one embodiment of the present invention, the interrogation space(s) are large enough to allow for detection of particles at concentrations ranging from about 1000 fM to about 1 zeptomolar (zM). In one embodiment of the present invention, the interrogation space(s) are large enough to allow for detection of particles at concentrations ranging from about 1000 fM to about 1 attomolar (aM). In one embodiment of the present invention, the interrogation space(s) are large enough to allow for detection of particles at concentrations ranging from about 10 fM to about 1 attomolar (aM). In many cases, the large interrogation space(s) allow for the detection of particles at concentrations of less than about 1 fM without additional pre-concentration devices or techniques. One skilled in the art will recognize that the most appropriate interrogation space size depends on the brightness of the particles to be detected, the level of background signal, and the concentration of the sample to be analyzed.

The size of the interrogation space(s) 38, 40 can be limited by adjusting the optics of the analyzer. In one embodiment, the diameter of the beam(s) 32, 34 can be adjusted to vary the volume of interrogation space(s) 38, 40. In another embodiment, the field of view of the detector 26 can be varied. Thus, the source(s) 12 and the detector(s) 26 can be adjusted so that single particles will be illuminated and detected within the interrogation space(s) 38, 40. In another embodiment, the width of slit(s) 22 (FIG. 8) that determine the field of view of the detector(s) 26 are variable. This configuration allows for altering the interrogation space, in near real time, to compensate for more or less concentrated samples, ensuring a low probability of two or more particles simultaneously being within in an interrogation space.

Physical constraints to the interrogation space(s) can also be provided by a solid wall. In one embodiment, the wall is one or more of the cell 18 walls, when the sample fluid is contained within a capillary. In one embodiment, the cell 18 is made of glass, but other substances transparent to light in the range of about 200 to about 1,000 nm or higher, such as quartz, fused silica, and organic materials such as Teflon, nylon, plastics, e.g., polyvinylcbloride, polystyrene and polyethylene, or any combination thereof, may be used without departing from the scope of the present invention. Although other cross-sectional shapes (e.g., rectangular, cylindrical) may be used without departing from the scope of the present invention, in one embodiment the capillary flow cell 18 has a square cross section. In another embodiment, the interrogation spaces may be defined at least in part by a channel (not shown) etched into a chip (not shown).

In another embodiment of the invention, an interrogation space 38, 40 is constrained by the size of a laminar flow of the sample material within a diluent volume, also called sheath flow. The interrogation space 38, 40 can be defined by sheath flow alone or in combination with the dimensions of the illumination source or the field of view of the detector. Sheath flow can be configured in numerous ways, including those listed below:
1. The sample material is the interior material in a concentric laminar flow, with the diluent volume in the exterior.
2. The diluent volume is on one side of the sample volume.
3. The diluent volume is on two sides of the sample material.
4. The diluent volume is on multiple sides of the sample material, but not enclosing the sample material completely.
5. The diluent volume completely surrounds the sample material.
6. The diluent volume completely surrounds the sample material concentrically.
7. The sample material is the interior material in a discontinuous series of drops and the diluent volume completely surrounds each drop of sample material.

One skilled in the art will recognize that in some cases the analyzer will contain 1, 2, 3, 4, 5, 6 or more distinct interrogation spaces.

Detectors

In one embodiment, light (e.g., light in the ultra-violet, visible or infrared range) is the electromagnetic radiation detected. The detector(s) 26 are capable of capturing the amplitude and duration of photon bursts from, e.g., fluorescent particles and converting them to electronic signals. Detection devices such as CCD cameras, video input module cameras, and Streak cameras can be used to produce images with contiguous signals. In another embodiment, devices such as a bolometer, a photodiode, a photodiode array, avalanche photodiodes, and photomultipliers which produce sequential signals may be used. Any combination of the aforementioned detectors may also be used. In one embodiment, avalanche photodiodes are used for detecting photons.

Using specific optics between an interrogation space 38, 40 and its corresponding detector 26, several distinct characteristics of the emitted electromagnetic radiation can be detected including: emission wavelength, emission intensity, burst size, burst duration, and fluorescence polarization.

It should be understood by one skilled in the art that one or more detectors 26 can be configured at each interrogation space 38, 40 and that the single detectors 26 may be configured to detect any of the characteristics of the emitted electromagnetic radiation listed above.

Once a particle is labeled to render it detectable (or if the particle possesses an intrinsic characteristic rendering it detectable), any suitable detection mechanism known in the art may be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. In one embodiment, avalanche photodiodes are used for detecting photons. Different characteristics of the electromagnetic radiation may be detected including: emission wavelength, emission intensity, burst size, burst duration, fluorescence polarization, and any combination thereof.

Counting and Discrimination

The methods described herein allow particles (e.g., protein molecules) to be enumerated as they pass through the interrogation spaces one at a time, as described previously. The concentration of the sample can be determined from the number of particles counted and the volume of sample passing though the interrogation space in a set length of time. In the case where an interrogation space encompasses the entire cross-section of the sample stream, only the number of particles (e.g., labels) counted and the volume passing through a cross-section of the sample stream in a set length of time are needed to calculate the concentration the sample. The concentration of the particle (e.g., protein) can be also determined by interpolating from a standard curve generated with a control sample of standard concentration. In another embodiment, the concentration of the particle can be determined by comparing the measured particles to an internal particle standard. Knowing the sample dilution, one can calculate the concentration of particles in the starting sample.

In some embodiments, an analyzer or analyzer system of the invention is capable of detecting an analyte, e.g., a biomarker at a level of less than 1 nanomolar, or 1 picomolar, or 1 femtomolar, or 1 attomolar, or 1 zeptomolar. In some embodiments, the analyzer or analyzer system is capable of detecting a change in concentration of the analyte, or of multiple analytes, e.g., a biomarker or biomarkers, from one sample to another sample of less than about 0.1, 1, 2, 5, 10, 20, 30, 40, 50, 60, or 80% when the biomarker is present at a concentration of less than 1 nanomolar, or 1 picomolar, or 1 femtomolar, or 1 attomolar, or 1 zeptomolar, in the samples, and when the size of each of the sample is less than about 100, 50, 40, 30, 20, 10, 5, 2, 1, 0.1, 0.01, 0.001, or 0.0001 ul.

Analyzer Systems

In addition to the single particle analyzers described herein, the invention also provides analyzer systems, which may include, in addition to a single particle analyzer, a sampling system, sample recovery system, sample preparation system, a computer for controlling parameters of analysis such as flow rates, etc., and/or a data analysis and reporting system that includes a computer and/or analyzing raw data and a reporting device for reporting the results of this analysis.

In some embodiments, the analyzer system includes a sampling system capable of automatically sampling a plurality of samples and providing a fluid communication between a sample container and a first interrogation space; and an analyzer capable of detecting a single molecule, where the analyzer includes (i) an electromagnetic radiation source for emitting electromagnetic radiation; (ii) said first interrogation space positioned to receive electromagnetic radiation emitted from the electromagnetic radiation source; and (iv) a first electromagnetic radiation detector operably connected to the first interrogation space to measure a first electromagnetic characteristic of the particle. In some embodiments, the analyzer further includes a second interrogation window, with the capability of detecting single particles, as described above.

Sampling System

In some embodiments, the analyzer system of the invention includes a sampling system for introducing an aliquot of a sample into the single particle analyzer for analysis. Any mechanism that can introduce a sample may be used. Samples can be drawn up using either vacuum (negative pressure) from the pump or pressure applied to the sample that would push liquid into the tube, or by any other mechanism that serves to introduce the sample into the sampling tube. Generally, but not necessarily, the sampling system introduces a sample of known sample volume into the single particle analyzer; in some embodiments where the presence or absence of a particle or particles is detected, precise knowledge of sample size is not critical. In preferred embodiments the sampling system provides automated sampling for a single sample or a plurality of samples. In embodiments where a sample of known volume is introduced into the system, the sampling system provides a sample for analysis of more than about 0.0001, 0.001, 0.01, 0.1, 1, 2, 5, 10, 20, 30, 40, 50, 60, 70, 80, 90, 100, 150, 200, 500, 1000, 1500, or 2000 ul. In some embodiments the sampling system provides a sample for analysis of less than about 2000, 1000, 500, 200, 100, 90, 80, 70, 60, 50, 40, 30, 20, 10, 5, 2, 1, 0.1, 0.01, or 0.001 ul. In some embodiments the sampling system provides a sample for analysis of between about 0.01 and 1500 ul, or about 0.1 and 1000 ul, or about 1 and 500 ul, or about 1 and 100 ul, or about 1 and 50 ul, or about 1 and 20 ul. In some embodiments, the sampling system provides a sample for analysis between about 5 ul and 200 ul, or about 5 ul and about 100 ul, or about 5 ul and 50 ul. In some embodiments, the sampling system provides a sample for analysis between about 10 ul and 200 ul, or between about 10 ul and 100 ul, or between about 10 ul and 50 ul. In some embodiments, the sampling system provides a sample for analysis between about 0.5 ul and about 50 ul. In some embodiments, the sampling system provides a sample for analysis of about 1, 2, 3, 4, 5, 6, 7, 8, 9, 10, 15, 20, 25, 30, 35, 40, 45, 50, 60, 70, 80, 90, 100, 150, 200, 500, 1000, or 2000 ul. In some embodiments, the sampling system provides a sample for analysis of about 50 ul. In some embodiments, the sampling system provides a sample for analysis of about 25 ul. In some embodiments, the sampling system provides a sample for analysis of about 10 ul. The sampling system may provide a sample size larger than that actually analyzed. For example, the sampling system may draw up about 25 ul, or about 20 ul, or about 15 ul, or about 10 ul, of sample, of which only about 1 to about 5 ul is analyzed.

In some embodiments, the sampling system provides a sample size that can be varied from sample to sample. In these embodiments, the sample size may be any one of the sample sizes described herein, and may be changed with every sample, or with sets of samples, as desired.

Sample volume accuracy, and sample to sample volume precision of the sampling system, are as required for the analysis at hand. In some embodiments, the precision of the sampling volume is determined by the pumps used, typically represented by a CV of less than about 50, 40, 30, 20, 10, 5, 4, 3, 2, 1, 0.5, 0.1, 0.05, or 0.01% of sample volume. In some embodiments, the sample to sample precision of the sampling system is represented by a CV of less than about 50, 40, 30, 20, 10, 5, 4, 3, 2, 1, 0.5, 0.1, 0.05, or 0.01%. In some embodiments, the intra-assay precision of the sampling system is represented by a CV of less than about 10, 5, 1, 0.5, or 0.1%. In some embodiments, the intra-assay precision of the sampling system shows a CV of less than about 5%. In some embodiments, the interassay precision of the sampling system is represented by a CV of less than about 10, 5, or 1%. In some embodiments, the interassay precision of the sampling system shows a CV of less than about 5%.

In some embodiments, the sampling system provides low sample carryover, advantageous in that an additional wash step is not required between samples. Thus, in some embodiments, sample carryover is less than about 1, 0.5, 0.1, 0.05, 0.04, 0.03, 0.02, 0.01, 0.005, or 0.001%. In some embodiments, sample carryover is less than about 0.02%. In some embodiments, sample carryover is less than about 0.01%.

In some embodiments the sampler provides a sample loop. In these embodiments, multiple samples are drawn into tubing sequentially and each is separated from the others by a "plug" of buffer. The samples typically are read one after the other with no flushing in between. Flushing is done once at the end of the loop. It is possible to recover each plug in, e.g., a separate well of a microtiter plate.

The sampling system may be adapted for use with standard assay equipment, for example, a 96-well microtiter plate, or, preferably, a 384-well plate. In some embodiments the system includes a 96 well plate positioner and a mechanism to dip the sample tube into and out of the wells, e.g., a mechanism providing movement along the X, Y, and Z axes. In some embodiments, the sampling system provides multiple sampling tubes; e.g., multiple tubes that "sip" from a row of 8 wells on a microtiter plate. In some embodiments, all samples from the multiple tubes are analyzed on one detector; in other embodiments, multiple single molecule detectors may be connected to the sample tubes. Samples may be prepared by steps that include operations performed on sample in the wells of the plate prior to sampling by the sampling system, or sample may be prepared within the analyzer system, or some combination of both.

Sample Preparation

Sample preparation includes the steps necessary to prepare a raw sample for analysis. These steps can involve, by way of example, one or more of: separation steps such as centrifugation, filtration, distillation, chromatography; concentration, cell lysis, alteration of pH, addition of buffer, addition of diluents, addition of reagents, heating or cooling, addition of label, binding of label, cross-linking with illumination, separation of unbound label, inactivation and/or removal of interfering compounds and any other steps necessary for the sample to be prepared for analysis by the single particle analyzer. In some embodiments, blood is treated to separate plasma or serum. Additional labeling, removal of unbound label, and/or dilution steps may also be performed on the serum or plasma sample.

As is known in the art, sample preparation in which, e.g., a label is added to one or more particles may be performed in a homogeneous or heterogeneous format. In homogeneous systems, unbound label is not removed from the sample. In some embodiments, the particle or particles of interest are labeled by addition of labeled antibody or antibodies that binds to the particle or particles of interest. In heterogeneous systems, one or more steps are added for the removal of unbound label. In some embodiments, a separation step using, e.g., a capture antibody for immobilizing the particle of interest, is also used. Thus, in some embodiments, homogeneous preparation includes the following steps: 1) add sample suspected of containing particle of interest; 2) add detection (e.g., labeled) antibody. In some embodiments, heterogeneous preparation involves the following steps: 1) add capture antibody; 2) wash; 3) block; 4) add sample suspected of containing particle of interest; 5) wash; 6) add detection (e.g., labeled) antibody; 7) wash; 8) release bound molecules (may require neutralizing, depending on the method).

Preferably, the sample (e.g., processed sample) comprises a buffer. The buffer may be mixed with the sample outside the analyzer system, or it may be provided by the sample preparation mechanism. While any suitable buffer can be used, the preferable buffer has low fluorescence background, is inert to the detectably labeled particle, can maintain the working pH. The buffer concentration can be any suitable concentration, such as in the range from about 1 to about 200 mM. Any buffer system may be used as long as it provides for solubility, function, and delectability of the molecules of interest. Preferably, for application using pumping, the buffer is selected from the group consisting of phosphate, glycine, acetate, citrate, acidulate, carbonate bicarbonate, imidazole, triethanolamine, glycine amide, borate, MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. An especially preferred buffer is 2 mM Tris/borate at pH 8.1, but Tris/glycine and Tris/HCl are also acceptable.

In order to be detected, particles must produce, or be made capable of producing electromagnetic radiation. Preferably, the means of detection is a fluorescent label. Examples of fluorescent labels can be found in the Handbook of Fluorescent Probes and Research Products (R. Haugland, 9th Ed., Molecular Probes Pub. (2004)). A detectable label may also be produced by any combination of intrinsic and extrinsic properties of the particle.

Methods for labeling the particle (e.g., protein molecule) are well known by those of ordinary skill in the art. Attaching labels to particles can employ any known method including attaching directly or using binding partners. Labels of the present invention include dye tags, charge tags, mass tags, Quantum Dots, or beads, magnetic tags, light scattering tags, polymeric dyes, and dyes attached to polymers.

Dyes include a very large category of compounds that add color to materials or enable generation of luminescent or fluorescent light. A dye may absorb light or emit light at specific wavelengths. A dye may be intercalating, or be non-covalently or covalently bound to a particle. Dyes themselves may constitute probes as in probes that detect minor groove structures, cruciforms, loops or other conformational elements of particles. Dyes may include, BODIPY and ALEXA dyes, Cy[n] dyes, SYBR dyes, ethidium bromide and related dyes, acridine orange, dimeric cyanine dyes such as TOTO, YOYO, BOBO, TOPRO POPRO, and POPO and their derivatives, bis-benzimide, OliGreen, PicoGreen and related dyes, cyanine dyes, fluorescein, LDS 751, DAPI, AMCA, Cascade Blue, CL-NERF, Dansyl, Dialkylaminocoumarin, 4',5'-Dichloro-2',7'-dimethoxyfluorescein, 2',7'-Dichlorofluorescin, DM-NERF, Eosin, Erythrosin, Fluoroscein, Hydroxycourmarin, Isosulfan blue, Lissamine rhodamine B, Malachite green, Methoxycoumarin, Naphthofluorescein, NBD, Oregon Green, PyMPO, Pyrene, Rhodamine, Rhodol Green, 2',4',5',7'-Tetrabromosulfonefluorescein, Tetramethylrhodamine, Texas Red, X-rhodamine, Dyomic dye series, Atto-tec dye series, Coumarins, phycobilliproteins (phycoerythrins, phycocyanins, allophycocyanins), green, yellow, red and other fluorescent proteins, up-converting phosphors, and Quantum Dots, and any other dyes described herein. Those skilled in the art will recognize other dyes which may be used within the scope of the invention. This is not an exhaustive list, and acceptable dyes include all dyes now known or known in the future which could be used to allow detection of the labeled particle of the invention. By having fluorescent markers, such as fluorescent particles, fluorescent conjugated antibodies, or the like, the sample may be irradiated with light that is absorbed by the fluorescent particles and the emitted light measured by light measuring devices.

Polysaccharide coated paramagnetic microspheres or nanospheres may be used to label particles. U.S. Pat. No. 4,452,773 issued to Molday, incorporated herein by reference in its entirety, describes the preparation of magnetic iron-dextran beads and provides a summary describing the various methods of preparing particles suitable for attachment to biological materials. A description of polymeric coatings for magnetic particles used in high gradient magnetic separation methods are found in German Patent No. 3720844 and U.S. Pat. No. 5,385,707 issued to Miltenyi, both incorporated herein by reference in their entireties. Methods to prepare paramagnetic beads are described in U.S. Pat. No. 4,770,183.

The exact method for attaching the bead to the particle is not critical to the practice of the invention, and a number of alternatives are known in the art. The attachment is generally through interaction of the particle with a specific binding partner which is conjugated to the coating on the bead and provides a functional group for the interaction. Antibodies are examples of binding partners. Antibodies may be coupled to one member of a high affinity binding system, e.g., biotin, and the particles attached to the other member, e.g., avidin. Secondary antibodies that recognize species-specific epitopes of the primary antibodies, e.g., anti-mouse Ig, and anti-rat Ig, may also be used in the present invention. Indirect coupling methods allow the use of a single magnetically coupled entity, e.g., antibody, avidin, etc., with a variety of particles.

In one application of this technique, described by Cohen (Cohen et al. (1988) PNAS 85:9660-3), the target particle may be coupled to a magnetic tag and suspended in a fluid within a chamber (not shown). In the presence of a magnetic field supplied across the chamber, the magnetically labeled target is retained in the chamber. Materials which do not have magnetic labels pass through the chamber. The retained materials can then be eluted by changing the strength of, or by eliminating, the magnetic field. The chamber across which the magnetic field is applied is often provided with a matrix of a material of suitable magnetic susceptibility to induce a high magnetic field locally in the chamber in volumes close to the surface of the matrix. This permits the retention of fairly weakly magnetized particles and the approach is referred to as high gradient magnetic separation.

Techniques to non-specifically label proteins are also well known to one skilled in the art. Several chemically reactive amino acids on the surface of proteins can be used, for example, primary amines such a lysine. In addition, labels can be added to carbohydrate moieties on proteins. Isotype specific reagents have also been developed for labeling antibodies, such as Zenon labeling (Haugland, 2004).

In one embodiment, only specific particles within a mixture are labeled. Specific labeling can be accomplished by combining the target particle with a labeled binding partner, where the binding partner interacts specifically with the target particle through complementary binding surfaces. Binding forces between the partners can be covalent interactions or non-covalent interactions such as hydrophobic, hydrophilic, ionic and hydrogen bonding, van der Waals attraction, or coordination complex formation. Examples of binding partners are agonists and antagonists for cell membrane receptors, toxins and venoms, antibodies and viral epitopes, hormones (e.g., opioid peptides, steroids, etc.) and hormone receptors, enzymes and enzyme substrates, cofactors and target sequences, drugs and drug targets, oligonucleotides and nucleic acids, proteins and monoclonal antibodies, antigen and specific antibody, polynucleotide and complementary polynucleotide, polynucleotide and polynucleotide binding protein; biotin and avidin or streptavidin, enzyme and enzyme cofactor; and lectin and specific carbohydrate. Illustrative receptors that can act as a binding partner include naturally occurring receptors, e.g., thyroxine binding globulin, lectins, various proteins found on the surface of cells (cluster of differentiation or CD particles), and the like. CD molecules denote known and unknown proteins on the surface of eukaryotic cells, e.g., CD4 is the molecule that primarily defines helper T lymphocytes.

In one embodiment, a sample is reacted with beads or microspheres that are coated with a binding partner that reacts with the target particle. The beads are separated from any non-bound components of the sample, and the beads containing bound particles are detected by the analyzer of the invention. Fluorescently stained beads are particularly well suited for these methods. For example, fluorescent beads coated with oligomeric sequences will specifically bind to target complementary sequences, and after the appropriate separation steps, allow for detection of the target sequence.

In one embodiment, a method for detecting particles uses a sandwich assay with monoclonal antibodies as binding partners. The primary antibody is linked to a surface to serve as capture antibody. The sample would then be added and particles having the epitope recognized by the antibody would bind to the antibody on the surface. Unbound particles are washed away leaving substantially only specifically bound particles. The bound particle/antibody can then be reacted with a detection antibody containing a detectable label. After incubating to allow reaction between the detection antibodies and particles, non-specifically bound detection antibodies are washed away. The particle and detection antibody can be released from the surface and detected in the analyzer of the invention. Alternatively, only the detection antibody can be released and detected, thereby indirectly detecting the particle. Alternatively, only the label bound to the detection antibody can be released and detected, thereby indirectly detecting the particle.

Data Collection, Analysis, and Reporting

Data, consisting of signals detected from the particles, are analyzed using, for example, a personal computer (not shown in FIG. 6) with standard or custom software. A computer may also be used to operate the analyzer, e.g., to control flow rates, operate sampling, sample recovery, sample preparation, and the like.

The system may also include a data reporter for reporting the data and/or results of analysis. Any means known to those of skill in the art may be used for this purpose. The raw data (e.g., number of particles, cross-correlation data, wavelength of fluorescence, intensity of fluorescence, and the like) may be further analyzed by appropriate software before reporting, to indicate probable identity of particles in the sample, concentration, combinations of particles detected, levels of detected particles compared to normal, abnormal, or specific levels associated with specific conditions, possible diagnoses based on the presence, absence, and/or concentration of one or more particles, possible sources of particles detected, and any other analysis that may be performed on the data before reporting. Any mechanism that provides an appropriate report may be used as a data reporter. Non-exclusive examples of data reporters include display on a video monitor, printout, transmission of data for remote display or printout, e.g., over the Internet, voice report, and the like.

Methods

Figure 7:
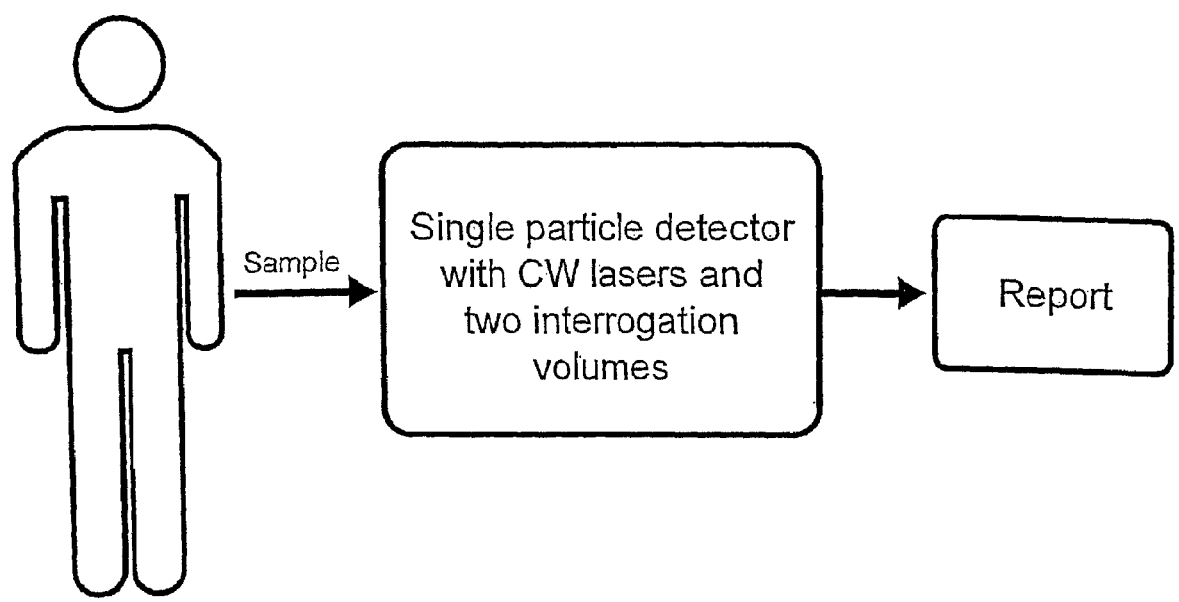
FIG. 7. Schematic view of one embodiment of methods of the invention. The diagram indicates two interrogation spaces; however, one interrogation space is included in the invention.

The invention also provides a method of analysis that includes determining a diagnosis, prognosis, state of a treatment (e.g., monitoring the progress and/or effect of a treatment), and/or method of treatment based on the presence, absence, and/or concentration of a particle in a sample taken from an individual, where the presence, absence, and/or concentration is determined by the methods described herein. "Diagnosis," as used herein, includes use of the results of tests to screen an individual to determine predisposition to a disease or pathology, or the presence and/or severity of a disease or pathology, and includes determination of a lack of predisposition or presence of the disease or pathology. These methods may further include reporting the diagnosis, prognosis, state of a treatment, monitoring and/or determination of treatment to the individual from whom the sample was obtained, and/or their representative (e.g., health care provider). The single particle detector may be any of the embodiments described herein, including analyzers and analyzer systems. FIG. 7 provides an illustration of one embodiment of the methods of the invention. A sample from an individual (e.g., a human) is analyzed using a detection system with two interrogation spaces (as shown in the Figure; embodiments using only a single interrogation space are also encompassed by the invention, as described herein) capable of detecting single molecules (in some embodiments utilizing CW laser as a source of EM radiation) and results of the analysis are obtained. In some embodiments, the results may be in terms of presence, absence, and/or concentration of a particle or particles of interest; in some embodiments, the results have been further analyzed to provide a diagnosis, prognosis, determination of treatment efficacy, determination of type of treatment, and the like. In some embodiments, the report is communicated to the individual or their representative.

The invention also provides methods of data analysis by computer analysis of a database. The database contains results of analysis of a sample or samples performed using a single particle detector as described herein, where the analysis includes determining the presence, absence, and/or concentration of a particle in the sample. In some embodiments, the analysis includes determining the presence, absence, and/or concentration of a plurality of types of particles in the sample(s). The samples may be obtained from any of the sources described herein. In some embodiments, the samples are obtained in biomedical research, such as in clinical trials or pre-clinical trial research, or basic research. The single particle detector may be any of the embodiments described herein. The detection system may utilize a CW laser as a source of electromagnetic radiation.

In some aspects, the invention provides a computer-readable storage medium, such as a CD, containing a set of instructions for a general purpose computer having a user interface comprising a display unit, e.g., a video display monitor or a printing unit, where the set of instructions includes logic for inputting values from analysis of a sample with a single particle detector with two interrogation spaces; optionally, a comparison routine for comparing the inputted values with a database; and a display routine for displaying the results of the input values and/or comparison routine with said display unit. In another embodiment of this aspect, the invention provides an electronic signal or carrier wave that is propagated over the Internet between computers containing a set of instructions for a general purpose computer having a user interface comprising a display unit, e.g., a video display monitor or a printing unit, where the set of instructions includes logic for inputting values from analysis of a sample with a detection system capable of detecting single molecules as described herein; a comparison routine for comparing the inputted values with a database; and a display routine for displaying the results of the comparison routine with said display unit.

The methods of the invention are useful in, for example, determining the results of research, e.g., biomedical research, including, but not limited to, pre-clinical and clinical trials, in a rapid, robust, and sensitive manner. The methods of the invention are also useful in, e.g., clinical diagnosis, prognosis, monitoring, and determination of methods of treatment. In these embodiments the method may further include the step of reporting the results of the analysis, or the diagnosis, prognosis, monitoring or treatment determined from the results of the analysis, to the individual from whom the sample was taken or their representative.

Samples may be any of those described herein. Thus, for example, the sample may be a biological fluid, e.g., blood, serum, plasma, bronchoalveolar lavage fluid, urine, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the particle of interest. In some embodiments, the sample is a blood sample. In some embodiments, the sample is a plasma sample. In some embodiments, the sample is a serum sample.

Particles within the sample whose presence, absence, and/or concentration are detected are also as described herein, e.g., protein molecules. In some embodiments, the sample is treated before introduction into the detection system. In some embodiments, the sample is introduced into the detection system without treatment; in these embodiments, the sample may be capable of detection without further treatment, or the sample may be treated within the detection system prior to analysis in the system. Treatment, either before or after introduction, may be as described elsewhere herein.

In some embodiments, sample treatment includes labeling a particle with a fluorescently-labeled antibody that is specific to the particle. In some embodiments, the particle that is labeled is a biomarker. Biomarkers include, but are not limited to, markers for inflammation, microbial infection, pathological conditions, expression markers, developmental markers, and the like.

Exemplary markers that may be used are shown in FIG. 14, and described below. Further markers are as described previously.

Markers for bioterrorism sample analysis may include one or more of the more than thirty pathogens and toxins on various agency threat lists, as known to those of skill in the art. Public health personnel rarely see most of the pathogens in suspect samples, so they have difficulty identifying them quickly. In addition, many pathogenic infections are not immediately symptomatic in infected subjects, having delayed onset of symptoms as long as several days, limiting options to control the disease and to treat the subjects. The lack of a practical monitoring network capable of rapidly detecting and identifying multiple pathogens or toxins on current threat lists translates into a major deficiency in the ability to counter biological terrorism.

Biothreat agent sensors that operate in "Detect to Protect/Warn" programs are preferably 1) capable of detecting biothreat agents within a 1-2 hour time window, allowing enough time to respond to an event, 2) extremely low cost to maintain, allowing for continuous monitoring when needed, and 3) have sufficient selectivity to virtually eliminate false positives. The U.S. Bio-Watch program involves the Department of Energy, the Environmental Protection Agency (EPA), and the U.S. Department of Health and Human Services' Centers for Disease Control and Prevention. Eventually, this program will have the capability of detecting a biological attack in more than 120 U.S. cities and reporting the attack within twenty-four hours.

The Bio-Watch program utilizes the Autonomous Pathogen Detection System ("APDS"), a file-cabinet-sized machine that samples air, runs tests, and reports the results. APDS integrates a flow cytometer and real-time PCR-amplified detector with sample collection, sample preparation, and fluidics to provide a compact, autonomously operating instrument capable of simultaneously detecting multiple pathogens and/or toxins. The system is designed for fixed locations, where it continuously monitors air samples and automatically reports the presence of specific biological agents. APDS is targeted for subway systems, transportation terminals, large office complexes, and convention centers and provides the ability to measure up to 100 different agents and controls in a single sample. The latest evolution of the biodetector, APDS-II, uses bead-capture immunoassays and a compact flow cytometer for the simultaneous identification of multiple biological simulants. The present invention is not limited by the same requirements as the APDS system and can more quickly, cheaply and accurately provide the same detection.

In addition, the present invention has many other applications in medicine, medical examination, diagnosis, prognosis, monitoring and/or treatment selection; and in biomedical research. In some embodiments, the invention can be used for detecting controlled drugs and substances, therapeutic dosage monitoring, health status, donor matching for transplantation purposes, pregnancy (e.g., through detection of Human Chorionic Gondaotropin or alpha-fetoprotein), and detection of disease, e.g., endotoxins, cancer antigens, pathogens, and the like.

In some embodiments, markers for clinical diagnostics, e.g., of infectious disease or of inflammation, are used. Samples may be labeled, for example, to detect, in a single sample, antigens or antibodies associated with any of a number of infectious agents including, without limitation, bacteria, viruses, fungi, *mycoplasma*, rickettsia, *chlamydia*, prions, and protozoa; to assay for autoantibodies associated with autoimmune disease, to assay for agents of sexually transmitted disease, or to assay for analytes associated with pulmonary disorders, gastrointestinal disorders, cardiovascular disorders, neurological disorders, musculoskeletal disorders, dermatological disorders, and the like. Markers for clinical diagnostics may include other markers for the presence of conditions associated with a particular disease or pathological state, e.g., markers for inflammation.

For example, for the diagnosis of sepsis, various combinations of the following diagnostic markers may be used: inflammation biomarker TREM-1; inflammation biomarker IL-6 and IL-8; inflammation biomarker IL-10 and IL-12, and optionally IL-18; a fungal infection biomarker; one or more pathogen markers for *E. coli*, e.g., for multiple specific strains; one or more pathogen markers for Staphylococcus aureus, e.g., for multiple specific strains; one or more pathogen markers for Candida albicans, e.g., for multiple specific strains; one or more pathogen markers for Enterobacter, e.g., for multiple specific strains; as well as other clinical markers and, optionally, negative controls.

In some embodiments, clinical diagnosis may be based on only one marker, e.g., on TREM-1 for determination of the presence or absence of sepsis, or, for lung samples, the presence or absence of pneumonia (e.g., with ventilator patients). The diagnosis may be performed using a plasma, serum or BAL sample. Diagnosis may be based on comparison of the value obtained from the analyzed sample to values for normal and abnormal (e.g., diseased) populations.

In some embodiments, a panel of markers for diagnosis for community-acquired pneumonia may be used which is combinations of any or all of: inflammation biomarker TREM-1; inflammation biomarker IL-6 and IL-8; inflammation biomarker IL-10 and IL-12, and optionally IL-18; viral infection biomarker SAA; one or more pathogen markers for Streptococcus pneumoniae, e.g., for multiple specific strains; one or more pathogen markers for Respiratory Syncytial Virus, e.g., for multiple specific strains; one or more pathogen markers for Haemophilus, e.g., for multiple specific strains; one or more pathogen markers for *Mycoplasma*, e.g., for multiple specific strains; as well as other clinical markers and, optionally, negative controls. Panels for, e.g., bacterial pathogens will be apparent to those of skill in the art; see, e.g., Dunbar et al. 2003. J Microbiol Methods 53:245-52.

Detection and diagnosis of infectious diseases often requires testing for multiple antibodies; accordingly, specific antibodies may also be by the detection of combinations of, e.g., *Adenovirus, Bordetella pertussis, Campylobacter jejuni, Chlamydia pneumoniae, Chlamydia trachomatis, Cholera Toxin, Cholera Toxin b, Clostridium piliforme* (Tyzzer's), Cytomegalovirus, Diphtheria Toxin, Ectromelia virus, EDIM (Epidemic diarrhea of infant mice), *Encephalitozoon cuniculi*, Epstein-Barr EA, Epstein-Barr NA, Epstein-Barr VCA, HBV Core, HBV Envelope, HBV Surface (Ad), HBV Surface (Ay), HCV Core, HCV NS3, HCV NS4, HCV NS5, *Helicobacter pylori*, Hepatitis A, Hepatitis D, HEV orf2 3 KD, HEV orf2 6 KD, HEV orf3 3 KD, HIV-1 gp120, HIV-1 gp41, HIV-1 p24, HPV, HSV-1 gD, HSV-1/2, HSV-2 gG, HTLV-1/2, Influenza A, Influenza A H3N2, Influenza B, *Leishmmani donovani*, Lyme disease, Lymphocytic choriomeningitis virus, *M. pneumoniae, M. tuberculosis*, Minute virus, Mumps, *Mycoplasma pulmonis*, Parainfluenza 1, Parainfluenza 2, Parainfluenza 3, Parvovirus, Pneumonia virus of mice, Polio Virus, Polyoma virus, Reovirus-3, RSV, Rubella, Rubeola, Sendai virus, *T. cruzi, T. pallidum* 15 kd, *T. pallidum* p47, Tetanus Toxin, Theiler's mouse encephalomyelitis virus, Toxoplasma, and *Varicella zoster*.

Isotyping panels are useful for detection, characterization, and the like of antibody immunodeficiency disorders, such as multiple myeloma, HIV infection, solid organ tumors, or chronic liver disease. Such panels are also useful for researchers seeking to measure overall levels of certain isotypes in particular diseases or disease, such as various IgG deficiencies related to responder/nonresponder status, increased or unusual allergies, autoimmune diseases, GI disorders, malignancies, chest symptoms, or recurrent bacterial infections. Panels may include combinations of, for example, IgA, IgE, IgG1, IgG2alpha, IgG2beta, IgG3, IgM, and light chain (kappa or gamma).

To detect phospho-transferase activity of multiple different protein kinases, useful to clinicians and researchers, a substrate proteins may be mixed with ATP, followed by contact with, e.g., different color-coded antibodies, followed by, e.g., a biotinylated reporter antibody and a streptavidin-phycoerythrin conjugate. Each reaction may then be detected by its unique label. Panels may include combinations of, e.g., Akt, Akt/PKB (total), Akt/PKBpS473, ATF2 (Thr71), Erk-2, Erk1 (Thr202/Tyr204), Erk1/Erk2 (Thr202/Tyr204), Erk2 (Thr202/Tyr204), GSK-3beta, IkappaB-alpha pS32, IkappaB-alpha Total, JNK (pTpY183/185), JNK Total, JNKp (Thr183/Y182), MAPKAP K2, p38 (total), p38 MAPK pT180/pY182, p53 (total), p53 pS15, PKB-alpha, PKC, SAPK1, SAPK1a/JNK2, SAPK4, STAT1 pY701, STAT1 Total, STAT3 (Tyr705), andZAP-70. The system can detect modified proteins, e.g., proteins phosphorylated by modification with specific antibodies. The system can detect one or more modifications of one or more types of individual molecules.

To detect normal and disease states involving tissue remodeling, such as cancer, the Matrix Metalloproteinase (MMP) family of enzymes are useful, and may include MMP-1, MMP-12, MMP-13, MMP-2, MMP-3, MMP-7, MMP-8, and MMP-9.

Other markers include cancer biomarkers, e.g., combinations of alpha-fetoprotein, PSA, cancer antigen 125, and carcinoembryonic antigen; cardiac markers, e.g., combinations of creatine kinase-MB, endothelin 1, PAP, SGOT, and TIMP-1; and markers for Alzheimer's disease.

Allergens, e.g., multi-analyte allergy-testing applications, may use, e.g. different allergens, which serve as targets for allergen-specific antibodies; a second label molecule completes the reaction, using anti-human-IgE. Exemplary allergens for such panels include Alternaria (Mold), Bermuda Grass, Cat Dander, Egg White, Milk, Mite Ptemoyssinus, Mountain Cedar, Short Ragweed, Timothy Grass, and Wheat (food). Similar procedures may be used to detect, e.g., autoimmune antibodies, using antigens such as ASCA, beta-2 Microglobulin, Centromere B, Chromatin, ENA Profile 4 (SSA, SSB, Sm, RNP), ENA Profile 5 (SSA, SSB, Sm, RNP, Scl-70), ENA Profile 6 (SSA, SSB, Sm, RNP, Scl-70, Jo-1), Histone, Histone H1, Histone H2A, Histone H2B, Histone H3, Histone H4, HSP-27 pS82, HSP-27 Total, HSP-32, HSP-65, HSP-71, HSP-90 a, HSP-90 b, Jo-1, PCNA, PR3, (cANCA), Ribosomal P, RNP, RNP-A, RNP-C, SCF, Scl-70, Serum Amyloid P, SLE Profile 8 (SSA, SSB, Sm, RNP, Sc1-70, Jo-1, Ribosome-P, chromatin), Sm, Smith, SSA, SSB, Streptolysin O, and TPO.

Still other markers may be used to assay for angiogenesis (e.g., human angiogenesis), and may include, by way of example, combinations of IL-8, bFGF, VEGF, angiogenin, and TNF. Other panels may be used to assay for cell activation (e.g., human cell activation), and may include, by way of example, combinations of IL-8, βFGF, VEGF, angiogenin, and TNF; panels for B cell activation (e.g., human B cell activation), may include, by way of example, combinations of CD79b(Igβ), BLNK, Btk, Syk, and PLCγ, panels for T cell activation (e.g., human T cell activation), may include, by way of example, combinations of TCRz, SLP-76, ZAP-70, Pyk2, Itk, and PLCγ.

Markers of inflammation, e.g., human inflammation, may include, e.g., combinations of 11-8, IL-1β, IL6, IL10, TNF, and IL-12p70, as well as other cytokines or biomarkers that will be apparent to those of skill in the art. Panels for chemokines (e.g., human chemokines), may include, by way of example, combinations of IL-8, RANTES, KC (mouse), monokine-induced by interferon-γ, monocyte-chemoattractant protein-1, macrophage inflammatory protein 1-α, macrophage inflammatory protein 1-β and interferon-γ-induced protein 10. Panels for apoptosis (e.g., human apoptosis), may include, by way of example, combinations of cleaved PARP, Bcl-2, and active caspase-3 protein. Panels for human anaphylotoxins may include, by way of example, combinations of anaphylotoxins C4a, 3a, and 5a. Panels for allergy mediators (e.g., human allergy mediators), may include, by way of example, combinations of IL-3, IL-4, IL-5, IL-7, IL-9 (mouse), IL-10, IL-13 (mouse), eotaxin (CCL11) granulocyte colony stimulating factor, and granulocyte macrophage colony-stimulating factor.

For both research and diagnostics, cytokines are useful as markers of a number of conditions, diseases, pathologies, and the like. There are currently over 100 cytokines/chemokines whose coordinate or discordant regulation is of clinical interest. Exemplary cytokines that are presently used in marker panels and that may be used in methods and compositions of the invention include, but are not limited to, BDNF, CREB pS133, CREB Total, DR-5, EGF, ENA-78, Eotaxin, Fatty Acid Binding Protein, FGF-basic, G-CSF, GCP-2 GM-CSF, GRO-KC, HGF, ICAM-1, IFN-alpha, IFN-gamma, IL-10, IL-11, IL-12, IL-12 p40, IL-12 p40/p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, IP-10, JE/MCP-1, KC, KC/GROa, LIF, Lymphotacin, M-CSF, MCP-1, MCP-1(MCAF), MCP-3, MCP-5, MDC, MIG, MIP-1 alpha, MIP-1 beta, MIP-1 gamma, MIP-2, MIP-3 beta, OSM, PDGF-BB, RANTES, Rb (pTS21), Rb (total), Rb pSpT249/252, Tau (pS214), Tau (pS396), Tau (total), Tissue Factor, TNF-alpha, TNF-beta, TNF-RI, TNF-RII, VCAM-1, VEGF.

Endocrine markers, e.g., for diabetes or thyroid markers, are useful in the clinical laboratory or for the life-science researcher. Exemplary endocrine markers include Adiponectin, Amylin, C-Peptide, Calcitonin, CRF, FGF-9, GLP-1, Glucagon, Growth Hormone, Insulin, Leptin, Lipoprotein (a), Resistin, T3, T4, TBG, Thyroglobulin, and TSH. Metabolic markers are also useful for research or clinical applications, and may include Apolipoprotein A-1, Apolipoprotein A-I, Apolipoprotein A-II, Apolipoprotein B, Apolipoprotein C-II, Apolipoprotein C-III, Apolipoprotein E, beta-2 Glycoprotein, Collagen Type 1, Collagen Type 2, Collagen Type 4, Collagen Type 6, Glutathione S-Transferase, Pancreatic Islet Cells, and tTG (Celiac Disease).

Pregnancy markers may comprise, e.g., tests for human chorionic gonadotropin, hepatitis B surface antigen, rubella virus, alpha fetoprotein, 3' estradiol, and other substances of interest, in a pregnant individual.

It will be appreciated that the sensitivity of the analyzers of the invention allow the design and implementation of markers and panels of markers not hitherto possible, in order to determine, not only simple yes/no answers as to the presence of abnormal levels of markers for, e.g., tumors or genetic abnormalities, but much more refined analysis, such as earlier determination of the onset of a condition, and more precise comparison between normal ranges of markers and the levels found in an individual. Present assay methods often allow the detection of a marker only when the underlying pathological condition to which it corresponds has reached a stage where treatment is unlikely to be effective or only marginally effective. For example, present levels of detection for many cancers allow detection only at levels where the cancer is far advanced. Another example is the detection of cardiac troponin I, as detailed in the Examples. The methods of the invention allow not only earlier detection, but also establishment of baseline levels for normal individuals for those markers that are present in normal individuals but for which abnormally high or low levels indicate the presence of pathology Accordingly, the present invention encompasses methods of early detection of disease or pathology, based on the detection and/or quantitation of one or more biomarkers. Typically, the concentration of a biomarker in a sample, e.g., a blood, plasma, or serum sample, from an individual, e.g., a human, is compared with values that are considered normal or abnormal. The analyzers and analyzer systems of the invention may be used to determine levels of biomarkers for both normal and diseased populations that are far lower than those presently used in detection and diagnosis, e.g., levels that are 0.1, 0.01, 0.001, or 0.0001× the levels presently quantifiable. Thus, a database may be created for normal and abnormal levels for a given condition, and individuals may be screened and the condition detected much earlier than has heretofore been possible. Alternatively, databases may already exist for normal and abnormal values but present methods may not be practical for screening individuals on a routine basis to determine with sufficient sensitivity whether the value of the individual for the marker is within the normal range. For example, most present methods for the determination of IL-6 concentration in a sample are capable of detecting IL-6 only down to a concentration of about 5 pg/ml; the normal range of IL-6 values is about 1 to about 10 pg/ml; hence, present methods are able to detect IL-6 only in the upper part of normal ranges. In contrast, the analyzers and analyzer systems of the invention allow the detection of IL-6 down to a concentration below about 01 pg/ml, or less than one-tenth of normal range values. Thus, the analyzers and analyzer systems of the invention allow a far broader and more nuanced database to be produced for a biomarker, e.g., for IL-6, and also allow screening for that biomarker both within and outside of the normal range, allowing earlier detection Such early detection methods of the invention may be used for the detection of any disease or condition for which one or more biomarkers exist or may be found that correlate with onset or progression of the condition, and for which a database of values may be obtained As one example, diagnosis of cancers often depends on the use of crude measurements of tumor growth, such as visualization of the tumor itself, that are either inaccurate or that must reach high levels before they become detectable, e.g., in a practical clinical setting by present methods. At the point of detection, the tumor has often grown to sufficient size that intervention is unlikely to occur before metastasis. For example, detection of lung cancer by X-ray requires a tumor of >1 cm in diameter, and by CT scan of >2-3 mm. Alternatively, a biomarker of tumor growth may be used, but, again, often the tumor is well-advanced by the time the biomarker is detectable at levels accessible to current clinical technology. Furthermore, after intervention (e.g., surgery, chemotherapy, or radiation to shrink or remove the tumor or tumors), it is often not possible to measure the tumor marker with sufficient sensitivity to determine if there has been a recurrence of the cancer until residual disease has progressed to the point where further intervention is unlikely to be successful. Using the analyzers, systems, and methods of the present invention, it is possible to both detect onset of tumor growth and return of tumor growth at a point where intervention is more likely to be successful, e.g., due to lower probability of metastasis.

Hence, the present invention provides 1) methods of screening for biomarkers that heretofore have been present at levels too low to be useful for diagnosis or monitoring of disease; 2) methods of screening for onset of disease based on the detection of biomarkers, either discovered in 1) or presently known, at levels far lower than is now possible; and 3) methods for monitoring the course of treatment or the usefulness of experimental treatments, with far greater ability to detect effects, including recurrence of disease, than is presently possible These include a method for testing an individual for the presence, absence, likelihood of developing, or degree of progression of a condition. The condition may be pathological or non-pathological (e.g., aging, pregnancy). Exemplary pathological conditions include general pathological conditions, such as inflammation, which is linked to a number of specific pathological conditions such as diabetes, heart disease, arthritis, cancer, and the like. Pathological conditions also include more specific conditions, including, but not limited to, cancers, inflammatory conditions and/or autoimmune diseases, cardiovascular disease, gastrointestinal disease, skin disease, neurological disorders, genetic disorders, infectious diseases, aging, allergies, and the like. Cancers include, but are not limited to, cancer of the lung, stomach, pancreas, esophagus, ovary, breast, prostate, bladder, colon, and rectum. The method includes analyzing a sample from an individual for one or more markers of the condition using an analyzer or analyzer system of the invention, where the analyzer or analyzer system is capable of detecting the marker or markers at a level of less than 1 nanomolar, or 1 picomolar, or 1 femtomolar, or 1 attomolar, or 1 zeptomolar. In some embodiments, the analyzer or analyzer system is capable of detecting a change in concentration of the marker or markers from one sample to another sample of less than about 0.1, 1, 2, 5, 10, 20, 30, 40, 50, 60, or 80% when the biomarker is present at a concentration of less than 1 nanomolar, or 1 picomolar, or 1 femtomolar, or 1 attomolar, or 1 zeptomolar, and when the size of the sample is less than about 100, 50, 40, 30, 20, 10, 5, 2, 1, 0.1, 0.01, 0.001, or 0.0001 ul. The method can further include comparing the value obtained in the analysis with known values for the biomarker to determine presence, absence, or degree of progress of the condition; further, the method can include informing the individual of the results of the comparison, or determining a course of treatment, prognosis, or diagnosis based on said comparison. In some embodiments, the method includes analyzing multiple samples from an individual, often taken over a course of time, and determining the degree of change and/or rate of change of the concentration of the marker or markers for the particular condition being tested, and comparing the degree and/or rate of change with normal and/or abnormal values. It will be appreciated that combinations of absolute values and rates of change, etc., may also be used in increasing levels of sophistication in determining the presence, absence, or progress of a condition.

In addition, the methods of the invention allow the discovery and use of panels of biomarkers with increased sensitivity to determine, e.g., results of treatment and/or outcome of testing of treatments. For example, in cancer treatment involving methods to reduce or eliminate cancerous tissue, it is useful to know if and when the cancer is returning, and at what rate. The sensitivity of the present methods allows such information to be available at a much earlier stage of return and at a much higher level of precision, thus allowing action to be taken at an earlier stage in the return of the disease. The same is true, of course, for screening of the onset of disease in previously normal individuals.

Because the methods of the invention provide increased sensitivity and the ability to multiplex samples, the size of the sample required in the methods can be correspondingly reduced. In some embodiments of the invention wherein the sample is a biological fluid, e.g., a body fluid (for example, serum), the sample size can be less than 1000, 500, 200, 100, 75, 50, 40, 30, 20, 10, 5, 4, 3, 2, 1, 0.1, 0.01, 0.001, or 0.0001 ul. The number of different types of particles that may be analyzed on such a sample may be 1, or more than 1, 2, 3, 4, 5, 6, 7, 8, 9, 10, 15, 20, 30, 40, 50, 100, or more than 100. In some embodiments, the sample size is about 1 ul to about 500 ul, or about 10 ul to about 200 ul, or about 10 ul to about 100 ul, or about 10 ul to about 50 ul, or about 50 ul, and the number of particle types analyzed is about 1 to about 50, or about 1 to about 20, or about 1 to about 10.

In some embodiments, the analysis of a sample occurs within a certain time period. In some cases, the analysis is performed within about one day, or within about 12, 8, 4, 2, 1, 0.5, 0.4, 0.3, 0.2, 0.1, 0.05, 0.01, or less than 0.01 hour. In embodiments, the invention provides methods of analyzing a plurality of samples using a single particle detector with two interrogation spaces, wherein on average each sample is analyzed in less than 1 hour, or less than 0.5 hour, or less than 0.2 hour, or less than 0.1 hour, or less than 5, 4, 3, 2, 1, 0.5 or 0.1 minute. In one embodiment, the invention provides a method for analyzing clinical samples using a single particle detector with two interrogation spaces, wherein on average each sample is analyzed in less than 1, or less than 0.5, or less than 0.1 hour.

In one embodiment, the invention provides a method of determining whether or not an individual is suffering from a disease, comprising analyzing a sample from the individual for the presence, absence, or concentration of biomarkers using a single particle detector as described herein, wherein the analysis of the sample is performed in less than 2 hours, or 1 hour, or 0.5 hour, or 0.25 hour, 0.1, or 0.01 hour. The method may include obtaining the sample from the individual and/or reporting the results of the analysis to the individual.

In some embodiments, the detection of the presence, absence, and/or concentration of the particle(s) is reported to the individual from whom the sample was taken, or to a health professional caring for the individual from whom the sample was taken. In some embodiments, a diagnosis, prognosis, monitoring, and/or suggested course of treatment, based on the presence, absence, and/or concentration of the particle(s) is made. In some embodiments, the diagnosis, prognosis, monitoring and/or suggested course of treatment is reported to the individual from whom the sample was taken, their representative or to a health professional caring for the individual from whom the sample was taken.

It will be appreciated that the methods of the invention also provide the ability to provide individuals, such as researchers or health professionals, with information with which to evaluate research or clinical or pre-clinical trials. For example, the availability of genetic information and association of disease with mutation(s) of critical genes has generated a rich field of research and clinical analysis. Both genetic information (i.e., analysis of nucleic acids to determine genetic variability) and proteomic information (i.e., analysis of actual proteins to determine expression of genetic variability) are useful in both research and clinical settings. In general, methods of research or diagnosis based on information about mutation of critical genes have required the use of the polymerase chain reaction (PCR) and its variants. The sensitivity of the present methods allow detection of mutational events, either from nucleic acid, or protein, or both, without the necessity of amplification of the nucleic acid. Furthermore, changes in the presence, absence, and/or concentrations of a number of proteins, whose expression is associated with a particular genetic configuration and/or pathological condition may be readily detected by the methods of the invention, allowing rapid and sensitive screening of, e.g., the effects of agents being tested for an effect on a pathological condition. A number of different markers, e.g. proteins, may be simultaneously detected and/or quantitated in a single sample.

Additional industrial and environmental applications of the present invention include manufacturing process control, environmental monitoring and food safety. For example, samples from an environmental source such as soil, water, or air; or from an industrial source such as a waste stream, a water source, a supply line, or a production lot can be analyzed for contamination. Examples of likely contaminants include pesticides, petroleum products, industrial fallout, and organisms. Many of the same contaminants are a concern in the food supply, but especially organisms such as fungi in grain and bacteria in meat, game, produce, or dairy products. Industrial applications include quality control of fermentation media, such as from a biological reactor or food fermentation process such as brewing.

In a further aspect, the invention provides business methods. In one embodiment, the invention provides a method of doing business comprising use by an entity of a detector with two interrogation spaces that is capable of detecting single particles (e.g., single molecules) to obtain a result for an assay of a sample, reporting said result, and payment to the entity for the reporting of the result. In some embodiments, the detector may be any of the embodiments described herein. In some embodiments, the entity is a Clinical Laboratory Improvement Amendments (CLIA) laboratory. In some embodiments, the entity is a laboratory that is not a CLIA laboratory. The sample may be any type of sample capable of being analyzed by the single particle detector. In some embodiments, the sample is from an individual. The individual may be any type of individual as described herein. In some embodiments, the individual is a patient (e.g., animal, e.g., human) for which screening, diagnosis, prognosis, monitoring and/or determination of method of treatment is desired. In some embodiments, the individual is an individual (e.g. animal, e.g. human) who is participating in a clinical trial or in pre-clinical trial research. In some embodiments, the sample is from an individual who is part of a research project, e.g., biomedical research, agricultural research, industrial research, educational research, bioterrorism research, and the like. In some embodiments, payment may be by the individual receiving the report of the result, e.g., a health care professional and/or the individual from whom the sample was taken, to the entity performing the analysis, e.g., a CLIA laboratory, or it may be by the individual from whom the sample was taken to the individual receiving the report from the entity performing the analysis, or to the entity itself, or both, or some combination thereof. In another embodiment, the invention provides a method of doing business, comprising use of a detector as described herein that is capable of detecting single particles by a health-care provider to obtain a result for an assay of a sample from an individual, reporting said result to the individual or their representative; and payment by the individual for said reporting of the result.

EXAMPLES

The following examples are offered by way of illustration and not by way of limiting the remaining disclosure.

Example 1

Sandwich Assays for Biomarkers

Recent reports have established TREM-1 as a biomarker of bacterial or fungal infections (see, e.g., Bouchon et al. (2000) J. Immunol. 164:4991-5; Colonna (2003) Nat. Rev. Immunol. 3:445-53; Gibot et al. (2004) N. Engl. J. Med. 350:451-8; Gibot et al. (2004) Ann. Intern. Med. 141:9-15. Assays for TREM-1 have been developed using a sandwich assay format (Sandwich Assay for Detection of Individual Molecules, U.S. Provisional Patent Application No. 60/624,785). Assay reagents for TREM-1 detection are available commercially (R&D Systems, Minneapolis, Minn.). The assay was done in a 96 well plate. A monoclonal antibody was used as the capture reagent, and either another monoclonal or a polyclonal antibody was used for detection. The detection antibody was labeled with AlexaFluorA647®.

The assay protocol was as follows:
1. Coat plates with the capture antibody, washed 5×,
2. Block in 1% BSA, 5% sucrose in PBS,
3. Add the target diluted in serum, incubate, wash 5×,
4. Add the detection antibody, incubate, wash 5×
5. Add 0.1 M glycine pH 2.8 to release the bound assay components from the plate.
6. Transfer samples from the processing plate to the detection plate, bring the pH of the sample to neutral and run on the single particle analyzer system, as described herein.

Figure 9:
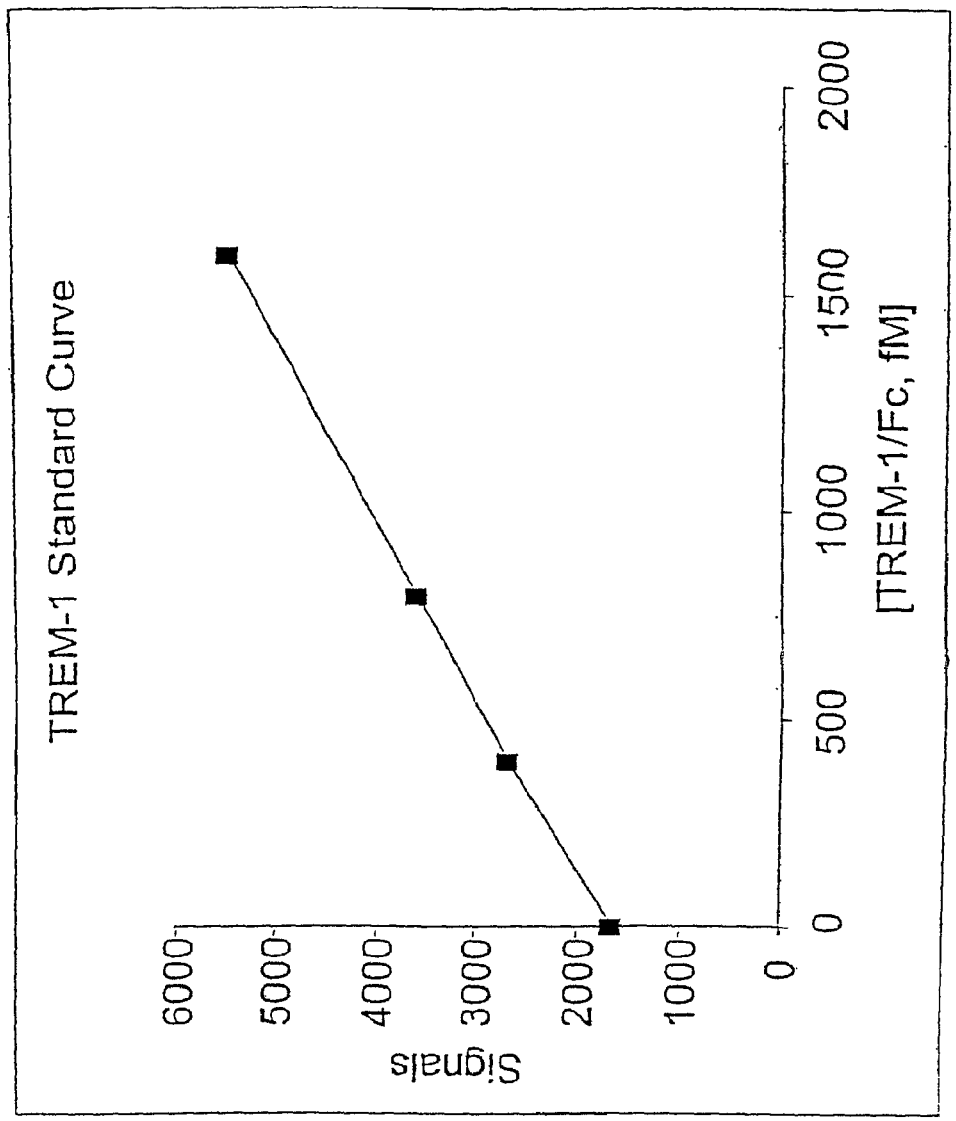
FIG. 9. Standard curve of TREM-1 measured in a sandwich molecule immunoassay developed for the single particle analyzer system. The linear range of the assay is 100-1500 fM.

FIG. 9 shows a standard curve of TREM-1 generated using the assay. The assay was linear in the measured range of 100-1500 femtomolar. An ELISA assay from R&D Systems has recently been introduced. The standard curve reported for their ELISA assay is between 60-4000 pg/mil. This Example suggests we can routinely measure 100 fM (4.7 pg/ml) in a standard curve, allowing for about 10× more sensitive measurements.

Figure 10:
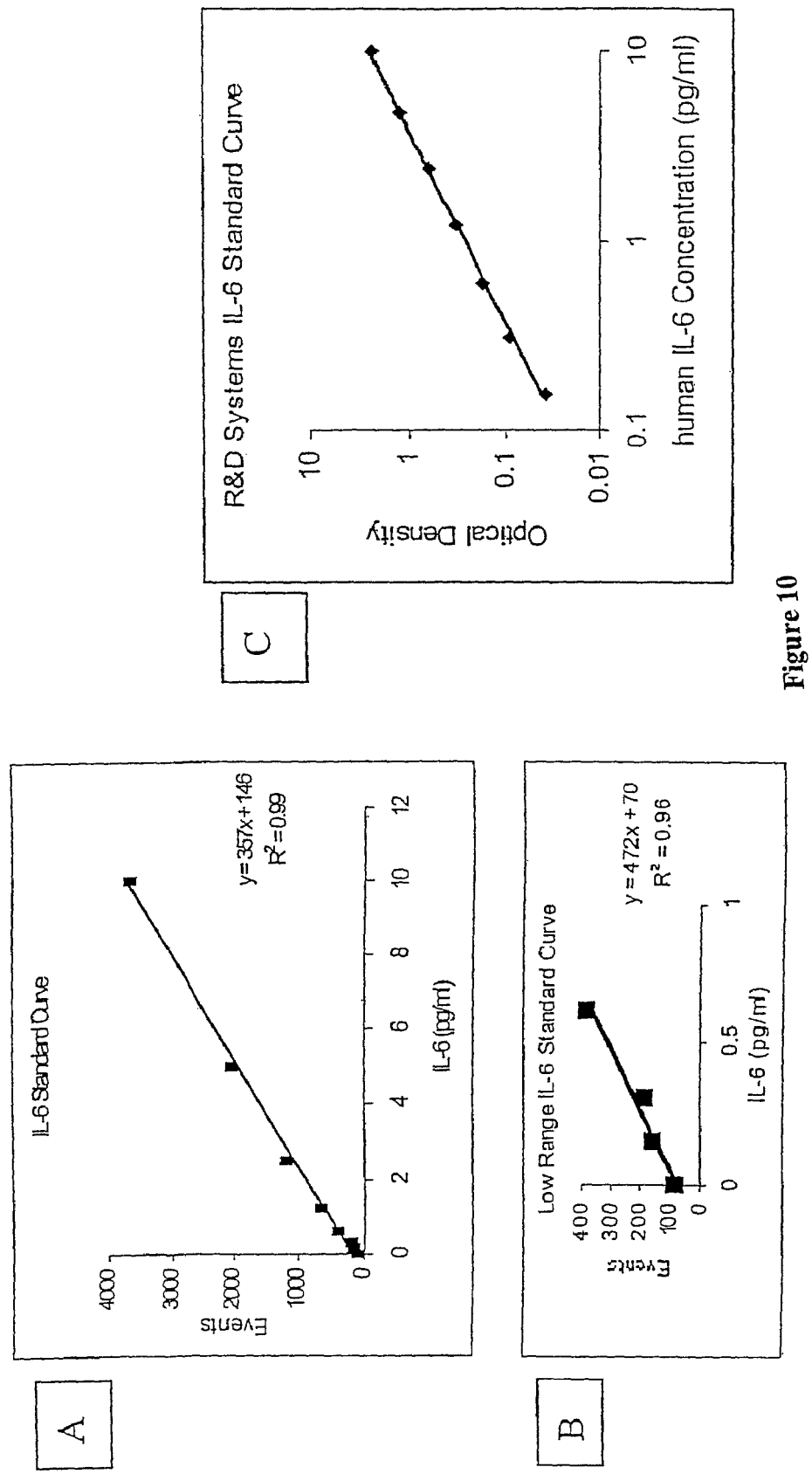
FIG. 10A-D. Standard curve for IL-6. A) IL-6 standards, diluted according to the R&D Systems kit, gave a linear response between 0.1 and 10 pg/ml. B) IL-6 standard curve below 1 pg/ml. C) Standard curve for IL-6 from R&D Systems product literature for an assay that uses two signal amplification steps. D) IL-6 standards assayed according to the sandwich immununoassay of one embodiment of the invention, using detection antibodies fluorescently labeled with AlexaFluor 647, linear response over 3.5 logs.
Figure 10D:
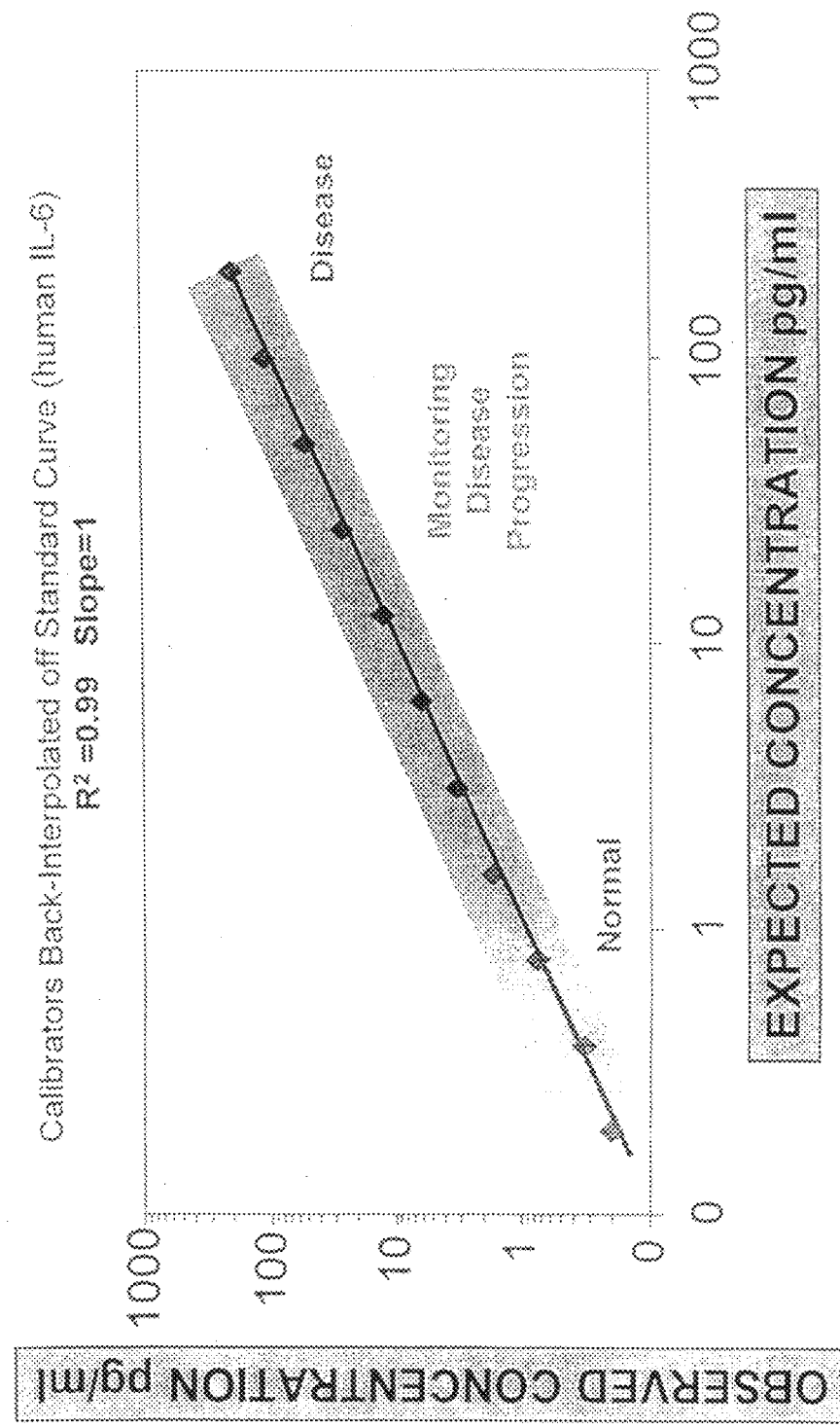

A sandwich assay configured for detection of IL-6 has also been developed using commercially available reagents (R&D Systems). The protocol was essentially as described above for TREM-1 except that the target diluent and capture antibody pair were as described by R&D Systems. The detection antibody was an R&D Systems' antibody labeled with AlexaFluor® 647. The assay allowed for detection of IL-6 at less than 0.5 pg/ml (FIGS. 10A and B). The limit of detection was calculated to be 0.06 pg/ml. This level of sensitivity is excellent for detection of even normal levels of IL-6 which range between 0.5 and 10 pg/ml. Compared to other commercially available multiplexed assays that include IL-6, this system provides a significant improvement in the level of detection. Compared to the R&D Systems assay, the limit of detection is about the same (FIG. 10C), but this system offers the advantage of multiplexing and is not dependent on amplification steps, two of which are needed for the R&D Systems' assay. The single particle analyzer system data differs from ELISA data in that quantification is accomplished by counting individual molecules in low concentration solutions, rather than making ensemble measurements of molecules. The former is more precise than the latter.

Example 2

Bead-Based Assay

Figure 11:
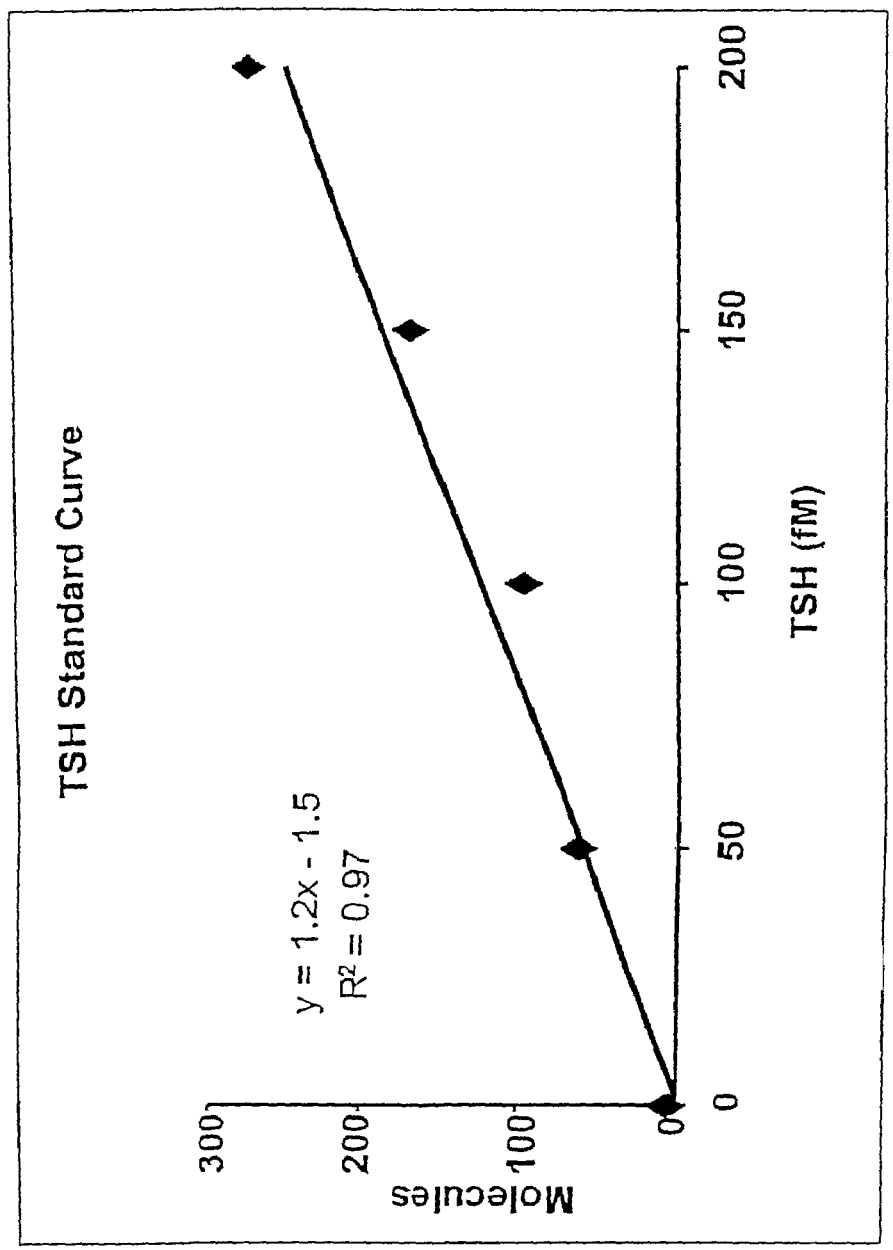
FIG. 11. Standard curve of TSH detection in a bead-based molecule immunoassay. The target molecule was captured on beads and bound to detection antibody. The beads were used to immobilize the target while unbound material was removed.

The assay described above use the same microtiter plate format where the plastic surface is used to immobilize target molecules. The single particle analyzer system also is compatible with assays done in solution using microspheres or beads to achieve separation of bound from unbound entities. FIG. 11 shows the results of a bead-based assay to detect Thyroid Stimulating Hormone (TSH). The data illustrate that the sandwich assay can be directly transferred to a bead-based format and used with the system. Super-paramagnetic streptavidin microbeads (Miltenyi Biotec, Auburn, Calif.) were coated with biotinylated anti-TSH capture antibody. Dilutions of 0-200 fM TSH were captured by incubation at 4° C. with excess microbeads in phosphate buffered saline. The microbeads, with captured TSH, were collected and washed on high gradient magnetic separation columns (Miltenyi Biotec). The beads were removed from the columns and incubated with anti-TSH detection antibody labeled with AlexaFluor® 647 (Molecular Probes, Eugene, Oreg.) for two hours at 37° C. The beads, with detection antibody bound to the captured TSH, were collected, washed with phosphate buffered saline, and removed from the column. The beads were run on the particle analysis system producing a linear response over the measured range of 50-200 femtomolar TSH (FIG. 11) when samples were run on an instrument such as that described in FIG. 1A. It will be appreciated that a similar approach can be used in which labeled detection antibody is released from the beads, either alone or attached to the TSH or other protein of interest, and run through the analyzer, without bead attached.

Example 3

Detection of a Target Protein in Human Serum

Figure 12:
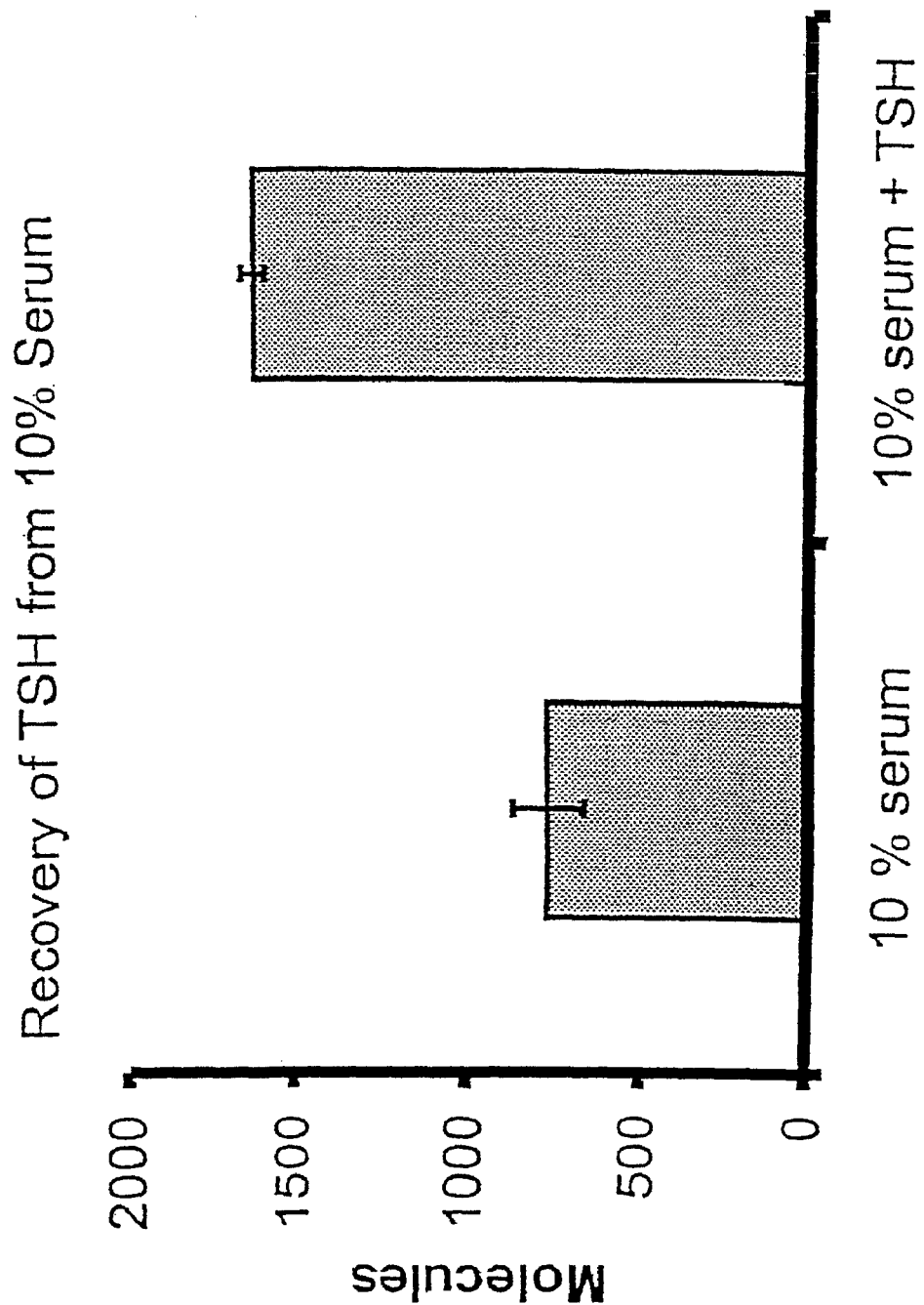
FIG. 12. TSH was added to samples that contain 10% human serum. The samples were used in a sandwich capture assay for TSH and run on the single particle analyzer system. In this assay the recovery was calculated at 108%.

A sandwich assay similar to those described above was developed for detecting targets within serum. For this assay, known quantities of TSH were added to samples that contained 10% human serum. Labeled antibodies specific for TSH were added, unbound label removed, and the samples were run on the single particle analyzer system. The results, shown in FIG. 12, demonstrate that all the added TSH was recovered in the assay.

Example 4

Indirect Detection of Particles—Detection of Labels Released from the Target Particle Biotinylated anti-thyroid stimulating hormone (TSH) antibody was immobilized on a streptavidin-coated 96 well plate, and the excess unbound antibody was washed away. TSH antigen and A647 labeled anti-TSH antibody were added to the wells in phosphate buffered saline with 1% bovine serum albumin and 0.1% Tween®20. The plate was incubated with agitation. The liquid was removed by aspiration, and the wells were washed three times. The A647 labeled antibody was dissociated from the TSH sandwich by incubation with 0.1 M glycine-HCl, pH 2.8. The free A647 labeled antibody was collected, diluted and analyzed by SMD. The linear relationship between released label and the original target particle concentration is seen in FIG. 13A.

Figure 13:
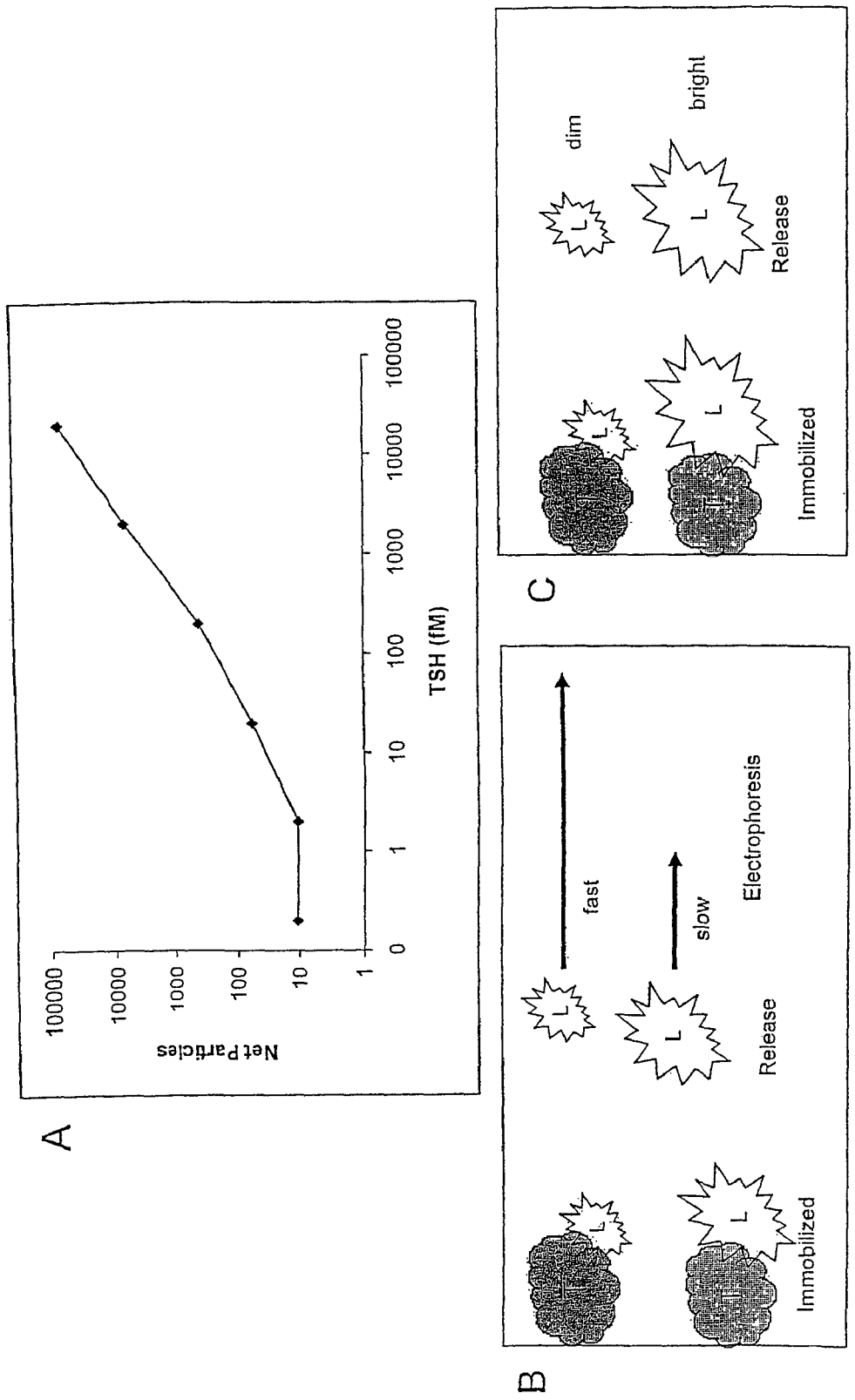
FIG. 13A-C. Discrimination of labels released from protein target and nucleic acid targets. A) Detection of label released from a protein target. Thyroid stimulating hormone (TSH) was immobilized on a 96 well plate and labeled with A647 labeled anti-TSH. Unbound reagents were removed by washing. The A647 labeled antibody was dissociated from the TSH and measured in the SMD. A linear relationship was observed between the net particles of A647 measured and the original TSH concentration. B) Prophetic representation of discrimination of released labels based on their electrophoretic mobility. C) Prophetic representation of discrimination of released labels based on their fluorescence intensity.

It will be appreciated by one skilled in the art that similar methods are available for labeling and release of labels from nucleic acids. Matray et al. teaches methods for labeling and releasing labels from both proteins and nucleic acids (Matray, 2004). One skilled in the art will also recognize that separation and discrimination of a mixture of labels released from the target proteins and nucleic acids is essentially the same as for the original targets. FIGS. 13 B and C shows two possible ways to distinguish two released labels using the analyzer.

Example 5

Sandwich Assays for Biomarkers: Cardiac Troponin I (cTnI)

Figure 15:
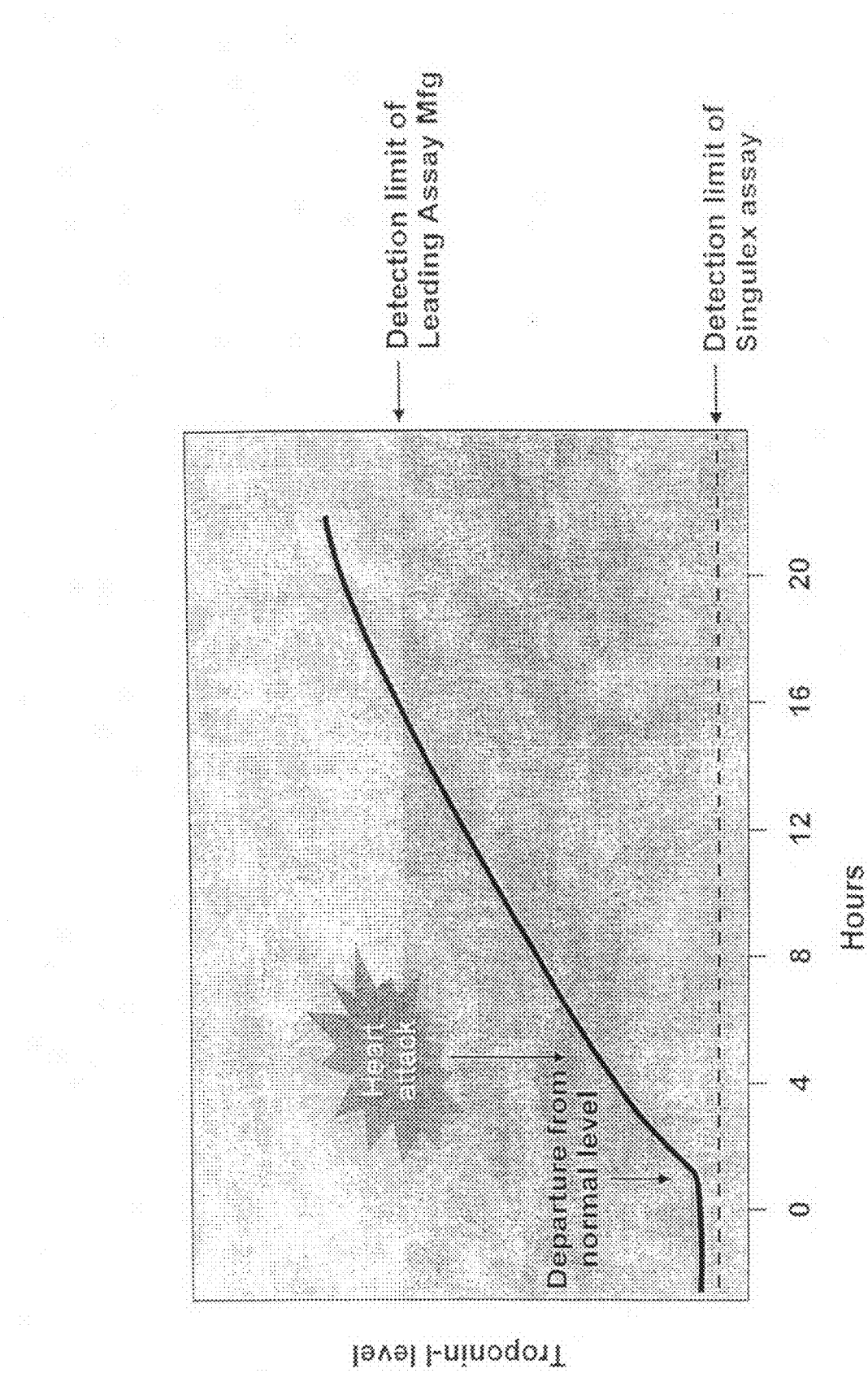
FIG. 15. Detection limits for cardiac troponin I of current leading assay and assay of the invention.

Cardiac troponin, especially cardiac troponin I (cTnI), is a protein that is released from cardiac muscle on injury or ischemia. At present, the detection levels of typical commercial assays are not sufficiently sensitive to detect cTnI at levels that would allow detection of departure from normal level, e.g., pre-heart attack or early after a heart attack (FIG. 15). The next Examples detail more sensitive assay of cardiac troponin I using the methods of the invention.

Unless otherwise specified, processing samples in the Examples were analyzed in a single molecule detector (SMD) as described herein, with the following parameters: Laser: continuous wave gallium arsenite diode laser of wavelength 639 nm (Blue Sky Research, Milpitas, Calif.), focused to a spot size of approximately 2 microns (interrogation space of 0.004 pL as defined herein; however, this size can be altered, e.g., to 0.1 pL or larger); flow rate=5 microliter/min through a fused silica capillary of 100 micron square ID and 300 micron square OD; non-confocal arrangement of lenses (see, e.g., FIG. 1A); focusing lens of 0.8 numerical aperture (Olympus); silicon avalanche photodiode detector (Perkin Elmer, Waltham, Mass.).

The assay: The purpose of this assay was to detect the presence of cardiac Troponin I (cTNI) in human serum. The assay format was a two-step sandwich immunoassay based on a mouse monoclonal capture antibody and a goat polyconal detection antibody. Ten microliters of sample were required. The working range of the assay is 0-900 pg/nil with a typical analytical limit of detection of 1-3 pg/ml. The assay required about four hours of bench time to complete.

Materials: the following materials were used in the procedure described below: Assay plate: Nunc Maxisorp, product 464718, 384 well, clear, passively coated with monoclonal antibody, BiosPacific A34440228P Lot # A0316 (5 μg/ml in 0.05 M sodium carbonate pH 9.6, overnight at room temperature); blocked with 5sucrose, 1% BSA in PBS, and stored at 4° C. For the standard curve, Human cardiac Troponin I (BiosPacific Cat #J34000352) was used. The diluent for the standard concentrations was human serum that was immonodepleted of endogenous cTNI, aliquoted and stored at −20° C. Dilution of the standards was done in a 96 well, conical, polypropylene, (Nunc product #249944). The following buffers and solutions were used: (a) assay buffer: BBS with 1% BSA and 0.1% TritonX-100; (b) passive blocking solution in assay buffer containing 2 mg/ml mouse IgG, (Equitech Bio); 2 mg/ml goat IgG, (Equitech Bio); and 2 mg/ml MAK33 poly, Roche#11939661; (c) detection Antibody (Ab): Goat Polyclonal antibody affinity purified to Peptide 3, (BiosPacific G129C), which was label with a fluorescent dye AlexaFluor 647, and stored at 4° C.; detection antibody diluent: 50% assay buffer, 50% passive blocking solution; wash buffer: borate buffer saline Triton Buffer (BBST) (1.0 M borate, 15.0 M sodium chloride, 10% Triton X-100, pH 8.3); elution buffer: BBS with 4M urea, 0.02% Triton X-100 and 0.001% BSA.

Preparation of AlexaFluor 647 labeled antibodies: the detection antibody G-129-C was conjugated to AlexaFluor 647 by first dissolving 100 ug of G-129-C in 400 uL of the coupling buffer (0.1M NaHCO3). The antibody solution was then concentrated to 50 ul by transferring the solution into YM-30 filter and subjecting the solution and filter to centrifugation. The YM-30 filter and antibody was then washed three times by adding 400 ul of the coupling buffer. The antibody was recovered by adding 50□l to the filter, inverting the filter, and centrifuging for 1 minute at 5,000×g. The resulting antibody solution was 1-2 ug/ul. AlexaFluor 647 NES ester was reconstituted by adding 20 ul DMSO to one vial of AlexaFluor 647, this solution was stored at −20° C. for up to one month. 3 ul of AlexaFluor 647 stock solution was added to the antibody solution, which was then mixed and incubated in the dark for one hour. After the one hour, 7.5 ul 1M tris was added to the antibody AlexaFluor 647 solution and mixed. The solution was ultrafiltered with YM-30 to remove low molecular weight components. The volume of the retentate, which contained the antibody conjugated to AlexaFluor 647, was adjusted to 200-400 ul by adding PBS. 3 ul 10% NaN3 was added to the solution, the resulting solution was transferred to an Ultrafree 0.22 centrifugal unit and spun for 2 minutes at 12,000×g. The filtrate containing the conjugated antibody was collected and used in the assays.

Procedure: cTnI standard and sample preparation and analysis:

The standard curve was prepared as follows: working standards were prepared (0-900 pg/mil) by serial dilutions of the stock of cTnI into standard diluent or to achieve a range of cTnI concentrations of between 1.2 pg/ml-4.3 µg/ml.

10 µl passive blocking solution and 10 µl of standard or of sample were added to each well. Standards were run in quadruplicate. The plate was sealed with Axyseal sealing film, centrifuged for 1 min at 3000 RPM, and incubated for 2 hours at 25° C. with shaking. The plate was washed five times, and centrifuged until rotor reached 3000 RPM in an inverted position over a paper towel. A 1 nM working dilution of detection antibody was prepared, and 20 µl detection antibody were added to each well. The plate was sealed and centrifuged, and the assay incubated for 1 hour at 25° C. with shaking. 30 µl elution buffer were added per well, the plate was sealed and the assay incubated for ½ hour at 25° C. The plate was either stored for up to 48 hours at 4° C. prior to analysis, or the sample was analyzed immediately.

For analysis, 20 µl per well were acquired at 40 µl/minute, and 5 µl were analyzed at 5 µl/minute. The data were analyzed based on a threshold of 4 sigma. Raw signal versus concentration of the standards was plotted. A linear fit was performed for the low concentration range, and a non-linear fit was performed for the full standard curve. The limit of detection (LoD) was calculated as LOD=(3×standard deviation of zeros)/slope of linear fit. The concentrations of the samples were determined from the equation (linear or non-linear) appropriate for the sample signal.

An aliquot was pumped into the analyzer using an automatic sampling system is capable of automatically and sequentially sampling a plurality of processed samples from a multiwell container; including a source of negative pressure to draw a portion of the sample into a sampling port that was inserted into the sample, and a flow channel that provides a fluid communication between the sampling port and a detection channel of the single molecule analyzer. Individually-labeled antibodies were measured during capillary flow by setting the interrogation volume such that the emission of only 1 fluorescent label was detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention was determined by the mean+3 SD method.

Results: Data for a typical cTnI standard curve measured in quadruplicate using the assay protocol is shown in Table 2 and FIG. 16.

TABLE 2

Standard Curve for cTnI

| cTnI (pg/ml) | Signal | Standard Deviation | % CV |
|---|---|---|---|
| 0 | 233 | 25 | 10.8 |
| 1.5625 | 346 | 31 | 8.9 |
| 3.125 | 463 | 35 | 7.5 |
| 6.25 | 695 | 39 | 5.6 |
| 12.5 | 1137 | 61 | 5.3 |
| 25 | 1988 | 139 | 7.0 |
| 50 | 3654 | 174 | 4.8 |
| 100 | 5493 | 350 | 6.4 |
| 200 | 8264 | 267 | 3.2 |
| 400 | 9702 | 149 | 1.5 |
| 800 | 9976 | 50 | 0.5 |

The sensitivity of the analyzer system was tested in 15 runs and was found routinely to detect sub femtonol/l (fM) levels of calibrator, as shown by the data in Table 3. The precision was 10% at 4 and 12 pg/ml ctnI.

TABLE 3

Instrument Sensitivity

| Calibrator (fM) | Signal counts | CV |
|---|---|---|
| 0 | 11 | |
| 12 | 302 | 9 |
| 60 | 1341 | 8 |
| 300 | 4784 | 7 |

Figure 16:
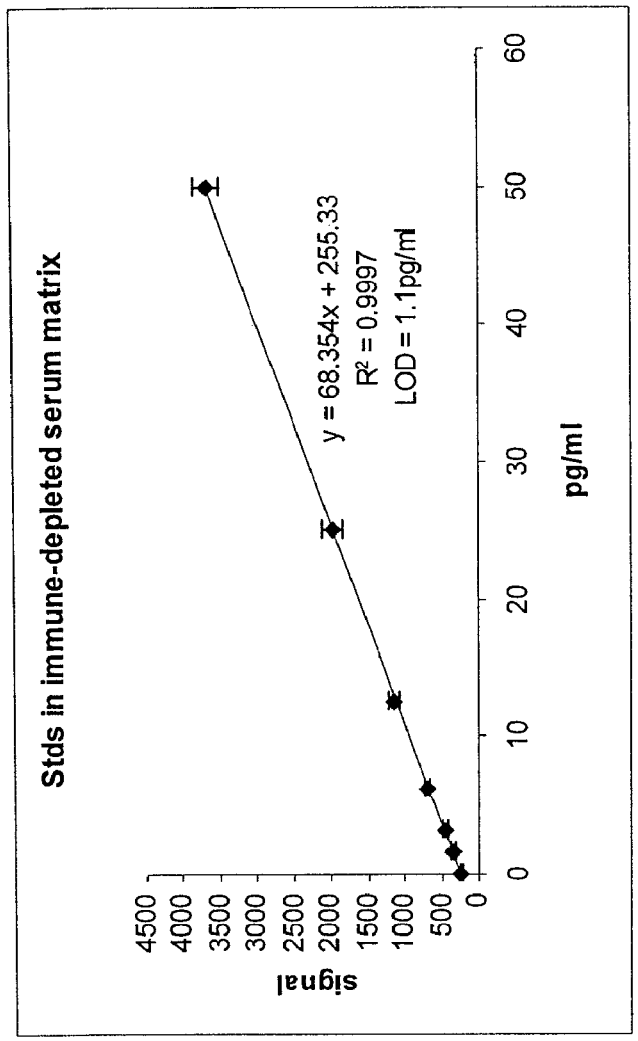
FIG. 16: Data for a typical cardiac troponin I (cTnI) standard curve measured in quadruplicate using the assay protocol described in the Examples.

Linearized standard curve for the range concentrations of cTnI are shown in FIG. 16.

The analytical limit of detection (LoD) was determined across 15 sequential assays. The LoD was the mean of the 0 std+3 SD (n=4) intra-assay determinations. The average LoD was 1.7 pg/ml (range 0.4-2.8 pg/ml).

The recovery of the sample was determined by analyzing samples of serum that had been immunodepleted of cTnI and spiked with known amounts of cTnI. Table 4 shows the data for sample recovery by the system analyzed over 3 days.

TABLE 4

Sample Recovery

| Spike (pg/ml) | Recovery (mean) | Standard Deviation | % CV |
|---|---|---|---|
| 5 | 5.7 | 0.9 | 16 |
| 15 | 13.7 | 0.2 | 2 |

TABLE 4-continued

Sample Recovery

| Spike (pg/ml) | Recovery (mean) | Standard Deviation | % CV |
|---|---|---|---|
| 45 | 43 | 0.6 | 2 |
| 135 | 151 | 6.2 | 4 |

The linearity of the assay was determined in pooled human serum that was spiked with cTnI and diluted with standard diluent. The results in 5 show the dilutions and % of the signal expected for the corresponding dilution.

TABLE 5

Assay Linearity

| Serum Dilution | % of expected |
|---|---|
| 1:2 | 79 |
| 1:4 | 87 |
| 1:8 | 96 |

These data show that the analyzer system of the invention allows for performing highly sensitive laser-induced immunoassay for sub-femtomolar concentrations of cTnI.

Example 6

Sandwich Bead-based Assays for cTnI

The assays described above use the same microtiter plate format where the plastic surface is used to immobilize target molecules. The single particle analyzer system also is compatible with assays done in solution using microparticles or beads to achieve separation of bound from unbound entities.

Materials: MyOne Streptavidin C1 microparticles (MPs) are obtained from Dynal (650.01-03, 10 mg/ml stock). Buffers use in the assay include: 10× borate buffer saline Triton Buffer (BBST) (1.0 M borate, 15.0 M sodium chloride, 10% Triton X-100, pH 8.3); assay buffer (2 mg/ml normal goat IgG, 2 mg/ml normal mouse IgG, and 0.2 mg/ml MAB-33-IgG-Polymerin 0.1 MTris (pH 8.1), 0.025 MEDTA, 0.15M NaCl, 0.1% BSA, 0.1% Triton X-100, and 0.1% NaN3, stored at 4 C); and elution buffer (BBS with 4 M urea, 0.02% Triton X-100, and 0.001% BSA, stored at 2-8 C). Antibodies used in the sandwich bead-based assay include: Bio-Ab (A34650228P (BiosPacific) with 1-2 biotins per IgG) and Det-Ab (G-129-C (BiosPacific) conjugated to A647, 2-4 fluors per IgG). The standard is recombinant human cardiac troponin I (BiosPacific, cat # J34120352). The calibrator diluent is 30 mg/ml BSA in TBS wEDTA.

Microparticles Coating: 100 ul of the MPs stock is placed in an eppendorf tube. The MPs are washed three times with 100 ul of BBST wash buffer by applying a magnet, removing the supernatant, removing the magnet, and resuspending in wash buffer. After the washes the MPs are resuspended in 100 ul of assay buffer and 15 ug of Bio-Ab are added. The mixture is then incubated for an hour at room temperature with constant mixing. The MPs are washed five times with 1 ml wash buffer as described above. After the washes the MPs are resuspended in 15 ml of assay buffer (or 100 ul to store at 4° C.).

Preparation of Standard and Samples: The standard is diluted with calibrator diluent to prepare proper standard curve (usually 200 pg/ml down to 0.1 pg/ml). Frozen serum and plasma samples need to be centrifuged 10 minutes at room temperature at 13K rpm. Clarified serum/plasma is removed carefully to avoid taking any possible pellets or floaters and put into fresh tubes. 50 ul of each standard or sample is pippetted into appropriate wells.

Capture Target: 150 ul of MPs (after resuspension to 15 ml in assay buffer+400 mM NaCl) are added to each well. The mixture is incubated on JitterBug, 5 at room temperature for 1 hr.

Washes and Detection: The plate is placed on a magnet and the supernatant is removed after ensuring that all MPs are captured by the magnet. 250 ul of wash buffer are added after removing the plate from the magnet. The plate is then placed on the magnet and the supernatant is removed after ensuring that all MPs are captured by the magnet. 20 ul Det-Ab are added per well (Det-Ab to 500 ng/ml is diluted in assay buffer+400 mM NaCl)). The mixture is incubated on Jitter-Bug, 5 at room temperature for 30 min.

Washes and Elution: The plate is placed on a magnet and washed three times with wash buffer. The supernatant is removed after ensuring that all MPs are captured by the magnet and 250 ul of wash buffer are added. After the washes the samples are transferred into a new 96-well plate. The new plate is then placed on the magnet and the supernatant is removed after ensuring that all MPs are captured by the magnet. 250 ul of wash buffer are then added after removing the plate from the magnet. The plate is then placed on the magnet and the supernatant is removed after ensuring that all MPs are captured by the magnet. 20 ul of elution buffer are then added and the mixture is incubated on JitterBug, 5 at room temperature for 30 nin.

Filter out MPs and transfer to 384-well plate: The standard and samples are transferred into a 384-well filter plate placed on top of a 384-well assay plate. The plate is then centrifuged at room temperature at 3000 rpm with a plate rotor. The filter plate is removed and the appropriate calibrators are added. The plate is covered and is ready to be run on SMD.

SMD: An aliquot is pumped into the analyzer. Individually-labeled antibodies are measured during capillary flow by setting the interrogation volume such that the emission of only 1 fluorescent molecule is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention is determined by the mean+3 SD method.

Example 7

Concentration Range for cTnI in a Population of Normal Non-Diseased Subjects

A reference range or normal range for cTnI concentrations in human serum was established using serum samples from 88 apparently healthy subjects (non-diseased). A sandwich immunoassay as described in Example 4 was performed and the number of signals or events as described above were counted using the single particle analyzer system of the invention. The concentration of serum troponin I was determined by correlating the signals detected by the analyzer with the standard curve as described above. All assays were perfumed in quadruplicate.

Figure 17:
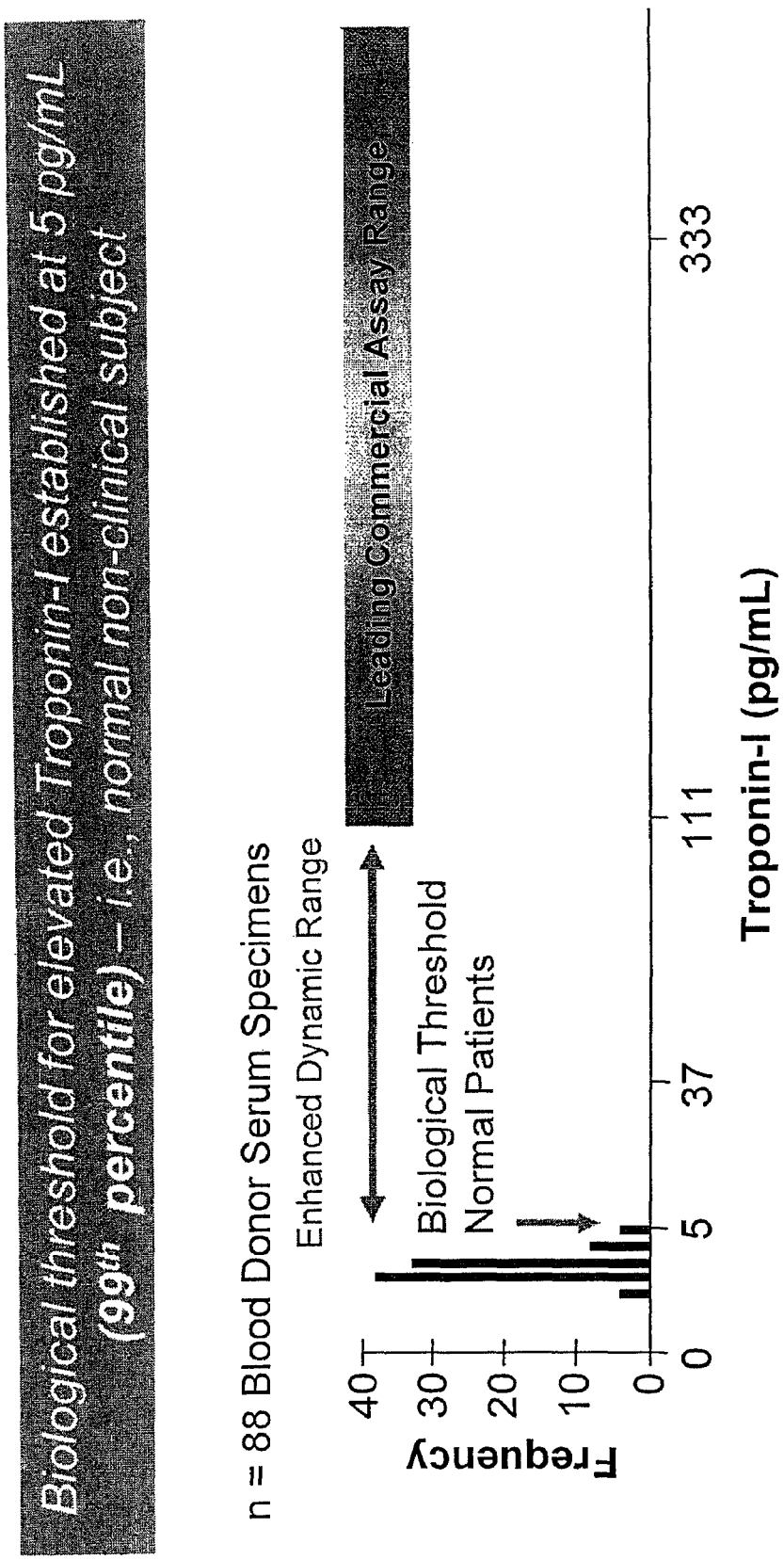
FIG. 17. Serum concentrations of cardiac troponin I in samples from normal donors.

In accordance with recommendations by the current European and American Cardiology Societies (ESC/ACC) troponin assays should quantify accurately the 99th percentile of the normal range with an assay imprecision (CV) of less than 10% in order to distinguish reliably between patients with ACS and patients without ischemic heart disease, and risk stratification for adverse cardiac events. The assay showed that the biological threshold (cutoff concentration) for TnI is at a TnI concentration of 7 pg/ml, which is established at the 99th percentile with a corresponding CV of 10% (FIG. 17). At the 10% CV level the precision profile points at a TnI concentration of 4 and 12 pg/ml.

In addition, the assay correlates well with the Troponin-I standard measurements provided by the National Institute of Standards and Technology.

The assay of the invention is sufficiently sensitive and precise to fulfill the requirements of the ESC/ACC, and it is the most sensitive assay for cardiac troponin I when compared to assays such as those described by Koerbin et al. (Ann Clin Biochem, 42:19-23 (2005). The assay of the invention has a 10-20 fold greater sensitivity than that currently available assays, which has determined the biological threshold range to be 111-333 pg/ml cTnI.

Example 8

Detection of Early Release of TnI into the Circulation of Patients with Acute Myocardial Infarction (AMI)

Study 1: 47 samples were obtained serially from 18 patients that presented with chest pain in the emergency department (ED). These patients all had non-ST elevated ECG were, and were diagnosed with AMI. The concentration of cTnI in the initial samples from all 18 patients was determined according to a commercial assay at the time of admission to the emergency room to be <350 pg/ml (10% cutpoint), and 12 were <100 pg/ml (99th %) percentile. These samples were tested at later times using the same commercial assay, and were determined to test positive for cTnI. The same serum samples were also assayed for TnI according to the assay of the invention as described in Examples 4 and 5, and the results compared to the results obtained using the commercial assay.

Figure 18:
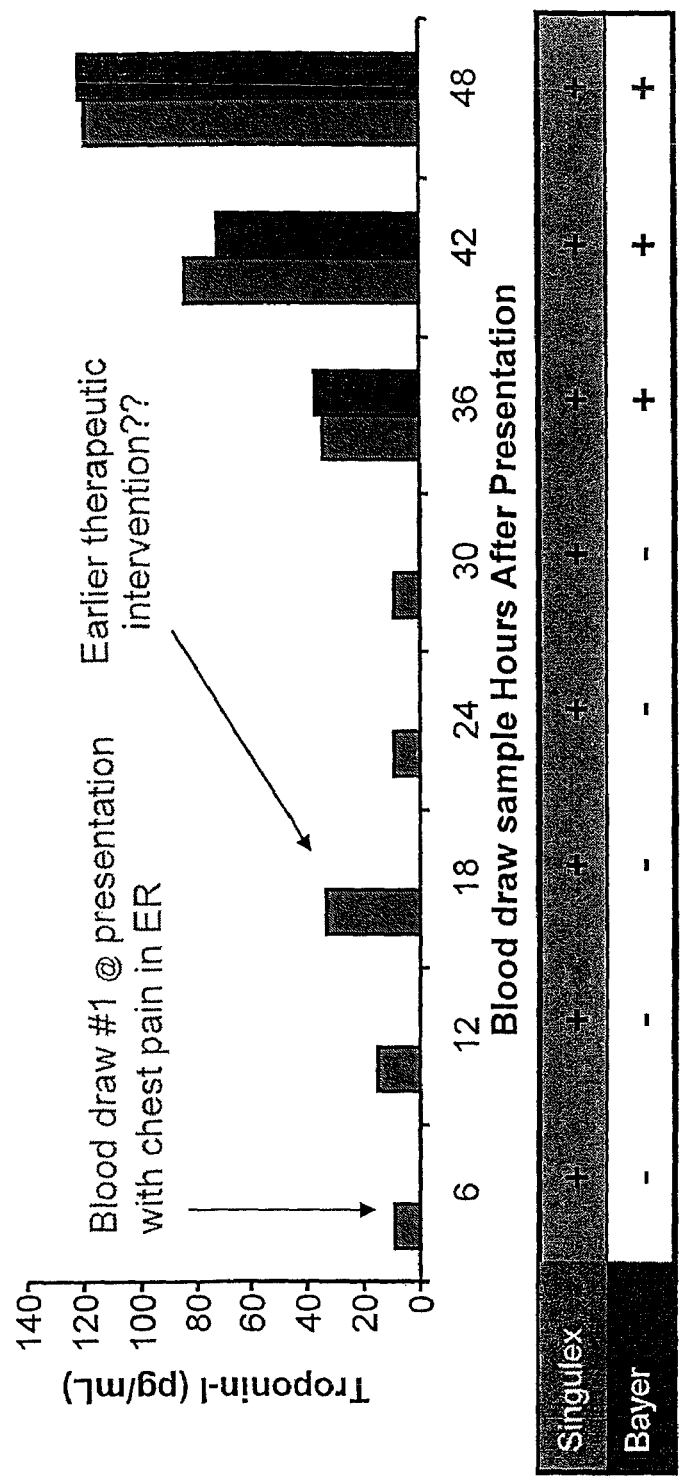
FIG. 18. Identification of acute myocardial infarct using serum cardiac troponin I.

Blood was drawn for the first time at the time the patient presented with chest pain (sample 1), and subsequently at intervals between 4-8 hours (samples 2 at 12 hours; sample 3 at 16 hours; sample 4 at 24 hours; sample 5 at 30 hours; sample 6 at 36 hours; sample 7 at 42 hours; and sample 8 at 48 hours). The serum was analyzed by the methods of the invention and by a current commercial method, and the results obtained are shown in FIG. 18. The analyzer of the invention detected TnI at the time the patient presented with chest pain (sample 1), while the commercial assay first detected cTnI at a much later time (sample 6 at 36 hours). The concentration of TnI in sample 3 exceeded the biological threshold level that was established using the analyzer of the invention (7 pg/ml, see FIGS. 17 and 18), and indicated that sample 3 is positive for TnI to suggest the incidence of a cardiac event. The biological threshold for the commercial assay lies between 111 and 333 pg/ml of TnI. Accordingly, sample 3 would not have been considered to indicate a possible cardiac event.

In addition, the methods and compositions of the present invention allow for much earlier diagnosis and possible intervention based on cardiac troponin levels, as evidenced by results for the first sample taken from the patients. In the 3 cases that had initial commercial assay cTnI values of between 100 and 350 ng/ml, all were positive for cTnI by the analytical methods of the invention (i.e., cTnI over 7 pg/ml). In the 12 cases that had initial commercial cTnI values of less than 100 pg/ml, 5 were determined to be positive for a cardiovascular event according to the assay of the invention (i.e., cTnI over 7 pg/ml). The prospective use of the assay of the invention would have detected 53% more AMI cases than the current commercial assay when the admission sample was tested.

Study 2: 50 additional serum samples, which tested negative according to the commercial assay, were tested using the analyzer and assay of the invention. Of the 50 samples, 36 were within the 99th % and determined to be within the normal range established by the assay of the invention. However, the remaining 14 samples that were determined to be within the commercial "normal" or non-diseased range, tested above the biological threshold established by the invention.

Therefore, the high sensitivity cTnI assay of the invention allows for the detection of myocardial damage in patients when cTnI serum levels are below threshold values by commercially available technology. The use of the highly sensitive and precise cTnI assay of the invention enables detection of AMI earlier than with existing cTnI assays, and thereby provides the opportunity for appropriate diagnosis and early medical intervention to improve the outcome.

Other Aspects

The detailed description set-forth above is provided to aid those skilled in the art in practicing the present invention. However, the invention described and claimed herein is not to be limited in scope by the specific embodiments and/or aspects herein disclosed because these embodiments and aspects are intended as illustration of several embodiments and aspects of the invention. Any equivalent embodiments and/or aspects are intended to be within the scope of this invention. Indeed, various modifications of the invention in addition to those shown and described herein will become apparent to those skilled in the art from the foregoing descriptions which do not depart from the spirit or scope of the present inventive discovery. Such modifications are also intended to fall within the scope of the appended claims.

When introducing elements of the present invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of analysis for determining the presence, absence or amount of a specific protein in a blood sample, comprising the steps of:
 (a) providing a processed sample, wherein the processed sample has been prepared by
  (i) extracting serum or plasma from the blood sample;
  (ii) contacting the serum or plasma with a selective capture agent specific for the protein, wherein the capture agent is immobilized or becomes immobilized on a surface;

(iii) adding a fluorescently-labeled specific binding partner for the protein, wherein the binding partner and the protein associate to form a protein-binding partner complex;

(iv) removing labeled binding partner that has not associated with the protein;

(v) releasing the protein-binding partner complex into solution or dissociating the labeled binding partner from the protein-binding partner complex so that the dissociated labeled binding partner moves into solution;

(b) sampling a portion of the processed sample, wherein the sampling is performed by a sampling system that comprises a pressure source to move the portion of the processed sample into a detection channel of a single molecule analyzer, wherein the detection channel is substantially transparent to at least some wavelengths of light and provides a channel through which the portion of the processed sample may flow, and the analyzer comprises a laser for providing excitation light, wherein the light is within the wavelengths to which the detection channel is substantially transparent; and (c) passing the portion of the processed sample through the detection channel of the analyzer using positive or negative pressure;

(d) focusing the excitation light on a portion of the detection channel, so that the light excites the labeled specific binding partner if present in the portion of the detection channel so that the labeled specific binding partner produces emitted light;

(e) passing the emitted light through an aperture so that the focusing of excitation light and passing of emitted light through the aperture define a molecule detection volume within the portion of the detection channel of between about 0.1 pL and about 25 pL;

(f) detecting, in discreet time bins, the emitted light that has passed through the aperture with a detector, wherein the detector transforms the light into an electronic signal; and (g) determining the presence, absence or amount of the specific protein in a blood sample by determining a threshold photon bin value based upon a distribution of background noise signal and analyzing the electronic signal from a plurality of the bins with a data analysis system operably connected to the detector that compares the signal for each bin to the threshold value to determine whether or not the labeled specific binding partner is present in the molecule detection volume.

2. The method of claim 1 wherein the protein is present in the sample at a concentration of about 100 femtomolar to about 1500 femtomolar.

3. The method of claim 1 wherein the protein is present in the sample at a concentration of 0.5-10 pg/ml.

4. The method of claim 1 wherein light emitted from the molecule detection volume is associated with a single labeled specific binding partner that has been excited by the excitation light.

5. The method of claim 1 wherein the labeled specific binding partner is associated with a particle, and the light emitted from the detection volume is associated with a single particle that has been excited by excitation light.

6. The method of claim 1 wherein the labeled specific binding partner has low photobleaching.

7. The method of claim 1, wherein the threshold value assumes a Poission distribution of the background noise signal.

8. The method of claim 1, wherein the threshold level is a set a fixed number of standard deviations above the background signal.

9. The method of claim 8, wherein the data analysis system determines a signal above the threshold level as a single labeled specific binding partner so that each bin is analyzed as a "yes" or "no" for the presence of the labeled specific binding partner.

10. The method of claim 1, wherein the bin time is longer than the time the labeled specific binding partner passes through the detection volume.

11. A method of determining the presence, absence or amount of an analyte comprising a specific binding substance in a sample, the method comprising:

(a) contacting the sample with a capture agent specific for the analyte and a fluorescently-labeled specific binding partner for the analyte to form a complex comprising the capture agent, the analyte and the labeled binding partner, wherein the capture agent is immobilized or becomes immobilized on a surface;

(b) removing labeled binding partner that has not associated with the analyte;

(c) releasing the analyte or the labeled binding partner from the complex so that the dissociated labeled binding partner moves into solution;

(d) passing the labeled binding partner through a detection channel of an analyzer, wherein the detection channel comprises a portion that is substantially transparent to at least some wavelengths of light and provides a channel through which the labeled binding partner may flow, and the analyzer comprises a laser for providing excitation light, wherein the light is within the wavelengths to which the portion of the detection channel is substantially transparent;

(d) focusing the excitation light within the portion of the detection channel, so that the light excites the labeled specific binding partner if present in the portion of the detection channel so that the labeled specific binding partner produces emitted light;

(e) passing the emitted light through an aperture so that the focusing of excitation light and passing of emitted light through the aperture define a detection volume within the portion of the detection channel of between about 0.1 pL and about 25 pL;

(f) detecting, in discreet time bins, the emitted light that has passed through the aperture with a detector, wherein the detector transforms the light into an electronic signal; and (g) determining the presence, absence or amount of the analyte in the sample by determining a threshold photon bin value based upon a distribution of background noise signal and analyzing the electronic signal from a plurality of the bins with a data analysis system operably connected to the detector that compares the signal for each bin to the threshold value to determine whether or not the labeled specific binding partner is present in the detection volume.

12. The method of claim 11, wherein the threshold value assumes a Poission distribution of the background noise signal.

13. The method of claim 11, wherein the threshold level is a set a fixed number of standard deviations above the background signal.

14. The method of claim 11, wherein the data analysis system determines a signal above the threshold level as single labeled specific binding partner so that each bin is analyzed as a "yes" or "no" for the presence of the labeled specific binding partner.

15. The method of claim 11, wherein the determining the presence, absence or amount of the analyte in the sample further comprises determining the number of bins having a photon bin count greater than the threshold level for a sample comprising a standard, and comparing the number of bins having a photon bin count greater to a threshold level for the sample comprising the analyte to the number of bins having a photon bin count greater than a threshold level for the sample comprising the standard.

16. The method of claim 11, wherein the bin time is longer than the time the labeled specific binding partner passes through the detection volume.

* * * * *